United States Patent
Shiono

(10) Patent No.: US 6,229,020 B1
(45) Date of Patent: May 8, 2001

(54) REAGENTS FOR PREPARATION OF CAGED COMPOUNDS, AND METHOD FOR PREPARATION OF THE CAGED COMPOUNDS

(75) Inventor: Hirofumi Shiono, Shizuoka (JP)

(73) Assignee: Laboratory of Molecular Biophotonics, Shizuoka (JP)

(*) Notice: Subject to any disclaimer, the term of this patent is extended or adjusted under 35 U.S.C. 154(b) by 0 days.

(21) Appl. No.: 09/480,455

(22) Filed: Jan. 11, 2000

(30) Foreign Application Priority Data

Jan. 12, 1999 (JP) .................................. 11-005654

(51) Int. Cl.[7] ...................... C07C 229/44; C07D 207/40; C07D 207/46; C07D 207/48
(52) U.S. Cl. .......................... 548/110; 548/542; 548/545; 548/547; 560/43
(58) Field of Search ................... 548/542, 545, 548/547, 110; 560/43

(56) References Cited

FOREIGN PATENT DOCUMENTS 11-29500   2/1999   (JP) .
WO 91/03549   3/1991   (WO) .

OTHER PUBLICATIONS

Porter et al., "Photoregulation of Enzymes", Chapter 4, John Wiley & Sons, Inc., 1993, pp. 197–241.
von Frank Kienzie, "Die Reaktion von Phthalaldehyden mit 3–Nitropropionsäureenstern. Ein einfacher Zugang zu–3–Nitro–2–naphthoesäuren", Halvetica Chimica Acta—vol. 63, Fasc. 8 (1980)—Nr. 249, pp. 2364–2369.
Wani et al., "Plant Antitumor Agents. 18[1]. Synthesis and Biological Activity of Camptothecin Analogues", J. Med. Chem. 1989, vol. 23, pp. 554–560.

"Protection for the Carboxyl Group" Chapter 5, pp. 224–251. 1995.

(List continued on next page.)

Primary Examiner—Jane Oswecki
(74) Attorney, Agent, or Firm—Leydig, Voit & Mayer, Ltd.

(57) ABSTRACT

A new reagent for preparation of a caged compound in accordance with the present invention is a compound having, as a basic structure, an N-succinimidyl cinnamate structure expressed by the following formula 1:

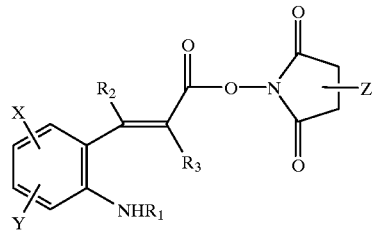

formula 1

Another reagent for preparation of a caged compound in accordance with the present invention is a compound having, as a basic structure, a p-nitrophenyl cinnamate structure expressed by the following formula 3:

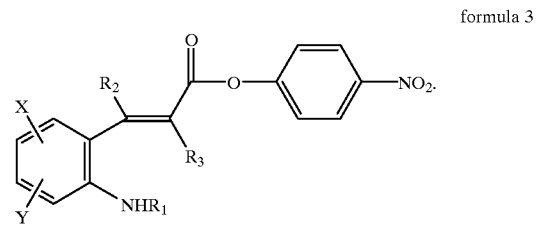

formula 3

4 Claims, 7 Drawing Sheets

OTHER PUBLICATIONS

Sheehan et al., "A New Method of Forming Peptide Bonds", Communications to the Editor, vol. 77, Feb. 20, 1955, pp. 1067–1068.

Sheehan et al., "A Rapid Synthesis or Oligopeptide Derivatives without Isolation of Intermediates", Journal of the American Chemical Society, 87:11, Jun. 5, 1965, pp. 2492–2493.

Sheehan et al., "The Use of Water–Soluble and Basic Carbodimides in Peptide Synthesis", Contribution from the Department of Chemistry, Massachusetts Institute of Technology, vol. 21, Received Dec. 23, 1965, pp. 439–441.

Artico et al., "Heterocycles with a Benzothiadiazepine Moiety—1. Synthesis of Pyrrolo[1,2–b]–s–Triazolo[3,4–d][1,2,5]Benzothiadiazepine 5,5,–Dioxide" Synthetic Communications, 22(10) (1992) pp. 1433–1439.

Sato et al., "Synthesis of 3–(2–Amino) Benxylidene–2, 5–Piperazinedione and its Conversion to 1–Azanaphthalenone and Spiro [Indo–Linepiperazine] Dione Derivatives" Heterocycles, vol. 33, No. 2, 1992, pp. 589–595.

Mack et al., "Synthesis of Some Novel 1,3–Dihydro–2H–benzimodazol–2–ylidenes", J. Org. Chem. vol. 58, No. 22, 1993, pp. 6158–6162.

Martin et al., "Die Synthese von Azaisomeren des Triesters von PQQ: 3H–Pyrrolo[3,2–f]–, 1H–Pyrrolo[3,2–h]–und 7H–Pyrrolo[2,3–h]chinolinchinon–Derivate", Helvetica Chimica Acta, vol. 77, 1994, pp. 111–120.

Anderson et al., "N–Hydroxysuccinimide Esters in Peptide Synthesis", Communications to the Editor, Oct. 5, 1963, vol. 85, p. 3039.

Collman et al., "Hydrolytic Cleavage of N–Terminal Peptide Bonds by a Cobalt Chelate", Communications to the Editor, vol. 85, Oct. 5, 1963, pp. 3039–3040.

Dondoni et al., "Total Synthesis of (+)–Polyoxin J", J. Chem. Soc., Chem, Commun., 1995, pp. 2127–2128.

Renn et al., "Large–Scale Synthesis of the Bifunctional Chelating Agent 2–(p–Nitrobenzyl)–1,4,7,10–tetraazacyclododecane–N, N', N", N'''–tetraacetic Acid, and the Determination of its Enantiomeric Purity by Chiral Chromatography", Bioconjugate Chem., vol. 3, No. 6, 1992, pp. 563–569.

Sheradsky et al., "Intramolecular Oxidative Diels–Alder Reaction of N–Sorbyl–L–Proline Acylhydrazides", Tetrahedron Letters, vol. 32, No. 1, 1991, pp. 133–136.

Southwick et al., "The Amino Blocking Reagent—1–Isopropyl–3–ethoxy–44–nitro–2–oxo–3–pyrroline and the N–Hydroxysuccinimide Esters of N–(1–Cyclohexyl– and 1–Isopropyl–4–nitro–2–oxo–3–pyrroline–3–yl)glycine", J. Org. Chem, vol. 49, 1984, pp. 1130–1134.

Takeda et al., "A Convenient Synthesis of Peptide Using Oxallates", Tetrahedron Letters, vol. 24, No. 41, 1983, pp. 4451–4454.

Billington et al., "The Synthesis of Novel Bifunctional Linker Molecules", Tetrahedron, vol. 47, No. 28, 1991, pp. 5231–5236.

Huang et al., "Acyclic Nucleic Acid Analogues: Synthesis and Oligomerization of γ,4–Diamino–2–oxo–1(2H)–pyrimidinepentanoic Acid and δ, 4–Diamino–2–oxo–1(2H)–pyrimidinehexanoic Acid", J. Org. Chem., vol. 56, No. 21, 1991, pp. 6007–6018.

Pfeiffer et al., "Aminolysis of Activated Esters of Indole–3–acetic Acid in Acetonitrile", J. Org. Chem., vol. 58, No. 3, 1993, pp. 735–740.

Cabaret et al., "An Efficient Synthesis of Aryl Phenaceturates Using Acid Catalyzed Dicyclohexylcarbodiimide Esterification and Transient N–tert–Butoxycarbonylation", Synthesis, Short Papers, Received Oct. 8, 1993, pp. 480–482.

Barral et al., "Preparation of $N^\chi$–(2–Nitropenylthio)–$N^\epsilon$–acyl Lysine Derivatives", Synthesis, Communications, Dec. 1973, pp. 795–796.

Feldstein et al., "Acetyl Transfer during Hydrogenation of p–Nitrophenyl Acetate", Notes, vol. 26, Received Sep. 1, 1990, p. 1656.

Anderson et al., "t–Butyl Esters of Amino Acids and Peptides and their Use in Peptide Synthesis", The Organic Chemical Research Section, American Cyanamide Co., New York, vol. 82, Jul. 5, 1960, pp. 3359–3363.

Bodanszky et al., "An Improved Synthesis of Oxytocin", The Department of Biochemistry, Cornel Univ. Medical College, vol. 81, May 1959, pp. 2504–2507.

Anderson et al., "The Preparation of Secondary Benzylic Amines from Reactive Benzylic Tosylates", Communications, No. 9, Sep. 1974, pp. 665–666.

Tsuji et al., "Studies on Anti–inflammatory Agents. IV. Synthesis and Pharmacological Properties of 1,5–Diarylpyrazoles and Related Derivatives", Chem. Pharm. Bull. 45(6) (1997) pp. 987–995.

Padmanabhan et al., "A Convenient One Pot Procedure for N–Methylation of Aromatic Amines using Trimethyl Orthoformate", Synthetic Communications, 27(4) (997), pp. 691–699.

Zhao et al., "A Concise Synthesis of the Pyrroloquinoline Nucleus of the Makaluvamine Alkaloids", Synthetic Communications, 27(12) (1997), pp. 2103–2110.

Ramrao et al., "Phase Transfer Catalysed N–Monoalkylation of Amino Anthraquinones+", Synthetic Communications, 21(10&11) (1991), pp. 1129–1135.

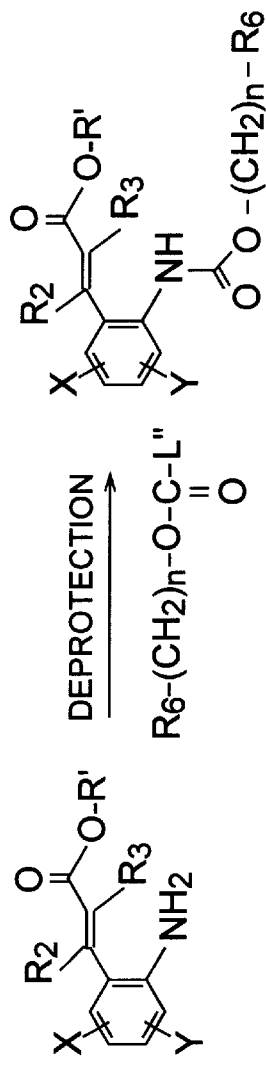
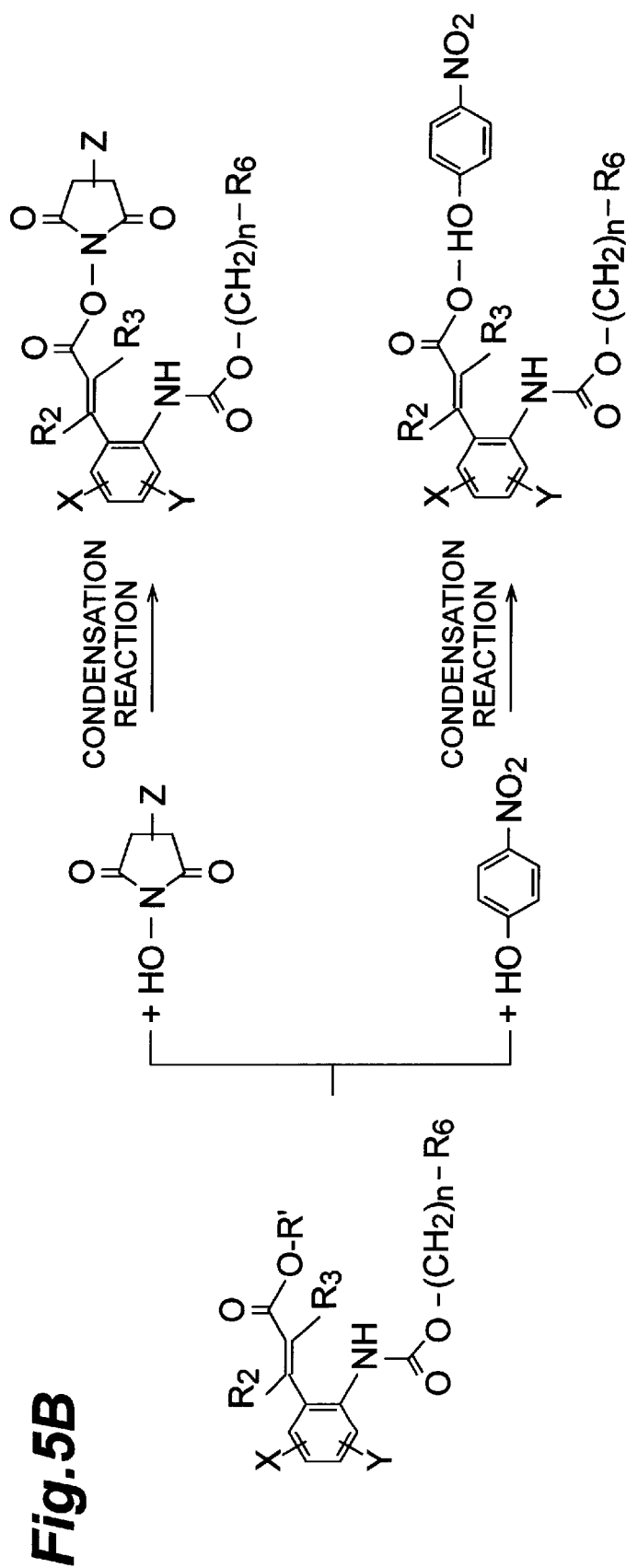
Fig.5A
Fig.5B

REAGENTS FOR PREPARATION OF CAGED COMPOUNDS, AND METHOD FOR PREPARATION OF THE CAGED COMPOUNDS

BACKGROUND OF THE INVENTION

1. Field of the Invention

The present invention relates to new reagents for preparation of caged compounds, and new caging methods using the same.

2. Related Background Art

For investigating the mechanism of action of a substance in an organism, it is necessary to quantitatively measure the rise and fall of this substance within a biological system in a short period of time. Further, it is important to observe various changes following the substance introduced into the system.

On the other hand, biological reactions are mostly very fast, and a plurality of reactions usually progress at the same time while complicatedly relating to each other. Therefore, when the above-mentioned substance is added from the outside, the process of its diffusing within the system rather becomes the rate-determining step, thereby often making it hard to clearly grasp the subsequent reaction to be determined in practice.

SUMMARY OF THE INVENTION

For overcoming such a problem, various methods have been proposed as to a method of rapidly adding a target substance. As one of such methods, a method using a technique based on irradiation with light, i.e., so-called caged reagent, has been reported. In general, this method comprises the steps of introducing into a biological system a caged compound (which refers to a compound in which a so-called caging group is introduced or a compound labeled with a caging group) in which a specific protective group protects an active part of a physiologically active substance to be traced; verifying that this substance has sufficiently diffused to a point of application; and liberating the protective group (caging group) upon irradiation with light, so as to release the target substance, thereby making it possible to trace the reaction caused by the substance. This protective group is characterized in that it can attain deprotection (release of the protective group) upon irradiation with light alone, it can achieve deprotection very fast, and it allows the light irradiation to be narrowed to only a specific part as necessary. The present invention provides new reagents capable of preparing caged compounds having such a function with a new structure by a simple reaction. Also, the present invention provides methods of yielding caged compounds by introducing a caging group into a target physiologically active substance by using these new reagents.

As a result of diligent studies, the inventor has succeeded in finding new reagents which can prepare caged compounds having such an excellent function by a simple reaction. Also, the inventor has succeeded in establishing methods of caging various compounds by using these new reagents, thereby accomplishing the present invention.

Namely, a new reagent for preparation of caged compounds in accordance with the present invention is a compound having, as a basic structure, an N-succinimidyl aminocinnamate structure expressed by the following formula 1:

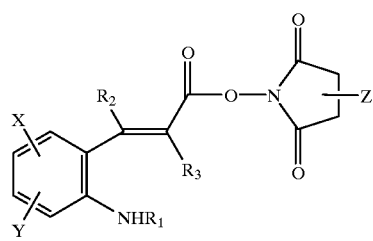

formula 1 where X and Y may be identical or different, each representing one kind selected from the group consisting of a hydrogen atom, a halogen atom, an alkyl group having a carbon number from 1 to 4, an alkyloxy group having a carbon number from I to 4, a benzo group, and an alkylamino group having a carbon number from 1 to 4; $R_1$ represents one kind selected from the group consisting of a hydrogen atom, an alkyl group having a carbon number from 1 to 4, and a group expressed by the following formula 2:

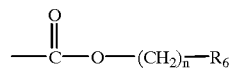

formula 2 where $R_6$ represents one kind selected from the group consisting of an alkyl group having a carbon number from 1 to 4, a phenyl group, and an alkylsilyl group having a carbon number from 1 to 4, and n represents an integer from 0 to 2;

$R_2$ and $R_3$ may be identical or different, each representing one kind selected from the group consisting of a hydrogen and an alkyl group having a carbon number from 1 to 4; and Z represents one kind selected from the group consisting of a hydrogen atom and $SO_3M$, where M represents one kind selected from the group consisting of a hydrogen atom, an alkali metal, and an alkaline-earth metal.

As preferable examples of the new reagent for preparation of caged compounds in accordance with the present invention, those having the respective structures shown in the following formulae 4 to 17 can be noted specifically:

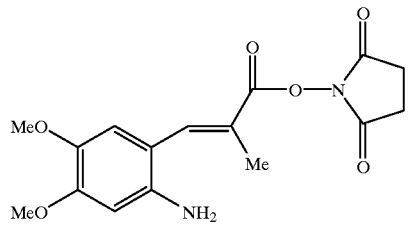

formula 4

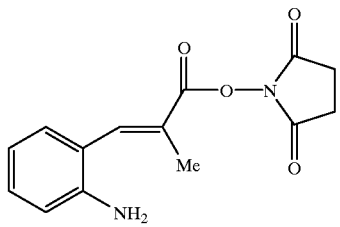

formula 5 formula 6
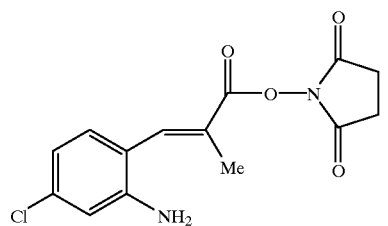
formula 7
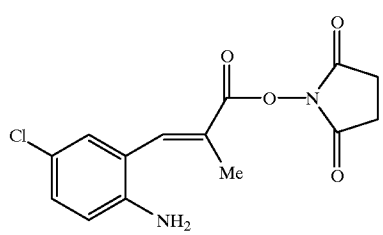
formula 8
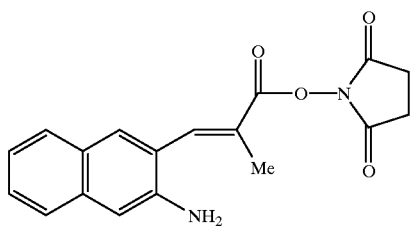
formula 9
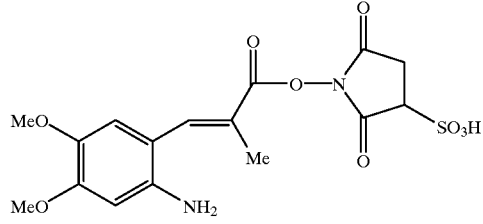
formula 10
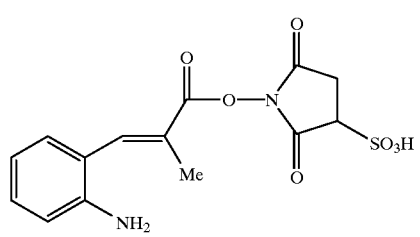
formula 11
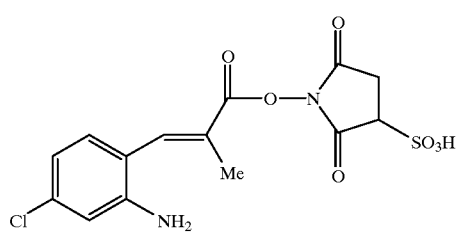
formula 12
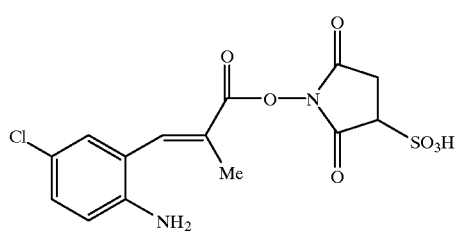
formula 13
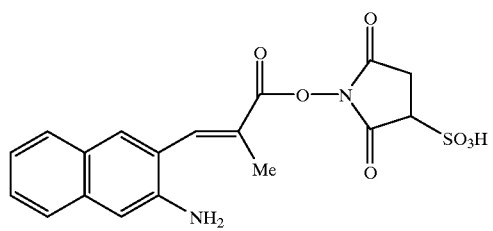
formula 14
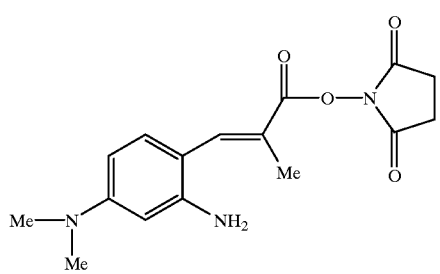
formula 15
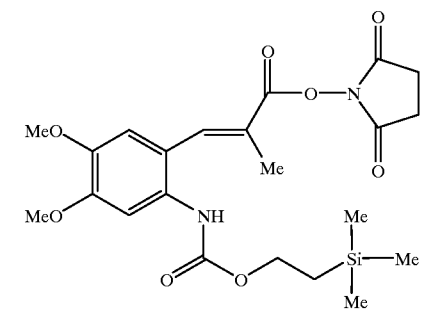
formula 16
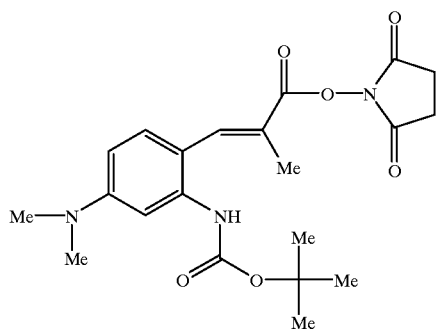

-continued formula 17

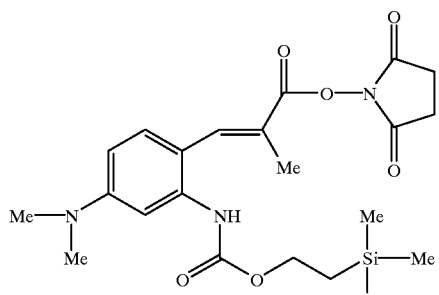

Another new reagent for preparation of caged compounds in accordance with the present invention is a compound having, as a basic structure, a nitrophenyl ester structure expressed by the following formula 3:

formula 3

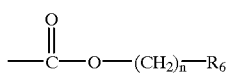

where X and Y may be identical or different, each representing one kind selected from the group consisting of a hydrogen atom, a halogen atom, an alkyl group having a carbon number from 1 to 4, an alkyloxy group having a carbon number from 1 to 4, a benzo group, and an alkylamino group having a carbon number from 1 to 4; $R_1$ represents one kind selected from the group consisting of a hydrogen atom, an alkyl group having a carbon number from 1 to 4, and a group expressed by the following formula 2:

formula 2

$$-\overset{\text{O}}{\underset{\|}{C}}-O-(CH_2)_n-R_6$$

where $R_6$ represents one kind selected from the group consisting of an alkyl group having a carbon number from 1 to 4, a phenyl group, and an alkylsilyl group having a carbon number from 1 to 4, and n represents an integer from 0 to 2; and $R_2$ and $R_3$ may be identical or different, each representing one kind selected from the group consisting of a hydrogen and an alkyl group having a carbon number from 1 to 4.

As preferable examples of the new reagent for preparation of caged compounds in accordance with the present invention, those having the respective structures shown in the following formulae 18 to 23 can be noted specifically:

formula 18

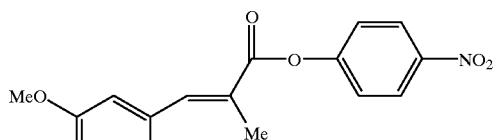

formula 19

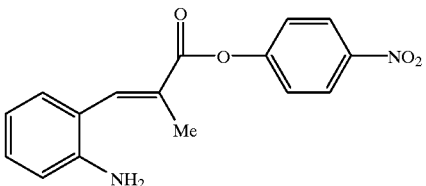

formula 20

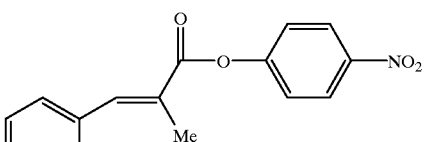

formula 21

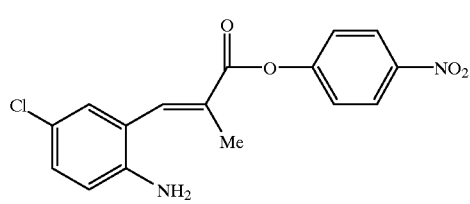

formula 22

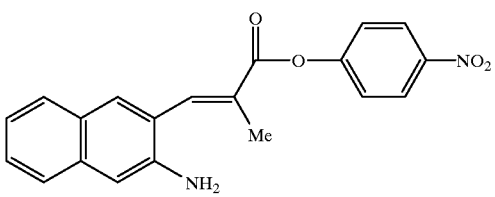

formula 23

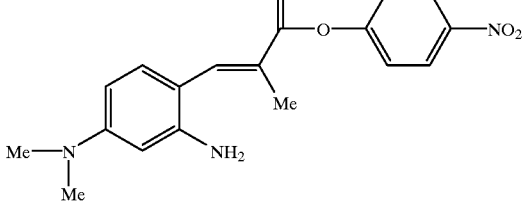

On the other hand, the methods in accordance with the present invention are caging methods in which the above-mentioned reagents for preparation of caged compounds are reacted with compounds having various functional groups (physiologically active substances such as amino acids), so as to prepare caged compounds.

FIGS. 1A and 1B show caging methods of compounds having various functional groups, in which the reagents for preparation of caged compounds in accordance with the present invention are used. FIG. 2 shows a photolysis reaction of a caged compound obtained. As shown in FIGS. 1A and 1B, N-succinimidyl group and p-nitrophenyl group easily react with various functional groups under mild reaction conditions. Preferable examples of the above-mentioned functional groups include amino group, hydroxide group, phenol group, thiol group, carboxylic acid group, and the like. The caged compounds obtained by the methods of the present invention are stable in the dark since the double bond of cinnamate group is kept in a trans (E) form.

BRIEF DESCRIPTION OF THE DRAWINGS

FIGS. 5A and 5B are reaction flowcharts showing an example of introducing a protective group to an aromatic amino group in a synthesizing route of reagents for preparation of caged compounds in accordance with the present invention;

DESCRIPTION OF THE PREFERRED EMBODIMENTS

In the following, the present invention will be explained further in detail.
Synthesizing Method The method of synthesizing reagents for preparation of caged compounds in accordance with the present invention is not restricted in particular, and known organic chemistry reactions are favorably usable in general. Specifically, reagents for preparation of caged compounds having various substituents in accordance with the present invention can easily be synthesized with a favorable yield and a high purity according to the synthesizing route shown in FIGS. 3A to 3E in the case of compounds having an N-succinimidyl aminocinnamate structure as their basic structure, and according to the synthesizing route shown in FIGS. 4A to 4E in the case of compounds having a p-nitrophenyl aminocinnamate structure as their basic structure.

Figure 3A:
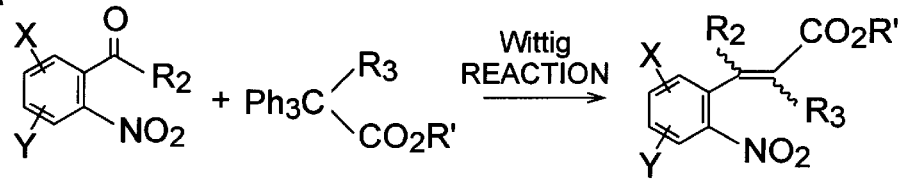
FIGS. 3A to 3E are reaction flowcharts showing an example of synthesizing routes of reagents for preparation of caged compounds having an N-succinimidyl structure in accordance with the present invention.

The synthesis of compounds having an N-succinimidyl aminocinnamate structure as a basic structure shown in FIGS. 3A to 3E includes a step of forming a cinnamate skeleton upon a reaction between a 2-nitrobenzaldehyde derivative (including a phenylketone derivative) having a favorable substituent and Wittig reagent (including Wadsworth-Emmons reagent) for introducing the favorable substituent (FIG. 3A). For the 2-nitrobenzaldehyde derivative (including a phenylketone derivative) and Wittig reagent (including Wadsworth-Emmons reagent), which are necessary starting materials, commercially available products can be used. Also, they can be synthesized by conventionally known organic synthesizing methods (Organic Synthesis, col. vol. 3, 641; Organic Synthesis, col. vol. 4,735; Organic Synthesis, col. vol. 5,825; Kienzle et al., Helv. Chim. Acta, 63 (8), 2364–2369 (1980); and Wani et al., J. Med. Chem. 1980, 23, 554–560). The reaction condition of Wittig reaction is not restricted in particular, and known conditions are usable in general (e.g., Organic Reaction, vol. 14, p. 270–423 (1965); and Organic Reaction, vol. 25, 73 (1977)). It is easy for those skilled in the art to select and optimize a favorable reaction condition in view of such literatures and the like.

Here, the resulting cinnamate derivative may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can easily verify the existence of double bond, ester group, and nitro group. Also, various known or commercially available liquid chromatographs, gas chromatographs, and the like can be used for determining the yield and purity of the product.

Figure 3B:
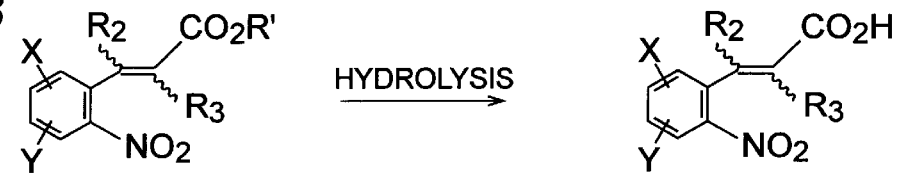

Further, the synthesis shown in FIGS. 3A to 3E includes a reaction of hydrolyzing an ester group into a carboxylic acid (FIG. 3B). The method of reaction for hydrolyzing such an ester (which is a methyl or ethyl ester in general) is not restricted in particular either, and known methods (Greene et al., "Protective Group in Organic Synthesis," 2nd ed., p. 224–251, John Wiley & Sons (1991)) can favorably be used in general. A specific example thereof is a reaction under an acidic or alkaline condition. The reaction condition of such a hydrolyzing reaction is not restricted in particular, and known conditions are usable in general. It is easy for those skilled in the art to select and optimize a favorable reaction condition in view of such a literature.

Here, the resulting acid derivative may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can easily verify the existence of double bond, carboxylic acid, and nitro group. Also, various known or commercially available liquid chromatographs, gas chromatographs, and the like can be used for determining the yield and purity of the product.

Figure 3C:
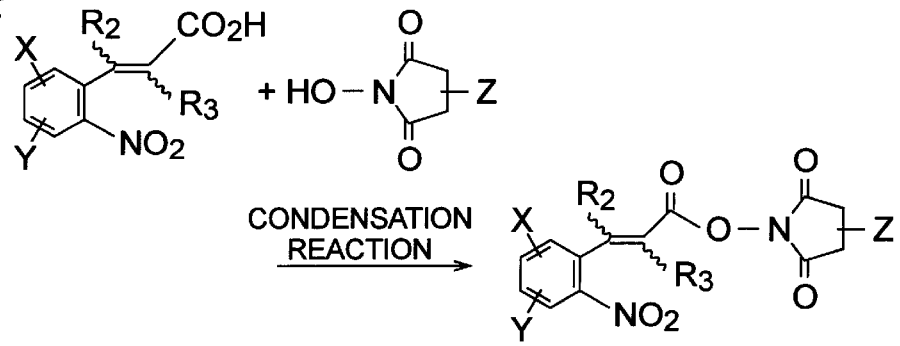

Further, the synthesis shown in FIGS. 3A to 3E includes a reaction by which the resulting acid derivative and N-hydroxysuccinimide (including its derivatives having sulfonic acid group) are dehydrated and condensed so as to form N-succinimidyl cinnamate (FIG. 3C). Here, the method of this dehydration and condensation reaction is not restricted in particular, and known methods (Anderson et al., J. Am. Chem. Soc., 85, 3039 (1963)) can favorably be used. Preferably, various dehydrators are used in a polar nonaqueous solvent (e.g., dimethylformaldehyde (DMF), 1,4-dioxane, tetrahydrofuran (THF), or dichloromethane). Specific examples of dehydrators include dicyclohexylcarbodiimide (DCC), 1-ethyl-3-(3-dimethylaminopropyl)-carbodiimide (EDC), and 1-ethyl-3-(3-dimethylaminopropyl)-carbodiimide hydrochloride (EDC-HCl). The reaction condition of such dehydration and condensation is not restricted in particular, and known conditions are usable in general. It is easy for those skilled in the art to select and optimize a favorable reaction condition in view of such a literature or the like.

The acid derivative having an N-succinimidyl ester group introduced therein obtained here may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can easily verify the existence of double bond, N-succinimidyl ester group, and nitro group. Also, various known or commercially available liquid chromatographs, gas chromatographs, and the like can be used for determining the yield and purity of the product.

Figure 3D:
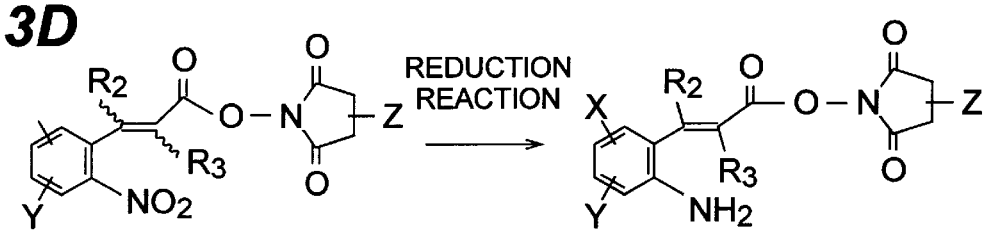
Figure 3E:
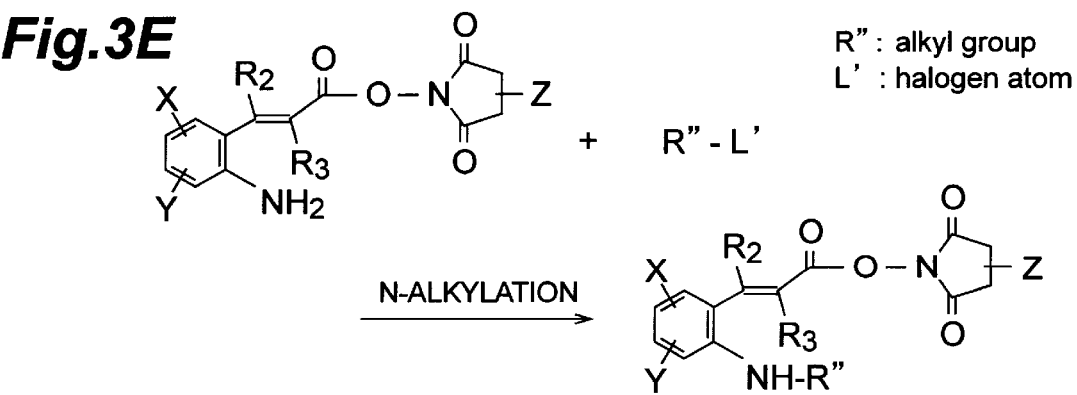

Further, the synthesis shown in FIGS. 3A to 3E includes a reaction by which the nitro group substituted at the aromatic ring of the N-succinimidyl cinnamate derivative is reduced to an amino group, so as to yield the final product (FIG. 3D). Here, the method of reducing the nitro group to the amino group is not restricted in particular, and various known methods (Articoa et al., Synthesis Comm., 22 (10), 1433–1439 (1992); Sato et al., Heterocycles, 33 (2), 589–595 (1992); Mack et al., J. Org. Chem., 58, 6158–6162 (1993); and Martin et al., Helvetica Chemica Acta, 17, 111–120 (1994)) can favorably be used. A specific example thereof is a reduction reaction with various metals under an acidic condition. A more specific example is a method using iron (including iron powder) under an acidic condition of acetic acid. The condition of such an acetic acid/iron reduction reaction is not restricted in particular, and known conditions are usable in general. It is easy for those skilled in the art to select and optimize a favorable reaction condition in view of such literatures or the like.

Figure 2:
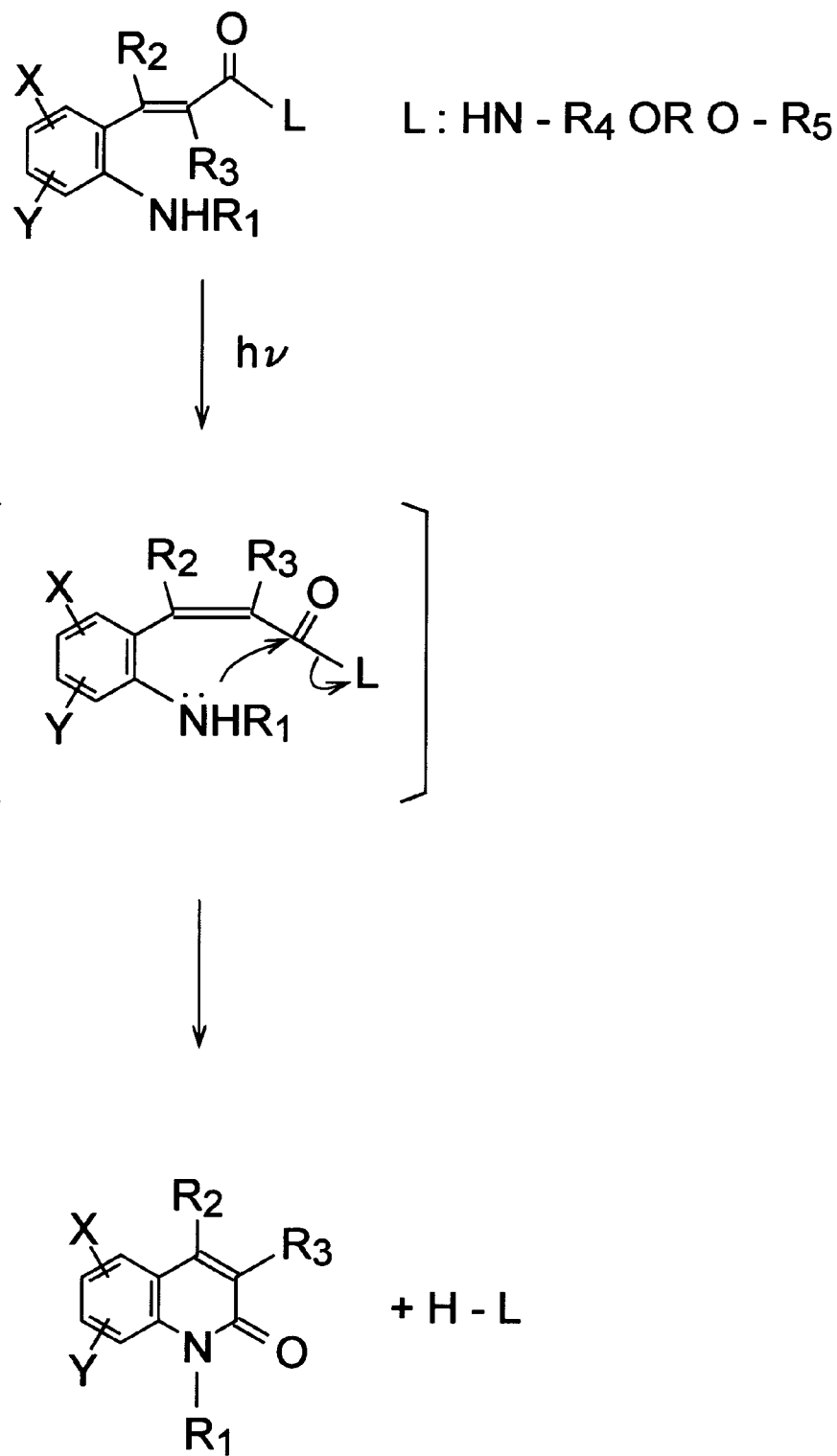
FIG. 2 is a reaction flowchart showing a photolysis reaction of a caged compound obtained by use of a reagent for preparation of caged compounds in accordance with the present invention.

The amino derivative obtained here is the final product, which becomes a reagent for preparation of caged compounds in accordance with the present invention. This amino derivative is in a trans form with respect to the double bond. It is because of the fact that, while a cis product is also generated upon the above-mentioned reduction reaction, a nitrogen-substituted coumarin derivative (carbostyril derivative) is easily formed according to a mechanism similar to the photoreaction shown in FIG. 2.

Means for verifying the structure is not restricted in particular, and known means for analyzing organic compounds are usable in general. Specifically, such means as infrared absorption spectrum (IR), nuclear magnetic resonance spectrum, mass spectrum, and the like can easily verify the existence of trans double bond, N-succinimidyl ester group, and aromatic amino group. Also, various known or commercially available liquid chromatographs, gas chromatographs, and the like can be used for determining the yield and purity of the product.

Further, the synthesizing route shown in FIGS. 3A to 3E includes a reaction for alkylating an aromatic amino group (FIG. 3E) in the case where, as the reagent for preparation of caged compounds in accordance with the present invention, one having an aromatic alkyl amino group is to be obtained. The method of this amino group alkylating reaction is not restricted in particular, and various known methods (Anderson et al., Synthesis, 1974, 665; Tsuji et al., Chem. Pharm. Bull., 45 (6), 987–995 (1997); Padmanabhan et al., Synth. Commun., 1997, 27 (4), 691–699; Zhao et al., Synth. Commun., 1997, 27 (12), 2103–2110; and Ramrao et al., Synth. Commun., 21 (1991) 10–11, 1129–1135) can favorably be used in general. Specific examples include reactions with alkyl halides, alkyl sulfonates, and alkyl tosylates. A more specific example includes a method using an alkyl iodide. The reaction condition of such alkylation is not restricted in particular, and various known methods can favorably be used. It is easy for those skilled in the art to select and optimize a favorable reaction condition in view of such literatures or the like.

Means for verifying the structure of the alkylamino derivative obtained here is not restricted in particular, and known means for analyzing organic compounds are usable in general. Specifically, such means as infrared absorption spectrum (IR), nuclear magnetic resonance spectrum, mass spectrum, and the like can easily verify the existence of trans double bond, N-succinimidyl ester group, and aromatic alkyl amino group. Also, various known or commercially available liquid chromatographs, gas chromatographs, and the like can be used for determining the yield and purity of the product.

Figure 4A:
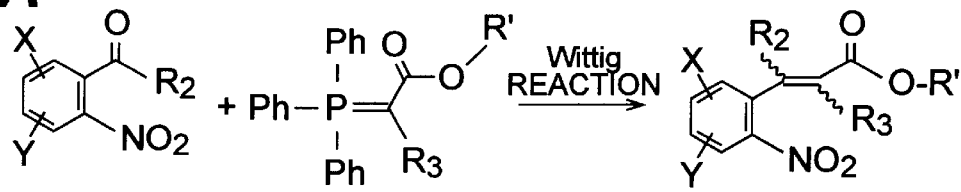
FIGS. 4A to 4E are reaction flowcharts showing an example of synthesizing routes of reagents for preparation of caged compounds having a nitrophenyl ester structure in accordance with the present invention.

The synthesis of compounds having a p-nitrophenyl aminocinnamate structure as a basic structure shown in FIGS. 4A to 4E includes a step of forming a cinnamate skeleton upon a reaction between a 2-nitrobenzaldehyde derivative (including a phenylketone derivative) having a favorable substituent and Wittig reagent (including Wadsworth-Emmons reagent) for introducing the favorable substituent (FIG. 4A). For the 2-nitrobenzaldehyde derivative (including a phenylketone derivative) and Wittig reagent (including Wadsworth-Emmons reagent), which are necessary starting materials, commercially available products can be used. Also, they can be synthesized by conventionally known organic synthesizing methods. The reaction condition of Wittig reaction is not restricted in particular, and known conditions are usable in general.

Here, the resulting cinnamate derivative may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can verify the existence of double bond, ester group, and nitro group. Also, various known or commercially available liquid chromatographs, gas chromatographs, and the like can be used for determining the yield and purity of the product.

Figure 4B:

Further, the synthesis shown in FIGS. 4A to 4E includes a reaction of reducing an aromatic nitro group to an amino group (FIG. 4B). Here, the method of reducing the nitro group to the amino group is not restricted in particular, and various known methods mentioned in the foregoing explanation of FIG. 3D can favorably be used in general. A specific example thereof is a reduction reaction with metals under an acidic condition of acetic acid. A more specific example is a method using iron (including iron powder) under an acidic condition of acetic acid. The condition of such an acetic acid/iron reduction reaction is not restricted in particular, and known conditions are usable in general. It is easy for those skilled in the art to select and optimize a favorable reaction condition in view of literatures.

The amino derivative obtained here is in a trans form with respect to the double bond. It is because of the fact that, while a cis product is also generated upon the above-mentioned reduction reaction, a nitrogen-substituted coumarin derivative (carbostyril derivative) is easily formed according to a mechanism similar to the photoreaction shown in FIG. 2.

Means for verifying the structure is not restricted in particular, and known means for analyzing organic compounds are usable in general. Specifically, such means as infrared absorption spectrum (IR), nuclear magnetic resonance spectrum, mass spectrum, and the like can easily verify the existence of trans double bond, ester group, and aromatic amino group. Also, various known or commercially available liquid chromatographs, gas chromatographs, and the like can be used for determining the yield and purity of the product.

Figure 4C:
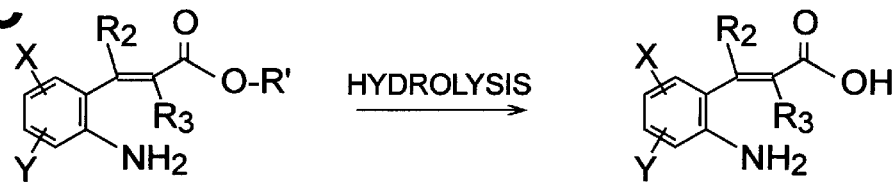

Further, the synthesis shown in FIGS. 4A to 4E includes a reaction of hydrolyzing an ester group into a carboxylic acid (FIG. 4C). The method of reaction for hydrolyzing such an ester (which is a methyl or ethyl ester in general) is not restricted in particular, and known methods can favorably be used in general. A specific example thereof is a reaction under an acidic or alkaline condition. The reaction condition of such a hydrolyzing reaction is not restricted in particular, and the reaction can be effected under known conditions in general. It is easy for those skilled in the art to select and optimize a favorable reaction condition in view of a literature. Means for verifying the structure is not restricted in particular either, and known means for analyzing organic compounds are usable in general. Specifically, such means as infrared absorption spectrum (IR), nuclear magnetic resonance spectrum, mass spectrum, and the like can verify the existence of trans double bond, carboxylic acid, and aromatic amino group. Also, various known or commercially available liquid chromatographs, gas chromatographs, and the like can be used for determining the yield and purity of the product.

Figure 4D:
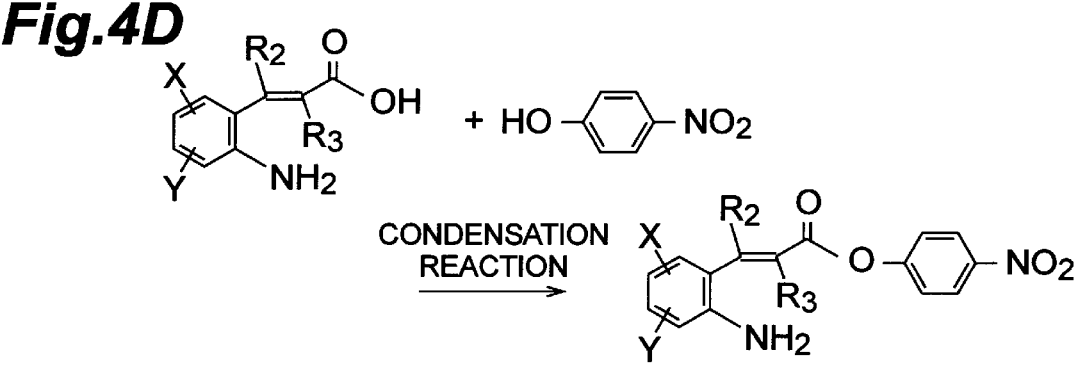
Figure 4E:
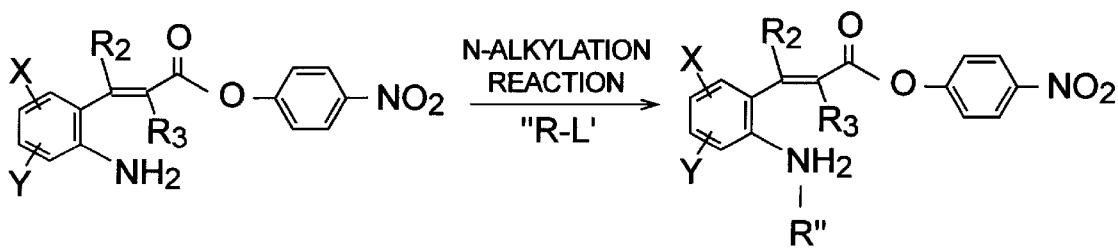

Further, the synthesis shown in FIGS. 4A to 4E includes a reaction by which the above-mentioned carboxylic acid derivative and p-nitrophenol are dehydrated and condensed, so as to yield p-nitropheyl aminocinnamate (FIG. 4D). The method of such a dehydration and condensation reaction is not restricted in particular, and known methods (Billington et al., Tetrahedron 47 (1991) 28, 5231–5236; Huang et al., J. Org. Chem. 56 (1991) 21, 6007–6018; Pfeiffer et al., J. Org. Chem. 58 (1993) 3, 735–740; and Cabaret et al., Synthesis (1994) 5, 480–482) can favorably be used in general. Preferably, various dehydrators are used in a polar nonaqueous solvent (e.g., dimethylformaldehyde, tetrahydrofuran, 1,4-dioxane, or dichloromethane). Specific examples of dehydrators include dicyclohexylcarbodiimide (DCC), 1-ethyl-3-(3-dimethylaminopropyl)-carbodiimide (EDC), and 1-ethyl-3-(3-dimethylaminopropyl)-carbodiimide hydrochloride (EDC-HCl). The reaction condition of such dehydration and condensation is not restricted in particular, and known conditions are usable in general. It is easy for those skilled in the art to select and optimize a favorable reaction condition in view of such literatures.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, ester group, aromatic amino group, and aromatic nitro group. Also, various known or commercially available liquid chromatographs, gas chromatographs, and the like can be used for determining the yield and purity of the product.

As mentioned above, reagents for preparation of caged compounds in accordance with the present invention can be obtained by the synthesizing routes shown in FIGS. 3A to 3E and 4A to 4E, and the target caged compounds can be obtained with a high yield and high selectivity by use of these reagents. Further, when a group expressed by the following formula 2:

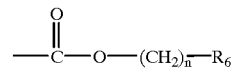

formula 2

(where $R_6$ represents one kind selected from the group consisting of an alkyl group having a carbon number from 1 to 4, a phenyl group, and an alkylsilyl group having a carbon number from 1 to 4, and n represents an integer from 0 to 2) is introduced to an aromatic amino group of the reagent for preparation of caged compounds, side reactions are suppressed, so that the target caged compounds can be obtained with a higher yield and higher selectivity. FIGS. 5A and 5B show an example of the method of introducing the protective group to the amino group, which does not limit the method of synthesizing the reagents for preparation of caged compounds in accordance with the present invention at all.

The synthesizing route shown in FIGS. 5A and 5B includes a reaction of introducing the protective group expressed by formula 2 to the aromatic amino group of the amino derivative obtained as an intermediate product (FIG. 5A). The method of reaction for introducing the protective group is not restricted in particular, and known methods can favorably be used in general. Specific examples include reactions with alkylsilylalkoxycarbonyl chloride and benzylcarboxy chloride. The reaction condition for introducing the protective group is not restricted in particular, and known conditions can be used in general to carry out the reaction (Greene et al., "Protective Group in organic Synthesis," 2nd ed., p. 315–345, John Wiley & Sons (1991)). It is easy for those skilled in the art to select and optimize a favorable reaction condition in view of such a literature.

Means for verifying the structure of the amino derivative having the protective group introduced therein obtained here is not restricted in particular, and known means for analyzing organic compounds are usable in general. Specifically, such means as infrared absorption spectrum (IR), nuclear magnetic resonance spectrum, mass spectrum, and the like can easily verify the existence of double bond, ester group, aromatic amino group, and aromatic amino group. Also, various known or commercially available liquid chromatographs, gas chromatographs, and the like can be used for determining the yield and purity of the product.

The synthesizing route shown in FIGS. 5A and 5B includes a reaction by which the amino derivative having the protective group introduced therein and N-succinimide or p-nitrophenol are dehydrated and condensed, so as to yield a reagent for preparation of caged compounds in accordance with the present invention (FIG. 5B). The reaction method and condition for the dehydration and condensation are not restricted in particular, and known methods and conditions are usable in general. Specifically, the methods and conditions similar to those in the reactions shown in FIGS. 3C and 4D can be mentioned. Also, means for verifying the structure of obtained compounds is not restricted in particular, and known means for analyzing organic compounds are usable in general. Specific examples thereof include analyzing means similar to those used for verifying the structures of compounds obtained by the reactions of FIGS. 3C and 4D.

The reagents for preparation of caged compounds to which the protective group expressed by formula 2 has been introduced are particularly effective when the target substance to be caged is an amino group having a secondary amino group (—NHR group). Here, the protective group expressed by formula 2 can easily be liberated in a post-processing step of the coupling (caging) reaction with the target substance. Specifically, in the case of trimethylsilyl-ethyloxycarbonyl group, it can easily be liberated by use of trifluoroacetic acid (TFA).

Reaction of Reagents for Preparation of Caged Compounds

Figure 1A:
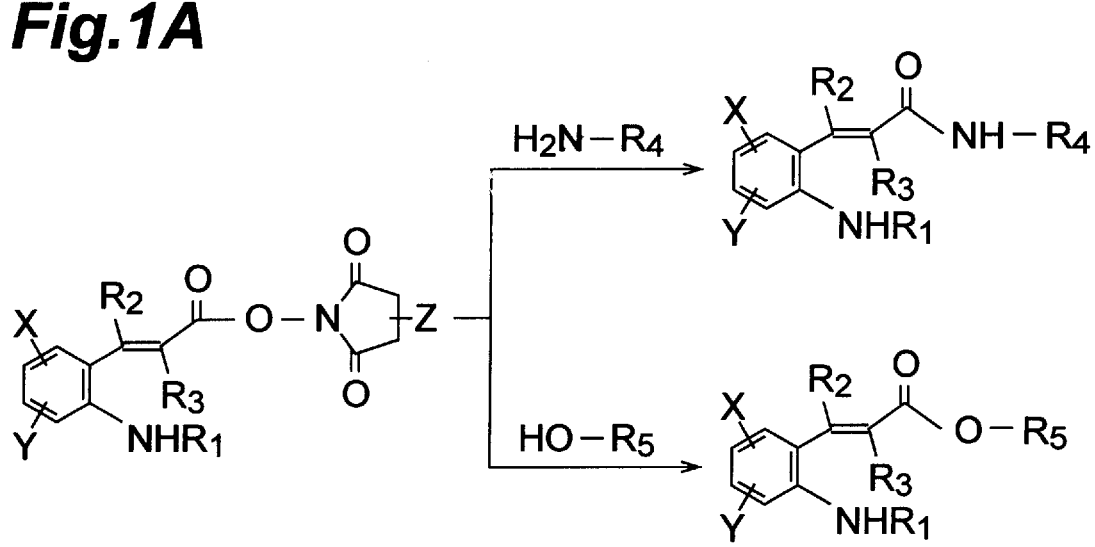
FIGS. 1A and 1B are reaction flowcharts showing examples of caging reactions using reagents for preparation of caged compounds having N-succinimidyl and nitrophenyl ester structures in accordance with the present invention, respectively.
Figure 1B:
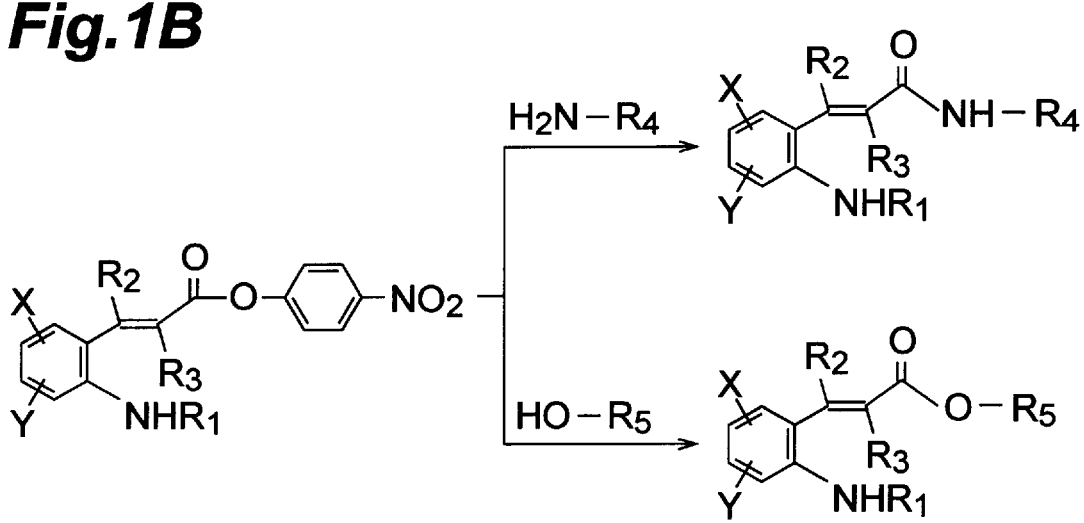

Since the above-mentioned reagents for preparation of caged compounds have an active ester group such as N-succinimide ester group or p-nitrophenyl group, they can easily react with various compounds having a functional group such as amino group under a mild condition (FIGS. 1A and 1B). In this reaction, water, an inorganic solvent, or their mixed solvents can be used as a reaction solvent. The reaction rapidly progresses at a reaction temperature from about 0° C. to about 100° C.

The concentration required for the reaction of the above-mentioned reagents for preparation of caged compounds is not restricted in particular, and they can also be used by an amount equivalent to the amount of the target substance to be caged or more. In the case where the target substance to be caged has a plurality of functional groups, a plurality of functional groups can be caged when the concentration of the reagents for preparation of caged compounds in accordance with the present invention is adjusted.

Figure 6:
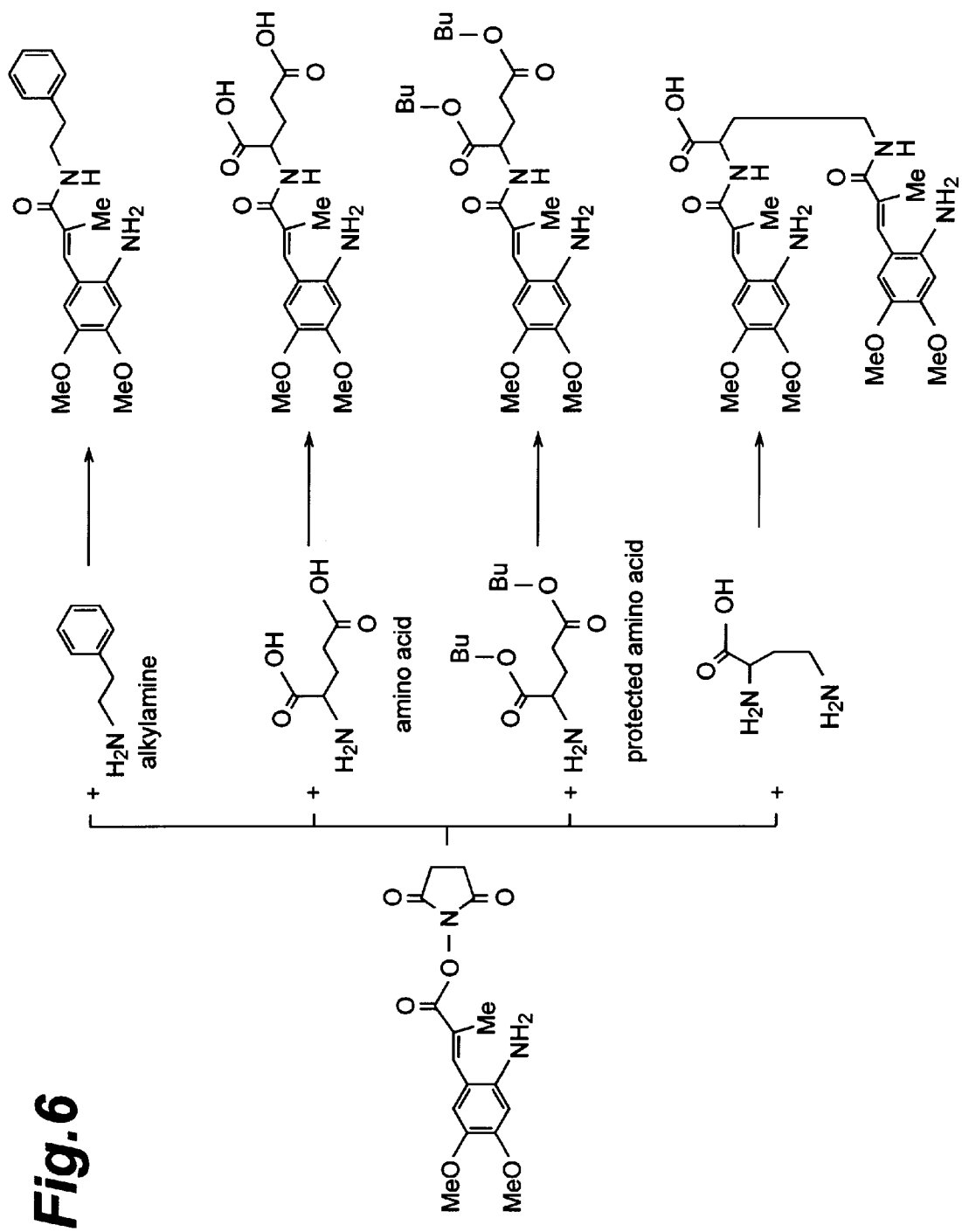
FIG. 6 is a reaction flowchart showing various applied examples of reaction of reagents for preparation of caged compounds having an N-succinimidyl structure in accordance with the present invention.
Figure 7:
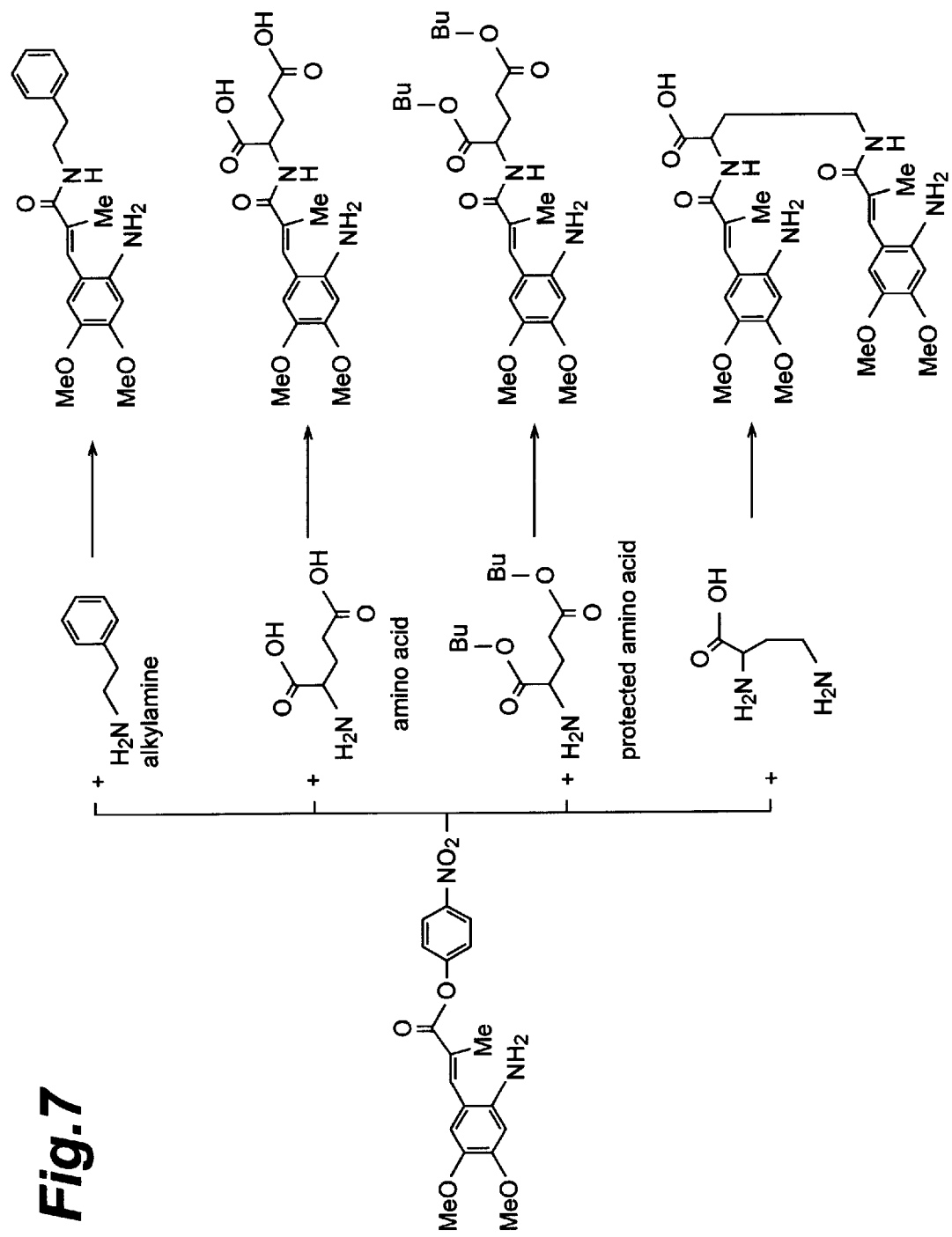
FIG. 7 is a reaction flowchart showing various applied examples of reaction of reagents for preparation of caged compounds having a nitrophenyl ester structure in accordance with the present invention.

In the case where the compound has a plurality of functional groups different from each other (e.g., amino group and carboxyl acid group), only a specific functional group may be caged according to the difference in reactivity of the reagents for preparation of caged compounds in accordance with the present invention between the functional groups. FIGS. 6 and 7 show various applied examples of reaction of reagents for preparation of caged compounds.

In the following, the present invention will be explained in further detail with reference to Examples, which do not limit the present invention at all.

EXAMPLES

Though the following examples of synthesis detail cases of (E) 3-(2-amino-4,5-dimethoxyphenyl)-2-methyl-2-propenoic acid N-succinimidyl ester, (E) 3-(2-amino-benzo[d]phenyl)-2-methyl-2-propenoic acid N-succinimidyl ester, (E) 3-(2-amino-4,5-dimethoxyphenyl)-2-methyl-2-propenoic acid p-nitrophenyl ester, (E) 3-(2-aminophenyl)-2-methyl-2-propenoic acid p-nitrophenyl ester, (E) 3-(2-amino-4-chlorophenyl)-2-methyl-2-propenoic acid p-nitrophenyl ester, and (E) 3-[4,5-dimethoxy-2-(trimethylsilylethoxycarbonyl)aminophenyl]-2-methyl-2-propenoic acid N-hydroxysuccinimidide ester, all the reagents for preparation of caged compounds in accordance with the present invention can be synthesized by use of 2-nitrobenzaldehyde derivatives (including a phenylketone derivative) having various functional groups introduced therein and Wittig reagent (including Wadsworth-Emmons reagent).

Synthesis of 3-(4,5-dimethoxy-2-nitrophenyl)-2-methyl-2-propenoic acid ethyl ester In benzene, 10 g (50.0 mmol) of 6-nitroveratlaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were stirred for 18 hours at room temperature so as to be reacted. This reaction was effected in a dark room. After the completion of the reaction, benzene was eliminated under a reduced pressure, whereby a white crystal was obtained. Thus obtained crystal was recrystallized from ethyl acetate, whereby 28.5 g of the aimed compound were obtained (yield: 76%).

The structure of this compound was verified by infrared absorption spectrum (IR), $^1$H-NMR, $^{13}$C-NMR, and TOF-MS. Here, JIR-WINSPEC50 manufactured by JEOL Ltd. was used for infrared absorption spectrum, JNM-LA300 manufactured by JEOL Ltd. was used for $^1$H-NMR and $^{13}$C-NMR, and KOMPACT MALDIIV manufactured by Shimadzu Corp. was used for TOF-MS (ditto for the following).

IR: 1700 cm$^{-1}$ (ester)

TOF-MS: 296 (M/C)

$^1$H-NMR (heavy chloroform, δ ppm): 7.93 (1H, s, proton at 3-site of propenoic acid), 7.74 (1H, s, proton at 3'-site of aromatic ring), 6.72 (1H, s, proton at 6'-site of aromatic ring), 4.29 (2H, q, J=7 Hz, methylene group proton of ethyl group), 3.99 ppm (3H, s, methyl group proton of methoxy group), 3.96 (3H, s, methyl group proton of methoxy group), 1.92 (3H, s, methyl group proton at 2-site of propene), 1.36 (3H, t, J=7 Hz, methyl group proton of ethyl group)

$^{13}$C-NMR (heavy chloroform, δ ppm): 167.9 (quaternary carbon, carbonyl carbon at 1-site), 153.1 (quaternary carbon, carbon at 5'-site of aromatic ring), 148.7 (quaternary carbon, carbon at 4'-site of aromatic ring), 145.1 (quaternary carbon, carbon at 2-site of propene), 143.4 (quaternary carbon, carbon at 2'-site of aromatic ring), 136.5 (CH, carbon at 3-site of propene), 126.6 (quaternary carbon, carbon at 1'-site of aromatic ring), 112.3 (CH, carbon at 6'-site of aromatic ring), 107.9 (CH, carbon at 3'-site of aromatic ring), 61.9 (CH$_2$, methylene group carbon of ethyl group), 56.5 (CH$_3$, methyl group carbon of methoxy group), 56.5 (CH$_3$, methyl group carbon of methoxy group), 14.3 (CH$_3$, methyl group carbon of ethyl group), 14.1 (CH$_3$, methyl group carbon at 2-site of propene).

Synthesis of 3-(4,5-dimethoxy-2-nitrophenyl)-2-methyl-2-propenoic acid

Into 250 ml of methanol, 11.3 g of thus obtained 3-(4,5-dimethoxy-2-nitrophenyl)-2-methyl-2-propenoic acid ethyl ester (1) were dissolved. With 45 ml of a 2-N aqueous sodium hydroxide solution being added thereto, the resulting mixture was reacted for 4 hours at 40° C. After the completion of the reaction, 1-N hydrochloric acid was used so as to adjust the pH in the system at 4, the system was cooled, and the precipitated crystal was filtered out, whereby 10.1 g of the aimed compound were obtained (yield: 99%).

The structure of this compound was verified by infrared absorption spectrum (IR), $^1$H-NMR, $^{13}$C-NMR, and TOF-MS.

IR: 1685 cm$^{-1}$ (carboxyl group).

TOF-MS: 268 (M/C)

$^1$H-NMR (heavy dimethyl sulfoxide, δ ppm): 12.60 (1H, bs, carboxyl group proton), 7.77 (1H, s, proton at 3-site of propene), 7.72 (1H, s, proton at 3'-site of aromatic ring), 6.97 (1H, s, proton at 6'-site of aromatic ring), 3.91 (3H, s, methyl group proton of methoxy group), 3.90 (3H, s, methyl group proton of methoxy group), 1.84 (3H, s, methyl group proton at 2-site of propene)

$^{13}$C-NMR (heavy dimethyl sulfoxide, δ ppm): 168.7 (quaternary carbon, carboxyl group carbon at 1-site), 152.8

(quaternary carbon, carbon at 5'-site of aromatic ring), 148.2 (quaternary carbon, carbon at 4'-site of aromatic ring), 139.8 (quaternary carbon, carbon at 2'-site of aromatic ring), 135.5 (CH, carbon at 3-site of propene), 129.4 (quaternary carbon, carbon at 2-site of propene), 125.7 (quaternary carbon, carbon at 1'-site of aromatic ring), 112.7 ( CH, carbon at 6'-site of aromatic ring), 107.7 (CH, carbon at 3'-site of aromatic ring), 56.4 ($CH_3$, methyl group carbon of methoxy group), 56.0 ($CH_3$, methyl group carbon of methoxy group), and 13.8 ($CH_3$, methyl group carbon at 2-site of propene).

Synthesis of 3-(4,5-dimethoxy-2-nitrophenyl)-2-methyl-2-propenoic acid N-succinimide ester (3)

Into 100 ml of dichloromethane, 7.0 g (26.2 mmol) of 3-(4,5-dimethoxy-2-nitrophenyl)-2-methyl-2-propenoic acid (2) and 3.5 g (30.0 mmol) of N-hydroxysuccinimide (manufactured by Wako Pure Chemical Industries, Ltd.) were dissolved, and 500 mg of dimethylaminopyridine (manufactured by Wako Pure Chemical Industries, Ltd.) were added thereto. While this solution was stirred under cooling with ice, 6.3 g (33.0 mmol) of 1-ethyl-3-(3-dimethylaminopropyl)-carbodiimide hydrochloride (EDC-HCl) (manufactured by Wako Pure Chemical Industries, Ltd.) were added thereto in portions. The mixture was returned to room temperature and then was stirred for 2 hours. After the end point of this reaction was verified by a thin layer chromatograph (TLC), the reaction liquid was concentrated under a reduced pressure and then was dissolved in 100 ml of ethyl acetate. After the ethyl acetate layer was washed and dried, the solvent was evaporated, whereby 8.3 g of the aimed product were obtained as an oily product (yield: 81%).

The structure of this compound was verified by $^1$H-NMR and $^{13}$C-NMR.

$^1$H-NMR (dimethyl sulfoxide, δ ppm): 8.29 (1H, s, proton at 3-site of propene), 7.78 (1H, s, proton at 3'-site of aromatic ring), 7.14 (1H, s, proton at 6'-site of aromatic ring), 3.94 (3H, s, methyl proton of methoxy group), 3.92 (3H, s, methyl proton of methoxy group), 2.87 (4H, s, methylene proton of succimidyl group), 2.01 (3H, s, methyl group proton at 2-site of propene)

$^{13}$C-NMR (heavy dimethyl sulfoxide, δ ppm): 170.4 (quaternary carbon, carbonyl carbon of succinimidyl group), 162.9 (quaternary carbon, carbonyl group carbon at 1-site), 153.1 (quaternary carbon, carbon at 5'-site of aromatic ring), 149.0 (quaternary carbon, carbon at 4'-site of aromatic ring), 141.3 (CH, carbon at 3-site of propene), 139.8 (quaternary carbon, carbon at 2'-site of aromatic ring), 124.3 (quaternary carbon, carbon at 2-site of propene), 123.7 (quaternary carbon, carbon at 1'-site of aromatic ring), 113.0 (CH, carbon at 6'-site of aromatic ring), 107.7 (CH, carbon at 3'-site of aromatic ring), 56.6 ($CH_3$, methyl group carbon of methoxy group), 56.0 ($CH_3$, methyl group carbon of methoxy group), 25.5 ($CH_2$, methylene group carbons at 3"- and 4"-sites of succinimidyl group), 13.8 ($CH_3$, methyl group carbon at 2-site of propene).

Synthesis of (E) 3-(2-amino-4,5-dimethoxyphenyl)-2-methyl-2-propenoic acid N-succinimide ester (4)

Into a mixed solvent of 70 ml of acetic acid and 5 ml of water, 8.3 g (22.8 mmol) of 3-(4,5-dimethoxy-2-nitrophenyl)-2-methyl-2-propenoic acid N-succinimidyl ester (3) were dissolved; and, with 5.0 g (89.5 mmol) of iron powder being added thereto, the mixture was heated to 70° C. After a reaction of 2 hours, insoluble matters were filtered out, and the filtrate was added to 500 ml of water. The resulting crystal was filtered out, washed with water, and dried, whereby 6.2 g of the aimed compound were obtained as a crystal (yield: 81%).

The structure of this compound was verified by $^1$H-NMR and $^{13}$C-NMR.

$^1$H-NMR (heavy dimethyl sulfoxide, δ ppm): 7.82 (1H, s, proton at 3-site of propene), 6.81 (1H, s, proton at 6'-site of aromatic ring), 6.44 (1H, s, proton at 3'-site of aromatic ring), 5.20 (2H, bs, aniline-type amino group proton), 3.73 (3H, s, methyl group proton of methoxy group), 3.67 (3H, s, methyl group proton of methoxy group), 2.85 (4H, s, methylene group proton of succinimidyl group), 2.16 (3H, s, methyl group proton at 2-site of propane).

$^{13}$C-NMR (DMSO-$d_6$, δ ppm): 170.4 (quaternary carbon, carbonyl carbon of succinimidyl group), 163.8 (quaternary carbon, carbonyl carbon at 1-site), 152.0 (quaternary carbon, carbon at 4'-site of aromatic ring), 144.5 (quaternary carbon, carbon at 2'-site of aromatic ring), 140.1 (CH, carbon at 3-site of propene), 140.0 (quaternary carbon, carbon at 5'-site of aromatic ring), 118.2 (quaternary carbon, carbon at 2-site of propene), 113.9 (CH, carbon at 6'-site of aromatic ring), 109.5 (quaternary carbon, carbon at 1'-site of aromatic ring), 99.8 (CH, carbon at 3'-site of aromatic ring), 56.3 ($CH_3$, methyl group carbon of methoxy group), 55.1 ($CH_3$, methyl group carbon of methoxy group), 25.4 ($CH_2$, methylene group carbons at 3"- and 4"-sites of succinimidyl group), 14.3 ($CH_3$, methyl group carbon at 2-site of propene).

Synthesis of (E) 3-(2-amino-4,5-dimethoxyphenyl)-2-methyl-2-propenoic acid phenethyl amide Into 20 ml of tetrahydrofuran, 0.33 g (1 mmol) of (E) 3-(2-amino-4,5-dimethoxyphenyl)-2-methyl-2-propenoic acid N-succinimide ester obtained above and 0.24 g (2 mmol) of 2-phenylethylamine (manufactured by Tokyo Kasei Kogyo Co., Ltd.) were dissolved; and the mixture was reacted at room temperature for 4 hours. The solution after the reaction was concentrated under a reduced pressure and then was dissolved in ethyl acetate. After the resulting solution was washed and was dried with magnesium sulfate anhydride, the solvent was eliminated under a reduced pressure, whereby a crude product was obtained. This product was refined by an aminopropyl-modified type silica gel column chromatography (n-hexane/ethyl acetate=1/1), whereby 0.34 g of the aimed compound was obtained (yield: quantitative).

The structure of this compound was verified by $^1$H-NMR and $^{13}$C-NMR.

$^1$H-NMR (heavy chloroform, δ ppm): 7.35–7.30 (2H, m, protons at 2"- and 6"-sites of phenethyl aromatic ring), 7.26–7.21 (4H, m, protons at 3-site of propene and at 3"-, 4"-, and 5"-sites of phenethyl aromatic ring), 6.60 (1H, s, proton at 6'-site of cinnamate aromatic ring), 6.29 (1H, s, proton at 3'-site of cinnamate aromatic ring), 5.93 (1H, bs, amino proton of amide group), 3.84 (3H, s, methyl group proton of methoxy group), 3.78 (3H, s, methyl group proton of methoxy group), 3.64 ppm (2H, dt, J=7 Hz, methylene group proton of phenethyl), 3.54 ppm (2H, s, amino group proton), 2.90 ppm (2H, t, J=7 Hz, methylene group proton of phenethyl), 1.96 ppm (3H, s, methyl group proton bound to 2-site of propene).

$^{13}$C-NMR (heavy chloroform, δ ppm): 169.1 (quaternary carbon, carbonyl carbon at 1-site), 150.2 (quaternary carbon, carbon at 4'-site of cinnamate aromatic ring), 141.6 (quaternary carbon, carbon at 2'-site of cinnamate aromatic ring), 139.2 (quaternary carbon, carbon at 5'-site of cinnamate aromatic ring), 139.0 (quaternary carbon, carbon at 1"-site of phenethyl aromatic ring), 131.7 (quaternary carbon, carbon at 2-site of propene), 130.3 (CH, carbon at 3-site of propene), 128.8 (CH, carbons at 2"- and 6"-sites of phenethyl aromatic ring), 128.7 (CH, carbons at 3"- and 5"-sites of phenethyl aromatic ring), 126.7 (CH, carbon at 4"-site of phenethyl aromatic ring), 113.7 (CH, carbon at 6'-site of cinnamate aromatic ring), 112.8 (quaternary carbon, carbon at 1'-site of cinnamate aromatic ring), 100.4 (CH, carbon at 3'-site of cinnamate aromatic ring), 56.7 ($CH_3$, methyl group carbon of methoxy group), 55.8 ($CH_3$, methyl group carbon of methoxy group), 41.0 ($CH_2$, methylene group carbon of phenethyl), 35.7 ($CH_2$, methylene group carbon of phenethyl), 14.3 ($CH_3$, methyl group carbon bound to 2-site of propene).

Synthesis of (E) N-L-glutamic acid 3-(2-amino-4,5-dimethoxyphenyl)-2-methyl-2-propenoic amide Into 40 ml of dimethylformamide, 0.5 g (1.5 mmol) of (E) 3-(2-amino-4,5-dimethoxyphenyl)-2-methyl-2-propenoic acid p-nitrophenyl ester was dissolved; and, with a solution of 2.3 g (10 mmol) of L-glutamic acid dissolved in 80 ml of a 0.5-N aqueous sodium hydrogencarbonate solution being added thereto, the mixture was reacted at room temperature for 4 hours. After its pH was adjusted to 4 with 2-N hydrochloric acid being added thereto, the reaction liquid was concentrated under a reduced pressure as it was. The resulting residue was once dissolved in 30 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.35 g of the aimed compound was obtained (yield: 63%).

The structure of this compound was verified by $^1$H-NMR and $^{13}$C-NMR.

$^1$H-NMR (heavy dimethyl sulfoxide, δ ppm): 8.44 (1H, d, J=7.5 Hz, amide group proton), 7.34 (1H, s, proton at 3-site of propenoic acid), 7.24 (1H, s, proton at 3'-site of aromatic ring), 6.94 (1H, s, proton at 6'-site of aromatic ring), 4.36 (1H, ddd, J=9.3 Hz, 7.7 Hz, 5.5 Hz, methine group proton at α-site of glutamic acid portion), 4.10 (2H, bs, amino group proton), 3.82 (6H, s, methyl group proton of methoxy group), 2.47 (2H, dd, J=7.5 Hz, 7.5 Hz, methylene group proton at γ-site of glutamic acid portion), 2.07 (2H, m, methylene group proton at β-site of glutamic acid portion), 1.97 (3H, s, methyl group proton bound to 2-site of propene)

$^{13}$C-NMR (heavy dimethyl sulfoxide, δ ppm): 169.3, 169.1, 169.0 (quaternary carbon, carbonyl carbon in glutamic acid portion and carbonyl carbon at 1-site), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, carbon at 3-site of propene), 122.6 (quaternary carbon, carbon at 1'-site of aromatic ring), 112.8 (CH, carbon at 6'-site of aromatic ring), 107.6 (CH, carbon at 3'-site of aromatic ring), 55.8 ($CH_3$, methyl group carbon of methoxy group), 55.7 ($CH_3$, methyl group carbon of methoxy group), 51.7 (CH, methine group carbon at α-site of glutamic acid portion), 30.3 ($CH_2$, methylene group carbon at γ-site of glutamic acid portion), 26.0 ($CH_2$, methylene group carbon at β-site of glutamic acid portion), 14.5 ($CH_3$, methyl group carbon bound to 2-site of propene).

Synthesis of (E) N-(o-di-t-butyloxy)-L-glutamic acid 3-(2-amino-4,5-dimethoxyphenyl)-2-methyl-2-propenoic amide Into 200 ml of tetrahydrofuran, 0.33 g (1.0 mmol) of (E) 3-(2-amino-4,5-dimethoxyphenyl)-2-methyl-2-propenoic acid N-succinimide ester and 0.89 g (3.0 mmol) of glutamic acid di-t-butyl ester hydrochloride (manufactured by Sigma Chemical Co.) were dissolved; and the mixture was reacted for 4 hours at room temperature. The solvent was eliminated under a reduced pressure, and the residue was dissolved in ethyl acetate. The resulting solution was washed, dried on sodium sulfate anhydride, and then concentrated, whereby a crude product was obtained. This product was refined by a column chromatography (silica gel (aminopropyl-modified type) manufactured by Fuji Silysia Chem. Co., NH-DM1020 1000 g; eluent: hexane/ethyl acetate=1/1), whereby 0.32 g of the aimed product was obtained (yield: 65%).

The structure of this compound was verified by $^1$H-NMR and $^{13}$C-NMR.

$^1$H-NMR (heavy chloroform, δ ppm): 7.34 (1H, s, proton at 3-site of propenoic acid), 6.75 (1H, d, J=7.3 Hz, amide group proton), 6.63 (1H, s, proton at 6'-site of aromatic ring), 6.30 (1H, s, proton at 3'-site of aromatic ring), 4.59 (1H, dt, J=7.3 Hz, 4.6 Hz, methine group proton at α-site of glutamic acid portion), 3.85 (3H, s, methyl group proton of methoxy group), 3.80 (3H, s, methyl group proton of methoxy group), 3.59 (2H, bs, amino group proton), 2.39 (2H, m, methylene group proton at γ-site of glutamic acid portion), 2.25 (2H, m, methylene group proton at β-site of glutamic acid portion), 2.05 (3H, s, methyl group proton at 2-site of propene), 1.50 (9H, s, methyl group proton of butyl group), 1.45 (9H, s, methyl group proton of butyl group).

$^{13}$C-NMR (heavy chloroform, δ ppm): 172.6 (quaternary carbon, carbonyl carbon in glutamic acid portion), 171.2 (carbonyl carbon in glutamic acid portion), 168.7 (quaternary carbon, carbonyl carbon at 1-site), 150.4 (quaternary carbon, carbon at 4'-site of aromatic ring), 141.6 (quaternary carbon, carbon at 2'-site of aromatic ring), 139.2 (quaternary carbon, carbon at 5'-site of aromatic ring), 131.1 (CH, carbon at 3-site of propene), 131.1 (quaternary carbon, carbon at 2-site of propene), 113.6 (CH, carbon at 6'-site of aromatic ring), 112.8 (CH, carbon at 1'-site of aromatic ring), 100.3 (CH, carbon at 3'-site of aromatic ring), 82.4 (quaternary carbon, butyl group carbon), 80.8 (quaternary carbon, butyl group carbon), 56.7 ($CH_3$, methyl group carbon of methoxy group), 55.8 ($CH_3$, methyl group carbon of methoxy group), 52.8 (CH, methine group carbon at α-site of glutamic acid portion), 31.7 ($CH_2$, methylene group proton at γ-site of glutamic acid portion), 28.1 ($CH_3$, methyl group carbon of butyl group), 27.5 ($CH_2$, methylene group proton at β-site of glutamic acid portion), 14.2 ($CH_3$, methyl group carbon at 2-site of propene).

Synthesis of 3-nitro-2-naphtaldehyde

The synthesis of 3-nitro-2-naphtaldehyde was carried out in conformity to a method described in literatures (Kienzle, Frank, Helv. Chim. Acta, 63 (8), 2364–2369 (1980); and Wani, Mansukh C., Ronman, Peter E., Lindley, James T., and Wall, Monroe E., J. Med. Chem. 1980, 23, 554–560).

The structure of this compound was verified by $^1$H-NMR and $^{13}$C-NMR.

$^1$H-NMR (heavy chloroform, δ ppm): 10.52 (1H, s, formyl group proton), 8.68 (1H, s, proton at 4-site), 8.47 (1H, s, proton at 1-site), 8.12–8.05 (2H, m, protons at 5- and 8-sites), 7.82–7.76 (2H, m, protons at 6- and 7-sites).

$^{13}$C-NMR (heavy chloroform, δ (ppm): 188.2 (CH, formyl group carbon), 159.4 (quaternary carbon, carbon at 2-site), 145.9 (quaternary carbon, carbon at 3-site), 134.2 (quaternary carbon, carbon at 4a-site), 133.7 (quaternary carbon, carbon at 8a-site), 132.1 (CH, carbon at 1-site), 130.6 (CH, carbon at 6- or 7-site), 130.5 (CH, carbon at 6- or 7-site), 129.8 (CH, carbon at 5- or 8-site), 129.6 (CH, carbon at 5- or 8-site), 126.0 (CH, carbon at 4-site).

Synthesis of 3-(2-nitro-benzo[d]phenyl)-2-methyl-2-propenoic acid ethyl ester

To 200 ml of benzene, 9.3 g (46 mmol) of 3-nitro-2-naphtaldehyde and 17.6 g (48.5 mmol) of Wittig reagent (carbethoxy ethylidene triphenylphosphorane) (manufactured by Aldrich Chemical Co., Inc.) were added, and the resulting mixture was stirred at room temperature for one night. After the completion of the reaction was verified by TLC, the reaction liquid was concentrated, whereby a crude product was obtained. This crude product was refined by a column chromatography (aminopropyl-modified silica gel (Fuji Silysia Chem. Co., NH-DM); developing solvent: hexane/ethyl acetate=1/1), whereby 13.0 g of the aimed compound were obtained as a crystal (yield: 96%).

The structure of this compound was verified by $^1$H-NMR and $^{13}$C-NMR.

$^1$H-NMR (heavy chloroform, δ ppm): 8.70 (1H, s, proton at 3'-site of aromatic ring), 8.03–8.00 (2H, m, protons at 4'- and 7'-sites of aromatic ring), 7.80 (1H, s, proton at 3-site of propene), 7.78 (1H, s, proton at 8'-site of aromatic ring), 7.74–7.63 (2H, m, protons at 5'- and 6'-sites of aromatic ring), 4.32 (2H, q, J=7 Hz, methylene group proton of ethyl group), 3.89 (2H, bs, NH$_2$), 2.00 (3H, s, methyl group proton bound to 2-site of propene), 1.37 (3H, t, J=7 Hz, methyl group proton of ethyl group).

$^{13}$C-NMR (heavy chloroform, δ ppm): 167.8 (quaternary carbon, carbonyl carbon at 1-site), 145.8 (quaternary carbon, carbon at 2'-site of aromatic ring), 135.7 (CH, carbon at 3-site of propene), 134.6 (quaternary carbon, carbon at 7a'-site of aromatic ring), 131.4 (quaternary carbon, carbon at 3a'-site of aromatic ring), 131.0 (CH, carbon at 8'-site of aromatic ring), 130.0 (quaternary carbon, carbon at 1'-site of aromatic ring), 129.9 (CH, carbon at 5'- or 6'-site of aromatic ring), 129.4 (CH, carbon at 5'- or 6'-site of aromatic ring), 128.3 (CH, carbon at 4'- or 7'-site of aromatic ring), 127.9 (CH, carbon at 4'- or 7'-site of aromatic ring), 127.7 (quaternary carbon, carbon at 2-site of propene), 125.8 (CH, carbon at 3'-site of aromatic ring), 61.1 (CH$_2$, methylene group carbon of ethyl group), 14.3 (CH$_3$, methyl group carbon of ethyl group), 14.0 (CH$_3$, carbon of methyl group bound to 2-site of propene).

Synthesis of 3-(2-nitro-benzo[d]phenyl)-2-methyl-2-propenoic acid

Into 130 ml of methanol, 5.48 g (19 mmol) of 3-(2-nitro-benzo[d]phenyl)-2-methyl-2-propenoic acid ethyl ester were dissolved; and, with 23 ml of a 2-N aqueous sodium hydroxide solution being added thereto, the resulting mixture was stirred at 40° C. for one night. After the completion of the reaction was confirmed by TLC, the reaction liquid was concentrated under a reduced pressure. The pH of the concentrated product was adjusted to 1 with 1-N hydrochloric acid being added thereto, and the precipitated crystal was filtered out. Thus obtained crystal was washed with water and a small amount of methanol, and was dried, whereby 4.8 g of the aimed compound were obtained as a crystal (yield: 98%).

The structure of this compound was verified by $^1$H-NMR and $^{13}$C-NMR.

$^1$H-NMR (heavy dimethyl sulfoxide, δ ppm): 8.90 (1H, s, proton at 3'-site of aromatic ring), 8.25–8.12 (2H, m, protons at 4'- and 7'-sites of aromatic ring), 8.08 (1H, s, proton at 3-site of propene), 7.85 (1H, s, proton at 8'-site of aromatic ring), 7.82–7.71 (2H, m, protons at 5'- and 6'-sites of aromatic ring), 1.93 (3H, s, methyl group proton bound to 2-site of propene).

$^{13}$C-NMR (heavy dimethyl sulfoxide, δ (ppm): 168.6 (quaternary carbon, carbonyl carbon at 1-site), 145.6 (quaternary carbon, carbon at 2 -site of aromatic ring), 134.9 (CH, carbon at 3-site of propene), 134.2 (quaternary carbon, carbon at 7a'-site of aromatic ring), 131.0 (CH, quaternary carbon, carbon at 8'-site of aromatic ring), 130.9 (quaternary carbon, carbon at 3a'-site of aromatic ring), 130.0 (CH, carbon at 5'- or 6'-site of aromatic ring), 129.9 (quaternary carbon, carbon at 1'-site of aromatic ring), 129.4 (CH, carbon at 5'- or 6'-site of aromatic ring), 128.3 (CH, carbon at 4'- or 7'-site of aromatic ring), 128.0 (CH, carbon at 4'- or 7'-site of aromatic ring), 126.8 (quaternary carbon, carbon at 2-site of propene), 125.6 (CH, carbon at 3'-site of aromatic ring), 13.7 (CH$_3$, carbon of methyl group bound to 2-site of propene).

Synthesis of (E) 3-(2-nitro-benzo[d]phenyl)-2-methyl-2-propenoic acid N-hydroxysuccinimide ester Into 90 ml of dichloromethane, 7.8 g (19 mmol) of 3-(2-nitro-benzo[d]phenyl)-2-methyl-2-propenoic acid and 3.28 g (28.5 mmol) of N-hydroxysuccinimide (manufactured by Wako Pure Chemical Industries, Ltd.) were dissolved; and 230 mg of dimethylaminopyridine (manufactured by Wako Pure Chemical Industries, Ltd.) were added thereto. While this solution was stirred under cooling with ice, 5.46 g (28.5 mmol) of 1-ethyl-3-(3-dimethylaminopropyl)-carbodiimide hydrochloride (EDC-HCl) (manufactured by Wako Pure Chemical Industries, Ltd.) were added thereto in portions. The liquid was returned to room temperature and stirred for one night. The resulting reaction liquid was concentrated under a reduced pressure, and thus concentrated product was dissolved in 100 ml of ethyl acetate. The resulting solution was washed and dried, and the solvent was evaporated. Thus obtained crude product was refined by a column chromatography (aminopropyl-modified silica gel (Fuji Sylisia Chem. Co., NH-DM); developing solvent: hexane/ethyl acetate=1/1), whereby 6.7 g of the aimed compound were obtained as a crystal (yield: 98%).

The structure of this compound was verified by $^1$H-NMR and $^{13}$C-NMR.

$^1$H-NMR (heavy methyl sulfoxide, δ ppm): 9.00 (1H, s, proton at 3'-site of aromatic ring), 8.30–8.14 (2H, m, protons at 4'- and 7'-sites of aromatic ring), 8.24 (1H, s, protons at 3-site of propene and at 8'-site of aromatic ring), 7.86–7.75 (2H, m, protons at 5'- and 6'-sites of aromatic ring), 2.89 (4H, s, methylene group proton of succinimidyl group), 2.10 (3H, s, methyl group proton bound to 2-site of propene).

$^{13}$C-NMR (heavy methyl sulfoxide, δ ppm): 170.2 (quaternary carbon, carbonyl carbon of succinimidyl group), 163.0 (quaternary carbon, carbonyl carbon at 1-site), 145.0 (quaternary carbon, carbon at 2'-site of aromatic ring), 134.2 (CH, carbon at 3-site of propene), 131.4 (CH, carbon at 8'-site of aromatic ring), 130.4 (CH, carbon at 5'- or 6'-site of aromatic ring), 129.7 (CH, carbon at 5'- or 6'-site of aromatic ring), 128.8 (CH, carbon at 4'- or 7'-site of aromatic ring), 128.2 (CH, carbon at 4'- or 7'-site of aromatic ring), 126.1 (CH, carbon at 3'-site of aromatic ring), 125.6 (quaternary carbon, carbon at 2'-site of propene), 25.5 (CH$_2$, methylene group carbon of succinimidyl group), 13.7 (CH$_3$, methyl group carbon bound to 2-site of propene).

Synthesis of (E) 3-(2-amino-benzo[d]phenyl)-2-methyl-2-propenoic acid N-hydroxysuccinimide ester Into a mixed solvent of 70 ml of acetic acid and 5 ml of water, 6.7 g (19 mmol) of 3-(2-nitro-benzo[d]phenyl)-2-methyl-2-propenoic acid N-hydroxysuccinimide ester were dissolved; and, with 4.7 g (89.5 mmol) of iron powder (manufactured by Koso Chem. Co.) being added thereto, the mixture was heated to 70° C. After a reaction of 1.5 hours, insoluble matters were filtered out, and the filtrate was added to 300 ml of water. The resulting mixture was twice extracted with 400 ml of ethyl acetate, and thus obtained solution was successively washed with water, an aqueous sodium hydrogencarbonate solution, and a saturated aqueous sodium chloride solution. The washed product was dried on sodium sulfate anhydride and concentrated, whereby 4.2 g of the aimed compound were obtained (yield: 66%).

The structure of this compound was verified by $^1$H-NMR.

$^1$H-NMR (heavy dimethyl sulfoxide, δ ppm): 7.94 (1H, s, proton at 3-site of propene), 7.77 (1H, s, proton at 8'-site of aromatic ring), 7.73–7.49 (2H, m, protons at 4'- and 7'-sites of aromatic ring), 7.36–7.12 (2H, m, protons at 5'- and 6'-sites of aromatic ring), 7.04 (1H, s, proton at 3'-site of aromatic ring), 3.30 (2H, amino group proton), 2.87 (4H, s, methylene proton of succinimidyl group), 2.18 (3H, s, methyl group proton bound to 2-site of propene).

Synthesis of 4-dimethylamino-2-nitrobenzaldehyde

In a nitrogen atmosphere, 51 g (0.33 mol) of phosphorus oxychloride (manufactured by Wako Pure Chemical Industries, Ltd.) were added dropwise to 88 ml of cooled dimethylformaldehyde (DMF). The dropping rate was adjusted so as to keep a temperature of 2° C. to 4° C. at the time of dropping, and stirring was further continued for 30 minutes at 2° C. after the completion of dropping. To this mixture, a 70-ml dimethylformamide solution of 54.8 g (0.33 mol) of N,N-dimethyl-3-nitroaniline (manufactured by Tokyo Kasei Kogyo Co., Ltd.) was added dropwise such that the reaction temperature does not exceed 5° C.; and the mixture was stirred for 2 hours as it was. Thereafter, temperature was gradually raised, and the mixture was stirred at 60° C. for one night. After being cooled to room temperature, the reaction liquid was poured into vigorously stirred 500 ml of ice water. The pH of the mixture was adjusted to about 8 with sodium acetate being added thereto, and the precipitated crystal was filtered out and dried, whereby 50.2 g of a crude product were obtained. This product was recrystallized from acetone/normal hexane, whereby 21 g of the aimed product were obtained (yield: 33%).

The structure of this compound was verified by $^1$H-NMR and $^{13}$C-NMR.

$^1$H-NMR (heavy chloroform, δ ppm): 10.12 (1H, s, formyl group proton), 7.91 (1H, d, J=9 Hz, proton at 6'-site of aromatic ring), 7.10 (1H, s, proton at 3'-site of aromatic ring), 6.85 (1H, d, J=9 Hz, proton at 5'-site of aromatic ring), 3.15 (6H, s, dimethylamino group proton).

$^{13}$C-NMR (heavy chloroform, δ ppm): 186.7 (CH, formyl group), 153.6 (quaternary carbon, carbon at 4-site), 152.7 (quaternary carbon, carbon at 2-site), 131.4 (CH, carbon at 6'-site of aromatic ring), 117.5 (quaternary carbon, carbon at 1-site), 114.3 (CH, carbon at 5'-site of aromatic ring), 105.8 (CH, carbon at 3'-site of aromatic ring), 40.4 (CH$_3$, methyl group carbon of dimethylamino group).

Synthesis of (E) ethyl $^3$-(4-dimethylamino-2-nitrophenyl)-2-methyl-2-propenate Into 250 ml of benzene, 20.0 g (0.10 mol) of 4-dimethylamino-2-nitrobenzaldehyde and 36.2 g (0.10 mol) of carbethoxyethylidene triphenylphosphorane (manufactured by Aldrich Chemical Co., Inc.) were dissolved, and the mixture was stirred at room temperature for one night. The solvent was evaporated under a reduced pressure, whereby 58 g of a crude product were obtained. This product was refined by a column chromatography (aminopropylated silica gel: Fuji Silysia Chem. Co., NH-DM1020), whereby 20.8 g of the aimed compound were obtained as a crystal (yield: 74.7%).

The structure of this compound was verified by $^1$H-NMR and $^{13}$C-NMR.

$^1$H-NMR (heavy chloroform, δ (ppm): 7.81 (1H, s, proton at 3-site of propenoic acid), 7.33 (1H, s, proton at 3'-site of aromatic ring), 7.23 (1H, d, J9 Hz, proton at 6'-site of aromatic ring), 6.86 (1H, d, J=9 Hz, proton at 5'-site of aromatic ring), 4.27 (2H, q, J=7 Hz, methylene group proton of ethyl group), 3.06 (6H, s, methyl group proton of dimethylamino group), 1.96 (3H, s, methyl group proton bound to 2-site of propene), 1.34 (3H, t, J=7 Hz, methyl group proton of ethyl group).

$^{13}$C-NMR (heavy chloroform, δ ppm): 168.2 (quaternary carbon, carbonyl carbon at 1-site), 150.2 (quaternary carbon, carbon at 2'-site of aromatic ring), 149.1 (quaternary carbon, carbon at 4'-site of aromatic ring), 135.7 (CH, carbon at 3-site of propenoic acid), 132.0 (CH, carbon at 6'-site of aromatic ring), 128.2 (quaternary carbon, carbon at 2-site of propene), 118.0 (quaternary carbon, carbon at 1'-site of aromatic ring), 115.7 (CH, carbon at 5'-site of aromatic ring), 107.0 (CH, carbon at 3'-site of aromatic ring), 60.8 (CH$_2$, methylene group carbon of ethyl group), 40.2 (CH$_3$, methyl group carbon of dimethylamino group), 14.3 (CH$_3$, methyl group carbon of ethyl group), 14.1 (CH$_3$, methyl group carbon bound to 2-site of propene).

Synthesis of (E) 3-(4-dimethylamino-2-nitrophenyl)-2-methyl-2-propenoic acid Into 150 ml of methanol, 15.0 g (53.9 mmol) of (E) ethyl 3-(4-dimethylamino-2-nitrophenyl)-2-methyl-2-propenate were dissolved; and, with 3.2 g (80 mmol) of sodium hydroxide being added thereto, the mixture was stirred at 45° C. for 5.5 hours. After the solvent was evaporated from the reaction liquid under a reduced pressure, the residue was dissolved in 100 ml of water. Thus obtained solution was adjusted to neutral with 2-N hydrochloric acid being added thereto. The precipitated crystal was filtered out, fully washed with water, and then dried, whereby 12.1 g of the aimed compound were obtained as a crystal (yield: 89.7%).

The structure of this compound was verified by $^1$H-NMR.

$^1$H-NMR (heavy chloroform, δ ppm): 7.93 (1H, s, proton at 3-site of propenoic acid), 7.33 (1H, d, J=9 Hz, proton at 6'-site of aromatic ring), 7.24 (1H, d, J=8 Hz, proton at 5'-site of aromatic ring), 6.87 (1H, s, proton at 3'-site of aromatic ring), 3.05 (6H, s, methyl group proton of dimethylamino group), 1.97 (3H, s, methyl group proton bound to 2-site of propene).

Synthesis of (E) ethyl 3-(2-amino-4-dimethylaminophenyl)-2-methyl-2-propenate In a dark room, 20.5 g (0.07 mol) of (E) ethyl 3-(4-dimethylamino-2-nitrophenyl)-2-methyl-2-propenate, 33.4 g (0.33 mol) of triethylamine (manufactured by Wako Pure Chemical Industries, Ltd.), and 2.1 g of 10% Pd/C were dissolved in 200 ml of acetonitrile, and 13.8 g (0.30 mol) of formic acid (manufactured by Wako Pure Chemical Industries, Ltd.) were added dropwise thereto at room temperature. Along with the dropping, the reaction temperature rose up to 45° C. After the completion of dropping, the reaction liquid was heated to 60° C. and was stirred for 1 hour. After the completion of the reaction was verified by TLC, the reaction liquid was cooled to room temperature, and insoluble matters were filtered out. The filtrate was concentrated under a reduced pressure and then was dissolved in 400 ml of ethyl acetate. The resulting solution was successively washed with water, a saturated aqueous sodium hydrogencarbonate solution, and a saturated aqueous sodium chloride solution; and was further dried with sodium sulfate anhydride. Thus dried product was concentrated under a reduced pressure, whereby 17.4 g of a crude product were obtained. This product was further recrystallized from normal hexane/ethyl acetate, whereby 4.67 g of the aimed compound were obtained (yield: 27%).

The structure of this compound was verified by $^1$H-NMR and $^{13}$C-NMR.

$^1$H-NMR (heavy chloroform, δ ppm): 7.60 (1H, s, proton at 3-site of propenoic acid), 7.08 (1H, d, J=9 Hz, proton at 6'-site of aromatic ring), 6.19 (1H, d, J=8 Hz, proton at 5'-site of aromatic ring), 6.01 (1H, s, proton at 3'-site of aromatic ring), 4.23 (2H, q, J=7Hz, methylene group proton of ethyl group), 3.74 (2H, bs, aniline-type amino group proton), 2.94 (6H, s, methyl group proton of dimethylamino group), 2.04 (3H, s, methyl group proton bound to 2-site of propene), 1.31 (3H, t, J=7 Hz, methyl group proton of ethyl group).

$^{13}$C-NMR (heavy chloroform, δ ppm): 169.1 (quaternary carbon, carbonyl carbon at 1-site), 151.7 (quaternary carbon, carbon at 2'-site of aromatic ring), 146.2 (quaternary carbon, carbon at 4'-site of aromatic ring), 134.7 (CH, carbon at 3-site of propenoic acid), 130.9 (CH, carbon at 6'-site of aromatic ring), 125.7 (quaternary carbon, carbon at 2-site of propene), 110.4 (quaternary carbon, carbon at 1'-site of aromatic ring), 103.3 (CH, carbon at 5'-site of aromatic ring), 98.5 (CH, carbon at 3'-site of aromatic ring), 60.5 (CH$_2$, methylene group carbon of ethyl group), 40.2 (CH$_3$, methyl group carbon of dimethylamino group), 14.4 (CH$_3$, methyl group carbon of ethyl group), 14.4 (CH$_3$, methyl group carbon bound to 2-site of propene).

Synthesis of (E) 3-(4-dimethylamino-2-nitrophenyl)-2-methyl-2-propenoic acid N-hydroxysuccinimide ester In a process similar to the above-mentioned condensation reaction between the acid derivative and N-hydroxysuccinimide ester, a condensation reaction between 3-(4-dimethylamino-2-nitrophenyl)-2-methyl-2-propenoic acid and N-hydroxysuccinimide was effected. Specifically, 3-(4-dimethylamino-2-nitrophenyl)-2-methyl-2-propenoic acid and N-hydroxysuccinimide (manufactured by Wako Pure Chemical Industries, Ltd.) were dissolved in dichloromethane, dimethylaminopyridine (manufactured by Wako Pure Chemical Industries, Ltd.) was added thereto, and 1-ethyl-3-(3-dimethylaminopropyl)-carbodiimide hydrochloride (EDC-HCl) (manufactured by Wako Pure Chemical Industries, Ltd.) was added thereto in portions while the mixture was stirred under cooling with ice. The liquid was returned to room temperature and then was stirred for one night. The reaction liquid was concentrated under a reduced pressure, and was dissolved in 100 ml of ethyl acetate. The ethyl acetate layer was washed and dried, the solvent was eliminated, and the resulting crude product was refined by a column chromatography (aminopropyl-modified silica gel (Fuji Silysia Chem. Co., NH-DM); developing solvent: hexane/ethyl acetate=1/1), whereby the aimed compound was obtained.

Synthesis of (E) 3-(2-amino-4-dimethylaminophenyl)-2-methyl-2-propenoic acid N-hydroxysuccinimide ester In a process similar to the above-mentioned reaction for reducing the aromatic nitro group into the amino group, a reaction for reducing the aromatic nitro group of 3-(4-dimethylamino-2-nitrophenyl)-2-methyl-2-propenoic acid N-hydroxysuccinimide ester was effected. Specifically, 3-(4-dimethylamino-2-nitrophenyl)-2-methyl-2-propenoic acid N-hydroxysuccinimide ester was dissolved in a mixed solvent of acetic acid and water; and, with iron powder (manufactured by Koso Chem. Co.) being added thereto, the mixture was heated to 70° C. After the reaction, insoluble matters were filtered out, and the filtrate was added to 300 ml of water. The resulting mixture was twice extracted with ethyl acetate, and thus obtained solution was successively washed with water, an aqueous sodium hydrogencarbonate solution, and a saturated aqueous sodium chloride solution. The washed product was dried on sodium sulfate anhydride and concentrated, whereby the aimed compound was obtained.

Synthesis of (E) 3-(4,5-dimethoxy-2-methylaminophenyl)-2-methyl-2-propenic acid phenethyl amide To a nonaqueous ether solution of 3.00 g (8.81 mmol) (E) 3-(2-amino-4,5-dimethoxyphenyl)-2-methyl-2-propenoic acid phenethyl amide and 1.34 ml (9.69 mmol) of triethylamine (manufactured by Wako Pure Chemical Industries, Ltd.), 0.92 ml (9.69 mmol) of dimethyl sulfate (manufactured by Wako Pure Chemical Industries, Ltd.) was slowly added dropwise. Thereafter, reflux was carried out for 2 hours at 34° C. to 35° C. After the completion of the reaction, the solvent was evaporated, and the resulting residue was dissolved in ethyl acetate. Thus obtained ethyl acetate layer was washed with water and was dried with sodium sulfate. The dried solution was concentrated under a reduced pressure, and the resulting crude product was refined by an aminopropyl-modified type silica gel column chromatography (n-hexane/ethyl acetate=1/1), whereby 1.12 g of the aimed compound was obtained as a yellowish crystal (yield: 35.9%).

The structure of this compound was verified by $^1$H-NMR and $^{13}$C-NMR.

$^1$H-NMR (heavy chloroform, δ ppm): 7.36–7.31 (2H, m, protons at 2"- and 6"-sites of phenethyl aromatic ring), 7.27–7.20 (4H, m, protons at 3-site of propene and at 3"-4"-, and 5"-sites of phenethyl aromatic ring), 6.65 (1H, s, proton at 6'-site of cinnamate aromatic ring), 6.27 (1H, s, proton at 3'-site of cinnamate aromatic ring), 5.91 (1H, bs, amino proton of amide group), 3.90 (3H, s, methyl group proton of methoxy group.), 3.79 (3H, s, methyl group proton of methoxy group), 3.64 ppm (2H, dt, J=7 Hz, methylene group proton of phenethyl), 2.90 ppm (2H, t, J=7 Hz, methylene group proton of phenethyl), 2.85 ppm (3H, s, methylene group proton of methylamino group), 1.95 ppm (3H, s, methyl group proton bound to 2-site of pentene).

$^{13}$C-NMR (heavy chloroform, δ ppm): 169.1 (quaternary carbon, carbonyl carbon at 1-site), 150.6 quaternary carbon, carbon at 4'-site of cinnamate aromatic ring), 142.6 (quaternary carbon, carbon at 2'-site of cinnamate aromatic ring), 140.1 (quaternary carbon, carbon at 5'-site of cinnamate aromatic ring), 138.9 (quaternary carbon, carbon at 1"-site of phenethyl aromatic ring), 131.5 (quaternary carbon, carbon at 2-site of propene), 130.3 (CH, carbon at 3-site of propene), 128.8 (CH, carbons at 2"- and 6"-sites of phenethyl aromatic ring), 128.7 (CH, carbons at 3"- and 5"-sites of phenethyl aromatic ring), 126.5 (CH, carbon at 4"-site of phenethyl aromatic ring), 114.6 (CH, carbon at 6'-site of cinnamate aromatic ring), 112.4 (quaternary carbon, carbon at 1'-site of cinnamate aromatic ring), 95.5 (quaternary carbon, carbon at 3'-site of cinnamate aromatic ring), 57.1 ($CH_3$, methyl group carbon of methoxy group), 55.8 ($CH_3$, methyl group carbon of methoxy group), 41.0 ($CH_2$, methylene group carbon of phenethyl), 35.6 ($CH_2$, methylene group carbon of phenethyl), 31.2 ($CH_3$, methyl group carbon of methylamino group), 14.2 ($CH_3$, methyl group carbon bound to 2-site of propene).

Synthesis of (E) 3-[4,5-dimethoxy-2-(trimethylsilylethoxycarbonyl)aminophenyl]-2-methyl-2-propenoic acid In a dark room, 12.2 g (46.2 mmol) of (E) ethyl 3-(2-amino-4,5-dimethoxyphenyl)-2-methyl-2-propenate were dissolved in 120 ml of acetonitrile; and, in a nitrogen atmosphere, 7.6 g (55.4 mmol) of pulverized potassium carbonate were added thereto while being cooled in ice bath. While this turbid reaction liquid was vigorously stirred, 10 g (55.4 mmol) of triethylsilylethoxycarbonyl chloride (Teoc-Cl) were slowly added dropwise thereto, and the mixture was stirred at room temperature for one night. The resulting reaction liquid was poured into 500 ml of cold water, and then was extracted with 300 ml of ethyl acetate. The extract was successively washed with water, an aqueous sodium hydrogencarbonate solution, and a saturated aqueous sodium chloride solution; and then was dried with sodium sulfate anhydride. Thereafter, the solvent was evaporated, whereby 13.5 g of a crude product were obtained. This crude product was refined by a silica gel column chromatography (eluent: normal hexane/ethyl acetate=3/1), whereby 7.0 g of (E) ethyl 3-[4,5-dimethoxy-2-(trimethylsilylethoxycarbonyl)aminophenyl]-2-methyl-2-propenate were obtained. This product was further dissolved in 30 ml of dioxane; and, with 25 ml of a 1-N aqueous sodium hydroxide solution being added thereto, the mixture was stirred at 40° C. The completion of the reaction was verified by TLC. To this reaction liquid, 150 ml of distilled water were added. After its pH was adjusted to 3 with 1-N hydrochloric acid, the precipitated crystal was filtered out and dried, whereby 5.6 g of the aimed compound were obtained (yield: 32%).

The structure of this compound was verified by $^1$H-NMR and $^{13}$C-NMR.

$^1$H-NMR (heavy chloroform, δ ppm): 8.81 (1H, bs, amide group proton), 7.56 (1H, s, proton at 3-site of propenoic acid), 6.97 (1H, s, proton at 3'-site of aromatic ring), 6.89 (1H, s, proton at 6'-site of aromatic ring), 4.12 (2H, t, J=8 Hz, methylene group proton at α-site of trimethylsilylethoxy group), 3.77 (6H, s, methyl group proton of methoxy group), 1.94 (3H, s, methyl group proton bound to 2-site of propenoic acid), 0.94 (2H, t, J=8 Hz, methylene group proton at β-site of trimethylsilylethoxy group), 0.03 (9H, s, methyl group proton of trimethylsilylethoxy group).

$^{13}$C-NMR (heavy chloroform, δ ppm): 169.4 (quaternary carbon, carbonyl group carbon at 1-site of propenoic acid), 154.6 (quaternary carbon, carbonyl carbon of trimethylsilylethoxycarbonyl group), 148.7 (quaternary carbon, carbon at 4'-site of aromatic ring), 145.7 (quaternary carbon, carbon at 5'-site of aromatic ring), 134.9 (CH, carbon at 3-site of propenoic acid), 130.3 (quaternary carbon, carbon at 2'-site of aromatic ring), 127.8 (quaternary carbon, carbon at 2-site of propenoic acid), 112.3 (CH, carbon at 6'-site of aromatic ring), 62.1 ($CH_2$, methylene group carbon at β-site of trimethylsilylethoxy group), 55.7 ($CH_3$, methyl group carbon of methoxy group), 55.5 ($CH_3$, methyl group carbon of methoxy group), 17.3 ($CH_2$, methylene group carbon at α-site of trimethylsilylethoxy group), 14.0 ($CH_3$, methyl group carbon bound to 2-site of propenoic acid), −1.5 ($CH_3$, methyl group carbon of trimethylsilylethoxy group).

Synthesis of (E) 3-[4,5-dimethoxy-2-(trimethylsilylethoxycarbonyl)aminophenyl]-2-methyl-2-propenoic acid N-hydroxysuccinimide ester In a dark room, 9.0 g (23.6 mmol) of (E) 3-[4,5-dimethoxy-2-(trimethylsilylethoxycarbonyl)aminophenyl]-2-methyl-2-propenoic acid and 2.71 g (23.6 mmol) of N-hydroxysuccinimide (manufactured by Wako Pure Chemical Industries, Ltd.) were dissolved in 120 ml of dimethylformamide; and, with 5.36 g (26.0 mmol) of N,N'-dicyclohexyl carbodiimide (DCC) (manufactured by Wako Pure Chemical Industries, Ltd.) being added thereto, the mixture was stirred for one night at room temperature. After the completion of the reaction, precipitated dicyclohexyl urea was filtered out, and the solvent was evaporated from the resulting filtrate under a reduced pressure, whereby 18 g of a crude product were obtained. This crude product was refined by a silica gel column chromatography (moving phase: normal hexane/ethyl acetate=1/1), whereby 6.98 g of the aimed compound were obtained (yield: 61.8%).

The structure of this compound was verified by $^1$H-NMR and $^{13}$C-NMR.

$^1$H-NMR (heavy chloroform, δ ppm): 7.81 (1H, s, proton at 3-site of propenoic acid), 7.54 (1H, s, proton at 3'-site of aromatic ring), 6.73 (1H, s, proton at 6'-site of aromatic ring), 4.23 (2H, t, J=7 Hz, methylene group proton at α-site of trimethylsilylethoxy group), 3.90 (3H, s, methyl group proton of methoxy group), 3.83 (3H, s, methyl group proton of methoxy group), 2.87 (4H, s, methylene group proton of succinimidyl group), 2.09 (3H, s, methyl group proton bound to 2-site of propenoic acid), 1.04 (2H, t, J=7 Hz, methylene group proton at β-site of trimethylsilylethoxy group), 0.03 (9H, s, methyl group proton of trimethylsilylethoxy group).

$^{13}$C-NMR (heavy chloroform, δ ppm): 169.4 (quaternary carbon, carbonyl carbon at 1-site of propenoic acid), 163.1 (quaternary carbon, carbonyl carbon of succinimidyl group), 154.0 (quaternary carbon, carbonyl carbon of trimethylsilylethoxycarbonyl group), 150.5 (quaternary carbon, carbon at 4'-site of aromatic ring), 145.1 (quaternary carbon, carbon at 5'-site of aromatic ring), 139.3 (CH, carbon at 3-site of propenoic acid), 130.6 (quaternary carbon, carbon at 2'-site of aromatic ring), 125.0 (quaternary carbon, carbon at 2-site of propenoic acid), 117.0 (quaternary carbon, carbon at 1'-site of aromatic ring), 111.0 (CH, carbon at 6'-site of aromatic ring), 105.6 (CH, carbon at 3'-site of aromatic ring), 63.8 ($CH_2$, methyl group carbon at β-site of trimethylsilylethoxy group), 56.2 ($CH_3$, methyl group carbon of methoxy group), 56.0 ($CH_3$, methyl group carbon of methoxy group), 25.6 ($CH_2$, methylene group carbon of succinimidyl group), 17.7 ($CH_2$, methylene group carbon at α-site of trimethylsilylethoxy group), 14.4 ($CH_3$, methyl group carbon bound to 2-site of propenoic acid), −1.5 ($CH_3$, methyl group carbon of trimethylsilylethoxy group)

Synthesis of (E) N-L-glutamic acid 3-(2-amino-4,5-dimethoxyphenyl)-2-methyl-2-propenoic amide disodium salt by reaction between (E) 3-[4,5-dimethoxy-2-(trimethylsilylethoxycarbonyl) aminophenyl]-2-methyl-2-propenoic acid N-hydroxysuccinimide ester and L-glutamic acid In a dark room, 5 ml of a 2.4-mM, 9.5-pH buffer solution (40-mM lithium carbonate/hydrochloric acid buffer solution) of L-glutamic acid (manufactured by Wako Pure Chemical Industries, Ltd.) were added to 5 ml of a 2-mM dimethylformamide solution of (E) 3-[4,5-dimethoxy-2-(trimethylsilylethoxycarbonyl)aminophenyl]-2-methyl-2-propenoic acid N-hydroxysuccinimide ester, and the resulting mixture was stirred. Using a high-performance liquid chromatography (moving phase: 0.05% trifluoroacetic acid acetonitrile/water=10/90 to 60/40 (20 minutes); reactant: 13.5 minutes; coupling product: 8.1 minutes), it was verified that the reaction had been completed in 3 hours, and that only (E) N-L-glutamic acid 3-[2-amino-4,5-dimethoxy-2-(trimethylsilylethoxycarbonyl)aminophenyl]-2-methyl-2-propenoic amide had been generated. The resulting solution was concentrated under a reduced pressure, and then was dissolved in 4.5 ml of dichloromethane. With 1 ml of trifluoroacetic acid being added thereto, the solution was stirred at 30° C. for 24 hours. This reaction solution was separated and analyzed by use of a high-performance liquid chromatography (moving phase: 0.05% trifluoroacetic acid acetonitrile/water=10/90 to 60/40 (20 minutes); de-protecting reaction product: 6.0 minutes), whereby it was verified that the de-protecting reaction had been completed, and that only (E) N-L-glutamic acid 3-(2-amino-4,5-dimethoxyphenyl)-2-methyl-2-propenoic amide had been generated (reaction being quantitative).

The structure of (E) N-L-glutamic acid 3-[2-amino-4,5-dimethoxy-2-(trimethylsilylethoxycarnonyl)aminophenyl]-2-methyl-2-propenoic amide was verified by $^1$H-NMR and $^{13}$C-NMR.

$^1$H-NMR (heavy water, δ ppm): 7.18 (1H, s, methine group proton at 3-site of propenoic acid), 7.07 (1H, s, proton at 3'-site of aromatic ring), 7.00 (1H, s, proton at 6'-site of aromatic ring), 4.24 (3H, m, methine group proton at α-site of glutamic acid portion, and methylene group proton at α-site of trimethylsilylethoxycarbonyl group), 3.86 (6H, s, methyl group proton of methoxy group), 2.27 (2H, dd, J=9 Hz, 8 Hz, methylene group proton at γ-site of glutamic acid portion), 2.16–2.09 (2H, m, methylene group proton at β-site of glutamic acid portion), 1.93 (3H, s, methyl group proton bound to 2-site of propenoic acid), 0.99 (2H, t, J=7 Hz, methylene group proton at β-site of trimethylsilylethoxycarbonyl group), 0.03 (9H, s, methyl group proton of trimethylsilyl group)

$^{13}$C-NMR (heavy water, δ ppm): 183.0 (quaternary carbon, carbonyl carbon in glutamic acid portion), 179.4 (quaternary carbon, carbonyl carbon in glutamic acid portion), 172.2 (quaternary carbon, carbonyl carbon at 1-site of propenoic acid portion), 158.3 (quaternary carbon, carbonyl carbon of trimethylsilylethoxycarbonyl group), 149.0 (quaternary carbon, carbon at 4'-site of aromatic ring), 146.2 (quaternary carbon, carbon at 5'-site of aromatic ring), 131.8 (CH, methine group carbon at 3-site of propenoic acid), 129.2 (quaternary carbon, carbon at 2'-site of aromatic ring), 126.9 (quaternary carbon, carbon at 2-site of propenoic acid portion), 114.7 (quaternary carbon, carbon at 1'-site of aromatic ring), 113.3 (CH, carbon at 6'-site of aromatic ring), 103.0 (CH, carbon at 3'-site of aromatic ring), 65.5 (CH$_2$, methylene group carbon at β-site of trimethylsilylethoxycarbonyl group), 56.7 (CH, methine group carbon at α-site of glutamic acid portion), 56.6 (CH$_3$, methyl group carbon of methoxy group), 35.1 (CH$_2$, methylene group carbon at γ-site of glutamic acid portion), 29.4 (CH$_2$, methylene group carbon at β-site of glutamic acid portion), 17.7 (CH$_2$, methylene group carbon at α-site of triethylsilylethoxycarbonyl group), 14.2 (CH$_3$, methyl group carbon bound to 2-site of propenoic acid portion), -1.5 (CH$_3$, methyl group carbon of trimethylsilyl group).

The structure of (E) N-L-glutamic acid 3-(2-amino-4,5-dimethoxy-2-dimethoxyphenyl)-2-methyl-2-propenoic amide di-sodium salt was verified by $^1$H-NMR and $^{13}$C-NMR.

$^1$H-NMR (heavy dimethyl sulfoxide, δ ppm): 8.44 (1H, bs, amide group proton), 7.34 (1H, s, methine group proton at 3-site of propenoic acid), 7.24 (1H, s, proton at 3'-site of aromatic ring), 6.94 (1H, s, proton at 6'-site of aromatic ring), 4.36 (1H, dd, J=9 Hz, J=8 Hz, methine group proton at α-site of glutamic acid portion), 4.10 (2H, bs, amino group proton), 3.82 (6H, s, methyl group proton of methoxy group), 2.47 (2H, t, J=8 Hz, methine group proton at γ-site of glutamic acid portion), 2.07 (2H, m, methine group proton at β-site of glutamic acid portion), 1.97 (3H, s, methyl group proton bound to 2-site of propenoic acid.

$^{13}$C-NMR (heavy dimethyl sulfoxide, δ ppm): 169.3, 169.1, 169.0 (quaternary carbon, carbonyl carbon in glutamic acid portion, and carbonyl carbon at 1-site of propenoic acid portion), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, methine group carbon at 3-site of propenoic acid), 122.6 (quaternary carbon, carbon at 1'-site of aromatic ring), 117.4 (quaternary carbon, carbon at 1'-site of aromatic ring), 112.8 (CH, carbon at 6'-site of aromatic ring), 107.6 (CH, carbon at 3'-site of aromatic ring), 55.8 (CH$_3$, methyl group carbon of methoxy group), 55.7 (CH$_3$, methyl group carbon of methoxy group), 51.7 (CH, methine group carbon at α-site of glutamic acid portion), 30.3 (CH$_2$, methylene group carbon at γ-site of glutamine portion), 26.0 (CH$_2$, methylene group carbon at β-site of glutamic acid portion), 14.5 (CH$_3$, methyl group carbon bound to 2-site of propenoic acid portion).

Synthesis of (E) N-(N-methyl)-D-aspartic acid 3-(2-amino-4,5-dimethoxyphenyl)-2-methyl-2-propenoic amide by reaction between (E) 3-[4,5-dimethoxy-2-(trimethylsilylethoxycarbonyl)aminophenyl]-2-methyl-2-propenoic acid N-hydroxysuccinimide ester and N-methyl-D-aspartic acid In a dark room, 5 ml of a 2.4-mM, 9.5-pH buffer solution (40-mM lithium carbonate/hydrochloric acid buffer solution) of N-methyl-D-aspartic acid (manufactured by Wako Pure Chemical Industries, Ltd.) were added to 5 ml of a 2-mM dimethylformamide solution of (E) 3-[4,5-dimethoxy-2-(trimethylsilylethoxycarbonyl)aminophenyl]-2-methyl-2-propenoic acid N-hydroxysuccinimide ester, and the resulting mixture was stirred. The progress of this reaction was observed by use of a high-performance liquid chromatography (moving phase: 0.05% trifluoroacetic acid acetonitrile/water=10/90 to 60/40 (20 minutes); reactant: 13.5 minutes; coupling product: 10.1 minutes), whereby it was verified that the reaction had been completed in 5 hours, and that only (E) N-(N-methyl)-L-aspartic acid 3-[2-amino-4,5-dimethoxy-2-(trimethylsilylethoxycarbonyl) aminophenyl]-2-methyl-2-propenoic amide had been generated. The resulting solution was concentrated under a reduced pressure, and then was dissolved in 4.5 ml of dichloromethane. With 1 ml of trifluoroacetic acid being added thereto, the solution was stirred at 30° C. for 24 hours. The progress of this reaction was observed by use of a high-performance liquid chromatography (moving phase: 0.05% trifluroacetic acid acetonitrile/water=10/90 to 60/40 (20 minutes); de-protecting reaction product: 8.7 minutes), whereby it was verified that the de-protecting reaction had been completed, and that only (E) N-(N-methyl)-D-aspartic acid 3-(2-amino-4,5-dimethoxyphenyl)-2-methyl-2-propenoic amide had been generated (reaction being quantitative).

The structure of (E) N-(N-methyl)-D-aspartic acid 3-(2-amino-4,5-dimethoxyphenyl)-2-methyl-2-propenoic amide was verified by $^1$H-NMR and $^{13}$C-NMR.

$^1$H-NMR (heavy water, δ ppm): 6.85 (1H, s, proton at 6'-site of aromatic ring), 6.61 (1H, s, proton at 3'-site of aromatic ring), 6.48 (1H, s, methine group proton at 3-site of propenoic acid), 5.02 (1H, dd, J=9 Hz, J=6 Hz, methine group proton at α-site of aspartic acid portion), 3.83 (3H, s, methyl group proton of methoxy group), 3.81 (3H, s, methyl group proton of methoxy group), 3.20–2.79 (2H, m, methylene group proton at α-site of aspartic acid portion), 2.90 (3H, s, methyl group proton bound to nitrogen in aspartic acid portion), 1.96 (3H, s, methyl group proton bound to 2-site of propenoic acid)

$^{13}$C-NMR (heavy water, δ ppm): 177.2 (quaternary carbon, carbonyl carbon in aspartic acid portion), 176.3 (quaternary carbon, carbonyl carbon in aspartic acid portion), 174.7 (quaternary carbon, carbonyl carbon at 1-site of propenoic acid), 149.8 (quaternary carbon, carbon at 4'-site of aromatic ring), 141.9 (quaternary carbon, carbon at 2'-site of aromatic ring), 139.4 (quaternary carbon, carbon at 5'-site of aromatic ring), 134.2 (quaternary carbon, carbon at 2-site of propenoic acid), 126.9 (CH, methine group carbon at 3-site of propenoic acid), 114.9 (quaternary carbon, carbon at 1'-site of aromatic ring), 114.6 (CH, carbon at 6'-site of aromatic ring), 102.5 (CH, carbon at 3'-site of aromatic ring), 62.1 (CH, methine carbon at α-site of aspartic acid portion), 57.4 (CH$_3$, methyl group carbon of methoxy group), 56.4 (CH$_3$, methyl group carbon of methoxy group), 36.0 (CH$_2$, methylene group carbon at β-site of aspartic acid portion), 30.3 (CH$_3$, methyl group carbon bound to nitrogen in aspartic acid portion), 15.8 (CH$_3$, methyl group carbon bound to 2-site of propenoic acid).

Synthesis of (E) 3-[4-dimethylamino-2-(tert-butyloxycarbonyl)]-2-methyl-2-propenoic acid N-hydroxysuccinimide ester In a dark room, 1.4 g (5.65 mmol) of (E) ethyl 3-(2-amino-4-dimethylaminophenyl)-2-methyl-2-propenate were dissolved in 14 ml of dried tetrahydrofuran; and, with 1.4 g (6.21 mmol) of di-tert-butyl dicarbonate (manufactured by Kokusan Chemical Works) being added thereto, the mixture was refluxed for one night. After the completion of the reaction, the reaction liquid was concentrated under a reduced pressure, and was refined by a silica gel column chromatography (aminopropylated silica gel: Fuji Silysia Chem. Co., NH-DM1020; eluting solvent: ethyl acetate/normal hexane=2/1), whereby 1.5 g of (E) ethyl 3-[4-dimethylamino-2-(tert-butyloxycarbonyl)amino-phenyl]-2-methyl-2-propenate were obtained. This product was dissolved in 19 ml of dioxane; and, with 8.2 ml of a 2-N aqueous sodium hydroxide solution being added thereto, the mixture was stirred for one night at 40° C. The reaction liquid was extracted with methyl-tert-butyl ether. The pH of the resulting water layer was adjusted to about 1 with 2-N hydrochloric acid. The precipitated crystal was filtered out, washed with water, and then dried under a reduced pressure, whereby 1.0 g of (E) 3-[4-dimethylamino-2-(tert-butyloxycarbonyl)amino-phenyl]-2-methyl-2-propenoic acid was obtained. This product was then dissolved in 13 ml of dried dimethylformamide; and, with 361 mg (3.44 mmol) of hydroxysuccinimide (manufactured by Wako Pure Chemical Industries, Ltd.) and 708 mg (3.44 mmol) of N,N'-dicyclohexylcarbodiimide (DCC) (manufactured by Wako Pure Chemical Industries, Ltd.) being added thereto under cooling with ice, the mixture was stirred at room temperature for one night. After the completion of the reaction, precipitated dicyclohexyl urea was filtered out, and the solvent was evaporated under a reduced pressure, whereby a crude product was obtained. This product was refined by recrystallization from isopropyl ether, whereby 1.0 g of the aimed compound was obtained (yield: 43%).

The structure of this compound was verified by $^1$H-NMR and $^{13}$C-NMR.

$^1$H-NMR (heavy chloroform, δ ppm): 7.84 (1H, s, proton at 3-site of propenoic acid portion), 7.34 (1H, bs, amide group proton), 7.20 (1H, d, J=9 Hz, proton at 6'-site of aromatic ring in aminocinnamoyl portion), 6.45 (1H, d, J=9 Hz, proton at 5'-site of aromatic ring in aminocinnamoyl portion), 6.43 (1H, s, proton at 3'-site of aromatic ring in aminocinnamoyl portion), 3.03 (6H, s, methyl group proton of dimethylamino group NMe2), 2.88 (4H, s, methylene group proton of succinimide group), 2.16 (3H, s, methyl group proton bound to 2-site of propene), 1.52 (9H, s, methyl group proton of butyloxycarbonyl group).

$^{13}$C-NMR (heavy chloroform, δ ppm): 169.6 (quaternary carbon, carbonyl group carbon of succinimide group), 163.7 (quaternary carbon, carbonyl group carbon at 1-site of propene), 152.7 (quaternary carbon, carbonyl group carbon of butyloxycarbonyl group), 151.9 (quaternary carbon, carbon at 4'-site of aromatic ring in aminocinnamoyl portion), 139.7 (CH, carbon at 3-site of propenoic acid), 138.5 (quaternary carbon, carbon at 2'-site of aromatic ring in aminocinnamoyl portion), 130.9 (CH, carbon at 6'-site of aromatic ring in aminocinnamoyl portion), 121.1 (quaternary carbon, carbon at 2-site of propenoic acid), 112.7 (quaternary carbon, carbon at 1'-site of aromatic ring in aminocinnamoyl portion), 107.0 (CH, carbon at 5'-site of aromatic ring in aminocinnamoyl portion), 103.9 (CH, carbon at 3'-site of aromatic ring in aminocinnamoyl portion), 80.8 (quaternary carbon, center carbon of butyloxycarbonyl group), 40.1 (CH$_3$, methyl group carbon of dimethylamino group), 28.3 (CH$_3$, methyl group carbon of butyloxycarbonyl group), 25.6 (CH$_2$, methylene group carbon of succinimide group), 14.5 (CH$_3$, methyl group carbon bound to 2-site of propene).

Synthesis of (E) 3-[4-dimethylamino-2-(trimethylsilylethoxycarbonyl)amino-phenyl]-2-methyl-2-propenic acid N-hydroxysuccinimide ester In a dark room, 500 mg (2.02 mmol) of (E) ethyl 3-(2-amino-4-dimethylaminophenyl)-2-methyl-2-propenate were dissolved in dried methylene chloride; and, with 553 mg (2.22 mmol) of trimethylsilylethoxycarbonyl-succinnimidyl ester being added thereto, the mixture was reacted for 48 hours at room temperature. Thereafter, the reaction liquid was concentrated under a reduced pressure and was dissolved in ethyl acetate. The resulting organic layer was successively washed with water and a saturated aqueous sodium chloride solution. Thus obtained crude product was refined by a silica gel column chromatography (aminopropylated silica gel: Fuji Silysia Chem. Co., NH-DM1020; eluting solvent: ethyl acetate/normal hexane=1/1), whereby 105 mg of (E) ethyl 3-[4-dimethylamino-2-(trimethylsilylethoxycarbonyl)amino-phenyl]-2-methyl-2-propenate were obtained. This product was dissolved in 5 ml of tetrahydrofuran; and, with 5 ml of a 1-N aqueous sodium hydroxide solution being added thereto, the mixture was stirred for 2 hours at 40° C. The reaction liquid was concentrated under a reduced pressure, and then was applied to a column using a solid-phase extraction filler DIAION HP-21 (manufactured by Mitsubishi Chemical Corp.), so as to be desalted as being eluted with water. Subsequently, it was eluted with a 10% aqueous methanol solution. The resulting eluate was lyophilized, whereby 90 mg of (E) 3-[4-dimethylamino-2-(trimethylsilylethoxycarbonyl) amino-phenyl]-2-methyl-2-propenic acid sodium salt were obtained. This product was subsequently dissolved in 5 ml of dried dimethylformamide; and, with 31 ml of hydroxysuccinimide (manufactured by Wako Pure Chemical Industries, Ltd.), 65 mg (0.3 mmol) of N,N'-dicyclohexylcarbodiimide (DCC) (manufactured by Wako Pure Chemical Industries, Ltd.), a catalytic amount of dimethylaminopyridine (manufactured by Wako Pure Chemical Industries, Ltd.) being added thereto, the mixture was stirred at room temperature for one night. After the completion of the reaction, precipitated dicyclohexyl urea was filtered out, and the solvent was evaporated from the resulting filtrate under a reduced pressure, whereby a crude product was obtained. This product was refined by a silica gel column chromatography (aminopropylated silica gel: Fuji Silysia Chem. Co., NH-DM1020; eluting solvent: ethyl acetate/ normal hexane=1/2), whereby 32 mg of the aimed product were obtained (yield: 3.4%).

The structure of this compound was verified by $^1$H-NMR and $^{13}$C-NMR.

$^1$H-NMR (heavy chloroform, δ ppm): 7.82 (1H, s, proton at 3-site of propenoic acid portion), 7.19 (1H, d, J=8 Hz, proton at 6'-site of aromatic ring in aminocinnamoyl portion), 6.46 (1H, d, J=8 Hz, proton at 5'-site of aromatic ring in aminocinnamoyl portion), 6.41 (1H, s, proton at 3'-site of aromatic ring in aminocinnamoyl portion), 4.10 (2H, t, J=7 Hz, methylene proton at α-site of trimethylsilylethoxy group), 3.01 (6H, s, methyl group proton of dimethylamino group NMe2), 2.86 (4H, s, methylene group proton of succinimide group), 2.10 (3H, s, methyl group proton bound to 2-site of propene), 1.04 (2H, t, J=7 Hz, methylene group proton at β-site of trimethylsilylethoxy group), 0.03 (9H, s, methyl group proton of trimethylsilylethoxy group).

$^{13}$C-NMR (heavy chloroform, δ ppm): 169.4 (quaternary carbon, carbonyl group carbon of succinimide group), 169.3 (quaternary carbon, carbonyl group carbon at 1-site of propene), 152.6 (quaternary carbon, carbonyl carbon of trimethylsilylethoxycarbonyl group), 151.9 (quaternary carbon, carbon at 4'-site of aromatic ring in aminocinnamoyl portion), 139.8 (CH, carbon at 3-site of propenoic acid), 138.4 (quaternary carbon, carbon at 2'-site of aromatic ring in aminocinnamoyl portion), 131.0 (CH, carbon at 6'-site of aromatic ring in aminocinnamoyl portion), 121.0 (quaternary carbon, carbon at 2-site of propenoic acid), 112.4 (quaternary carbon, carbon at 1'-site of aromatic ring in aminocinnamoyl portion), 107.3 (CH, carbon at 5'-site of aromatic ring in aminocinnamoyl portion), 103.9 (CH, carbon at 3'-site of aromatic ring in aminocinnamoyl portion), 63.8 (CH$_2$, methyl group carbon at β-site of trimethylsilylethoxy group), 40.1 (CH$_3$, methyl group carbon of dimethylamino group), 25.6 (CH$_2$, methylene group carbon of succinimidyl group), 17.6 (CH$_2$, methylene group carbon at α-site of trimethylsilylethoxy group), 14.5 (CH$_3$, methyl group carbon bound to 2-site of propenoic acid), −1.5 (CH$_3$, methyl group carbon of trimethylsilylethoxy group).

Synthesis of 3-(2-amino-4,5-dimethoxyphenyl)-2-methyl-2-propenoic acid ethyl ester Into 250 ml of glacial acetic acid, 19.0 g of 3-(4,5-dimethoxy-2-nitrophenyl)-2-methyl-2-propenoic acid ethyl ester were dissolved; and, with 15.0 g of iron powder and 20 ml of ion-exchanged water being added thereto, the mixture was refluxed under heating for 40 minutes. The resulting reaction liquid was filtered out, the filtrate was concentrated under a reduced pressure, and thus obtained residue was dissolved in ethyl acetate. The resulting solution was successively washed with water, a 5% aqueous sodium hydrogencarbonate solution, and a saturated aqueous sodium chloride solution. After this ethyl acetate solution was left on sodium sulfate anhydride for one night so as to be dried, ethyl acetate was evaporated under a reduced pressure, and the resulting residue was recrystallized from a mixed liquid of hexane/ethanol, whereby 12.5 g of the aimed product were obtained (yield: 78%).

The structure of this compound was verified by $^1$H-NMR and $^{13}$C-NMR.

$^1$H-NMR (heavy chloroform, δ ppm): 7.57 (1H, s, proton at 3-site of propenoic acid), 6.68 (1H, s, proton at 6'-site of aromatic ring), 6.29 (1H, s, proton at 3'-site of aromatic ring), 4.25 (2H, q, J=7 Hz, methylene group proton of ethyl group), 3.84 (3H, s, methyl group proton of methoxy group), 3.79 (3H, s, methyl group proton of methoxy group), 3.57 (2H, bs, amino group proton), 2.03 (3H, s, methyl group proton at 2-site of propene), 1.33 (3H, t, J=7 Hz, methyl group proton of ethyl group) $^{13}$C-NMR (heavy chloroform, δ ppm): 168.6 (quaternary carbon, carbonyl carbon at 1-site), 150.6 (quaternary carbon, carbon at 4'-site of aromatic ring), 141.6 (quaternary carbon, carbon at 2'-site of aromatic ring), 139.6 (quaternary carbon, carbon at 5'-site of aromatic ring), 134.6 (CH, carbon at 3-site of propene), 128.2 (quaternary carbon, carbon at 2-site of propene), 113.5 (CH, carbon at 6'-site of aromatic ring), 112.7 (quaternary carbon, carbon at 1'-site of aromatic ring), 100.3 (quaternary carbon, carbon at 3'-site of aromatic ring), 60.8 (CH$_2$, methylene group carbon of ethyl group), 56.7 (CH$_3$, methyl group carbon of methoxy group), 55.8 (CH$_3$, methyl group carbon of methoxy group), 14.4 (CH$_3$, methyl group carbon of ethyl group), 14.3 (CH$_3$, methyl group carbon at 2-site of propene).

Synthesis of (E) 3-(2-amino-4,5-dimethoxyphenyl)-2-methyl-2-propenoic acid

Into 10 ml of tetrahydrofuran (THF), 1.0 g of (E) 3-(2-amino-4,5-dimethoxyphenyl)-2-methyl-2-propenoic acid ethyl ester was dissolved; and, with 10 ml of a 1-N aqueous sodium hydroxide solution being added thereto, the mixture was reacted at 40° C. for 4 hours. After the completion of the reaction, the mixture was cooled with 10 ml of 1-N hydrochloric acid being added thereto, and the precipitated crystal was filtered out, whereby 0.85 g of the aimed compound was obtained (95%).

The structure of this compound was verified by $^1$H-NMR and $^{13}$C-NMR.

$^1$H-NMR (heavy dimethyl sulfoxide, δ ppm): 7.51 (1H, s, proton at 3-site of propenoic acid), 6.70 (1H, s, proton at 6'-site of aromatic ring), 6.42 (1H, s, proton at 3'-site of aromatic ring), 3.72 (3H, s, methyl group proton of methoxy group), 3.65 (3H, s, methyl group proton of methoxy group), 3.36 (2H, bs, amino group proton), 1.98 (3H, s, methyl group proton at 2-site of propene)

$^{13}$C-NMR (heavy dimethyl sulfoxide, δ ppm): 169.7 (quaternary carbon, carbonyl carbon at 1-site), 150.7 (quaternary carbon, carbon at 4'-site of aromatic ring), 142.6 (quaternary carbon, carbon at 2'-site of aromatic ring), 139.8 (quaternary carbon, carbon at 5'-site of aromatic ring), 134.7 (CH, carbon at 3-site of propene), 125.2 (quaternary carbon, carbon at 2-site of propene), 114.3 (CH, carbon at 6'-site of aromatic ring), 111.0 (quaternary carbon, carbon at 1'-site of aromatic ring), 100.1 (quaternary carbon, carbon at 3'-site of aromatic ring), 60.8 ($CH_2$, methylene group carbon of ethyl group), 56.5 ($CH_3$, methyl group carbon of methoxy group), 55.1 ($CH_3$, methyl group carbon of methoxy group), 14.4 ($CH_3$, methyl group carbon of ethyl group), 14.3 ($CH_3$, methyl group carbon at 2-site of propene).

Synthesis of (E) 3-(2-amino-4,5-dimethoxyphenyl)-2-methyl-2-propenoic acid p-nitrophenyl ester Into 20 ml of dichloromethane, 0.82 g (3.5 mmol) of (E) 3-(2-amino-4,5-dimethoxyphenyl)-2-methyl-2-propenoic acid and 0.97 g (7 mmol) of p-nitrophenol (manufactured by Wako Pure Chemical Industries, Ltd.) were dissolved, and 40 mg of dimethylaminopyridine (manufactured by Wako Pure Chemical Industries, Ltd.) were added thereto. While this mixture was stirred under cooling with ice, 0.81 g (4.2 mmol) of 1-ethyl-3-(3-dimethylaminopropyl)-carbodiimide hydrochloride (EDC/HCl) (manufactured by Wako Pure Chemical Industries, Ltd.) were added thereto in portions. The mixture was returned to room temperature and then was stirred for 20 hours. After the end point of the reaction was verified by TLC, the reaction liquid was concentrated under a reduced pressure and then was dissolved in 100 ml of ethyl acetate. After this solution was washed and dried, the solvent was evaporated, whereby a syrupy crude product was obtained. This product was refined by a silica gel column chromatography (n-hexane/ethyl acetate=2/1), whereby 0.15 g of the aimed compound was obtained as a yellow crystal (yield: 12%).

The structure of this compound was verified by $^1$H-NMR and $^{13}$C-NMR.

$^1$H-NMR (heavy chloroform, δ ppm): 8.31 (2H, d, J=9 Hz, protons at 2"- and 6"-sites of p-nitrophenyloxy group), 7.88 (1H, s, proton at 3-site of propene), 7.36 (2H, d, J=9 Hz, protons at 3"- and 5"-sites of p-nitrophenyloxy group), 6.79 (1H, s, proton at 6'-site of cinnamyl aromatic ring), 6.33 (1H, s, proton at 3'-site of cinnamyl aromatic ring), 3.88 (3H, s, methyl group proton of methoxy group), 3.84 (3H, s, methyl group proton of methoxy group), 3.68 (2H, bs, amino group proton), 2.20 (3H, s, m, methyl group proton at 2-site of propene)

$^{13}$C-NMR (heavy chloroform, δ ppm): 166.2 (quaternary carbon, carbonyl group carbon at 1-site), 156.1 (quaternary carbon, carbon at 1"-site of p-nitrophenyloxy group), 151.5 (quaternary carbon, carbon at 4'-site of cinnamyl aromatic ring), 145.2 (quaternary carbon, carbon at 4"-site of p-nitrophenyloxy group), 141.9 (quaternary carbon, carbon at 2'-site of cinnamyl aromatic ring), 140.3 (quaternary carbon, carbon at 5'-site of cinnamyl aromatic ring), 137.7 (CH, carbon at 3-site of propene), 125.6 (quaternary carbon, carbon at 2-site of propene), 125.2 (CH, carbons at 3"- and 5"-sites of p-nitrophenyloxy group), 122.6 (CH, carbons at 2"- and 6"-sites of p-nitrophenyloxy group), 113.4 (CH, carbon at 6'-site of cinnamyl aromatic carbon), 112.0 (quaternary carbon, carbon at 1'-site of cinnamyl aromatic ring), 100.4 (CH, carbon at 3'-site of cinnamyl aromatic ring), 56.7 ($CH_3$, methyl group carbon of methoxy group), 55.8 ($CH_3$, methyl group carbon of methoxy group), 14.5 ($CH_3$, methyl group carbon bound to 2-site of propene).

Synthesis of (E) 3-(2-amino-4,5-dimethoxyphenyl)-2-methyl-2-propenoic acid phenethyl amide Into 30 ml of dimethylformamide, 0.72 g (2.0 mmol) of (E) 3-(2-amino-4,5-dimethoxyphenyl)-2-methyl-2-propenoic acid p-nitrophenyl ester obtained above and 0.48 g (4.0 mmol) of 2-phenylethylamine (manufactured by Tokyo Kasei Kogyo Co., Ltd.) were dissolved; and the mixture was reacted at room temperature for one night. The reaction liquid was concentrated under a reduced pressure, and the resulting residue was dissolved in ethyl acetate. After the resulting solution was washed and was dried with magnesium sulfate anhydride, the solvent was eliminated under a reduced pressure, whereby a crude product was obtained. This product was refined by an aminopropyl-modified type silica gel column chromatography (n-hexane/ethyl acetate=1/1), whereby 0.68 g of the aimed compound was obtained (yield: quantitative).

The structure of this compound was verified by $^1$H-NMR and $^{13}$C-NMR.

$^1$H-NMR (heavy chloroform, δ ppm): 7.35–7.30 (2H, m, protons at 2"- and 6"-sites of phenethyl aromatic ring), 7.26–7.21 (4H, m, protons at 3-site of propene and at 3"-, 4"-, and 5"-sites of phenethyl aromatic ring), 6.60 (1H, s, proton at 6'-site of cinnamate aromatic ring), 6.29 (1H, s, proton at 3'-site of cinnamate aromatic ring), 5.93 (1H, bs, amino proton of amide group), 3.84 (3H, s, methyl group proton of methoxy group), 3.78 (3H, s, methyl group proton of methoxy group), 3.64 ppm (2H, dt, J=7 Hz, methylene group proton of phenethyl), 3.54 ppm (2H, s, amino group proton), 2.90 ppm (2H, t, J=7 Hz, methylene group proton of phenethyl), 1.96 ppm (3H, s, methyl group proton bound to 2-site of propene)

$^{13}$C-NMR (heavy chloroform, δ ppm): 169.1 (quaternary carbon, carbonyl carbon at 1-site), 150.2 (quaternary carbon, carbon at 4'-site of cinnamate aromatic ring), 141.6 (quaternary carbon, carbon at 2'-site of cinnamate aromatic ring), 139.2 (quaternary carbon, carbon at 5'-site of cinnamate aromatic ring), 139.0 (quaternary carbon, carbon at 1"-site of phenethyl aromatic ring), 131.7 (quaternary carbon, carbon at 2-site of propene), 130.3 (CH, carbon at 3-site of propene), 128.8 (CH, carbons at 2"- and 6"-sites of phenethyl aromatic ring), 128.7 (CH, carbons at 3"- and 5"-sites of phenethyl aromatic ring), 126.7 (CH, carbon at 4"-site of phenethyl aromatic ring), 113.7 (CH, carbon at 6'-site of cinnamate aromatic ring), 112.8 (quaternary carbon, carbon at 1'-site of cinnamate aromatic ring), 100.4 (CH, carbon at 3'-site of cinnamate aromatic ring), 56.7 ($CH_3$, methyl group carbon of methoxy group), 55.8 ($CH_3$, methyl group carbon of methoxy group), 41.0 ($CH_2$, methylene group carbon of phenethyl), 35.7 ($CH_2$, methylene group carbon of phenethyl), 14.3 ($CH_3$, methyl group carbon bound to 2-site of propene).

Synthesis of (E) N-L-glutamic acid 3-(2-amino-4,5-dimethoxyphenyl)-2-methyl-2-propenoic amide Into 80 ml of tetrahydrofuran, 0.72 g (2.0 mmol) of (E) 3-(2-amino-4,5-dimethoxyphenyl)-2-methyl-2-propenoic acid p-nitrophenyl ester was dissolved; and, with an aqueous solution in which 2.3 g (10 mmol) of L-glutamic acid had been dissolved in 160 ml of a 0.5-N aqueous sodium hydrogencarbonate solution being added thereto, the mixture was reacted at room temperature for one night. After its pH was adjusted to 4 with 2-N hydrochloric acid being added thereto, the reaction liquid was concentrated under a reduced pressure as it was. The resulting residue was once dissolved in 30 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.74 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.44 (1H, d, J=7.5 Hz, amide group proton), 7.34 (1H, s, proton at 3-site of propenoic acid), 7.24 (1H, s, proton at 3'-site of aromatic ring), 6.94 (1H, s, proton at 6'-site of aromatic ring), 4.36 (1H, ddd, J=9.3 Hz, 7.7 Hz, 5.5 Hz, methine group proton at α-site of glutamic acid portion), 4.10 (2H, bs, amino group proton), 3.82 (6H, s, methyl group proton of methoxy group), 2.47 (2H, dd, J=7.5 Hz, 7.5 Hz, methylene group proton at γ-site of glutamic acid portion), 2.07 (2H, m, methylene group proton at β-site of glutamic acid portion), 1.97 (3H, s, methyl group proton bound to 2-site of propene)

$^{13}$C-NMR (heavy dimethyl sulfoxide, δ ppm): 169.3, 169.1, 169.0 (quaternary carbon, carbonyl carbon in glutamic acid portion and carbonyl carbon at 1-site), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, carbon at 3-site of propene), 122.6 (quaternary carbon, carbon at 1'-site of aromatic ring), 112.8 (CH, carbon at 6'-site of aromatic ring), 107.6 (CH, carbon at 3'-site of aromatic ring), 55.8 (CH$_3$, methyl group carbon of methoxy group), 55.7 (CH$_3$, methyl group carbon of methoxy group), 51.7 (CH, methine group carbon at α-site of glutamic acid portion), 30.3 (CH$_2$, methylene group carbon at γ-site of glutamic acid portion), 26.0 (CH$_2$, methylene group carbon at β-site of glutamic acid portion), 14.5 (CH$_3$, methyl group carbon bound to 2-site of propene).

Synthesis of (E) N-(o-di-t-butyloxy)-L-glutamic acid 3-(2-amino-4,5-dimethoxyphenyl)-2-methyl-2-propenoic amide Into 200 ml of tetrahydrofuran, 0.36 g (1.0 mmol) of (E) 3-(2-amino-4,5-dimethoxyphenyl)-2-methyl-2-propenoic acid p-nitrophenyl ester and 0.89 g (3.0 mmol) of glutamic acid di-t-butyl ester hydrochloride (manufactured by Sigma Chemical Co.) were dissolved; and the mixture was reacted for 4 hours at room temperature. The solvent was eliminated from this reaction liquid under a reduced pressure, and the resulting residue was dissolved in ethyl acetate. Thus obtained solution was washed, dried on sodium sulfate anhydride, and then concentrated, whereby a crude product was obtained. This product was refined by a column chromatography (silica gel (aminopropyl-modified type) manufactured by Fuji Silysia Chem. Co., NH-DM1020 1000 g; eluent: hexane/ethyl acetate=1/1), whereby 0.48 g of the aimed compound was obtained (yield: quantitative).

The structure of this compound was verified by $^1$H-NMR and $^{13}$C-NMR.

$^1$H-NMR (heavy chloroform, δ ppm): 7.34 (1H, s, proton at 3-site of propenoic acid), 6.75 (1H, d, J=7.3 Hz, amide group proton), 6.63 (1H, s, proton at 6'-site of aromatic ring), 6.30 (1H, s, proton at 3'-site of aromatic ring), 4.59 (1H, dt, J=7.3 Hz, 4.6 Hz, methine group proton at α-site of glutamic acid portion), 3.85 (3H, s, methyl group proton of methoxy group), 3.80 (3H, s, methyl group proton of methoxy group), 3.59 (2H, bs, amino group proton), 2.39 (2H, m, methylene group proton at γ-site of glutamic acid portion), 2.25 (2H, m, methylene group proton at β-site of glutamic acid portion), 2.05 (3H, s, methyl group proton at 2-site of propene), 1.50 (9H, s, methyl group proton of butyl group), 1.45 (9H, s, methyl group proton of butyl group).

$^{13}$C-NMR (heavy chloroform, δ ppm): 172.6 (quaternary carbon, carbonyl carbon in glutamic acid portion), 171.2 (carbonyl carbon in glutamic acid portion), 168.7 (quaternary carbon, carbonyl carbon at 1-site), 150.4 (quaternary carbon, carbon at 4'-site of aromatic ring), 141.6 (quaternary carbon, carbon at 2'-site of aromatic ring), 139.2 (quaternary carbon, carbon at 5'-site of aromatic ring), 131.1 (CH, carbon at 3-site of propene), 131.1 (quaternary carbon, carbon at 2-site of propene), 113.6 (CH, carbon at 6'-site of aromatic ring), 112.8 (quaternary carbon, carbon at 1'-site of aromatic ring), 100.3 (CH, carbon at 3'-site of aromatic ring), 82.4 (quaternary carbon, butyl group carbon), 80.8 (quaternary carbon, butyl group carbon), 56.7 (CH$_3$, methyl group carbon of methoxy group), 55.8 (CH$_3$, methyl group carbon of methoxy group), 52.8 (CH, methine group carbon at α-site of glutamic acid portion), 31.7 (CH$_2$, methylene group proton at γ-site of glutamic acid portion), 28.1 (CH$_3$, methyl group carbon of butyl group), 27.5 (CH$_2$, methylene group proton at β-site of glutamic acid portion), 14.2 (CH$_3$, methyl group carbon at 2-site of propene).

Synthesis of ethyl 2-methyl-3-(2-nitrophenyl)-2-propenate

Into 500 ml of benzene, 21.0 g (139.0 mmol) of 2-nitrobenzaldehyde (manufactured by Aldrich Chemical Co., Inc.) and 50.0 g (138.0 mmol) of Wittig reagent (carbethoxyethylidene triphenylphosphorane, manufactured by Aldrich Chemical Co., Inc.) were dissolved; and the mixture was stirred at room temperature for one night. After the completion of the reaction was verified by TLC, the reaction liquid was concentrated under a reduced pressure, and ethanol was added to the resulting residue. The crystal precipitated in this solution was filtered out, and the filtrate was concentrated under a reduced pressure, so as to yield an oily product, which was then refined by a silica gel column chromatography (silica gel; developing solvent: ethyl acetate/hexane=1/4), whereby 32.1 g of the aimed compound were obtained as an oily product (yield: 98.2%).

The structure of this compound was determined by $^1$H-NMR and $^{13}$C-NMR.

$^1$H-NMR (heavy chloroform, δ ppm): 8.13 (d, 1H, proton at 3'-site of aromatic ring), 7.90 (s, 1H, proton at 3-site of propene), 7.66 (dd, 1H, proton at 5'-site of aromatic ring), 7.51 (dd, 1H, proton at 4'-site of aromatic ring), 7.37 (d, 1H, proton at 6'-site of aromatic ring), 4.30 (q, 2H, methylene group proton of ethyl group), 1.90 (s, 3H, methyl group proton bound to 2-site of propene), 1.36 (t, 3H, methyl proton of ethyl group)

$^{13}$C-NMR (heavy chloroform, δ ppm): 167.6 (quaternary carbon, carbonyl carbon at 1-site), 147.8 (quaternary carbon, carbon at 2'-site of aromatic ring), 135.3 (CH, carbon at 3-site of propene), 133.2 (CH, carbon at 5'-site of aromatic ring), 132.0 (quaternary carbon, carbon at 1'-site of aromatic ring), 131.3 (CH, carbon at 4'-site of aromatic ring), 130.6 (quaternary carbon, carbon at 2-site of propene), 128.9 (CH, carbon at 6'-site of aromatic ring), 124.9 (CH, carbon at 3'-site of aromatic ring), 61.1 (CH$_2$, methylene group carbon of ethyl group), 14.3 (CH$_2$, methyl group carbon of ethyl group), 14.0 (CH$_3$, methyl group carbon bound to 2-site of propene).

Synthesis of (E) 2-methyl-3-(2-nitrophenyl)-2-propenoic acid

Into 200 ml of methanol, 11.8 g (50.2 mmol) of ethyl 2-methyl-3-(2-nitrophenyl)-2-propenate were dissolved; and, with 200 ml of a 2-N aqueous sodium hydroxide solution being added thereto, the mixture was stirred at 40° C. for one night. After the completion of the reaction was verified by TLC, the reaction liquid was concentrated under a reduced pressure. After the pH was adjusted to 1 with 1-N hydrochloric acid being added thereto, the resulting residue was dissolved in ethyl acetate. After being washed three times with water, the solution was dried for one night with sodium sulfate anhydride being added thereto. After sodium sulfate was filtered out from the dried solution, the filtrate was concentrated under a reduced pressure, whereby 10.2 g of the aimed compound were obtained as a crystal (yield: 98.0%).

The structure of this compound was determined by $^1$H-NMR and $^{13}$C-NMR.

$^1$H-NMR (heavy dimethyl sulfoxide, δ ppm): 12.69 (bs, 1H, carboxyl group proton), 8.15 (d, 1H, proton at 3'-site of aromatic ring), 7.80 (dd, 1H, proton at 5'-site of aromatic ring), 7.76 (s, 1H, proton at 3-site of propene), 7.64 (dd, 1H, proton at 4'-site of aromatic ring), 7.53 (d, 1H, proton at 6'-site of aromatic ring), 1.82 (s, 3H, methyl group proton bound to 2-site of propene)

$^{13}$C-NMR (heavy dimethyl sulfoxide, δ ppm): 168.5 (quaternary carbon, carboxyl group carbon), 147.5 (quaternary carbon, carbon at 2'-site of aromatic ring), 134.5 (CH, carbon at 3-site of propene), 133.7 (CH, carbon at 5'-site of aromatic ring), 131.3 (CH, carbon at 6'-site of aromatic ring), 130.9 (quaternary carbon, carbon at 1'-site of aromatic ring), 130.5 (quaternary carbon, carbon at 2-site of propene), 129.4 (CH, carbon at 4'-site of aromatic ring), 124.5 (CH, carbon at 3'-site of aromatic ring), 13.7 (CH$_3$, methyl group carbon bound to 2-site of propene).

Synthesis of (E) ethyl 3-(2-aminophenyl)-2-methyl-2-propenate

Into 160 ml of acetic acid, 10 g (42.5 mmol) of (E) ethyl 2-methyl-3-(2-nitrophenyl)-2-propenate were dissolved. While the solution was stirred, 10.9 g (195.2 mmol) of iron powder (Koso Chem. Co.) and 12 ml of distilled water were added thereto at room temperature; and temperature was raised, so that reflux was carried out for 1 hour at 100° C. After the end point of the reaction was verified by TLC, the reaction liquid was cooled, and acetic acid was evaporated under a reduced pressure. Ethyl acetate was added to the residue, and insoluble matters were filtered out. Thus obtained filtrate was successively washed with water and a saturated aqueous sodium hydrogencarbonate solution. The washed solution was dried for one night with sodium sulfate being added thereto. After sodium sulfate anhydride was filtered out, the filtrate was concentrated under a reduced pressure. The resulting oily product was refined by a silica gel column chromatography (silica gel; developing solvent: ethyl acetate/hexane=1/3), whereby 6.4 g of the aimed compound were obtained as an oily product (yield: 71.5%).

The structure of this compound was determined by $^1$H-NMR and $^{13}$C-NMR.

$^1$H-NMR (heavy chloroform, δ ppm): 7.60 (s, 1H, proton at 3-site of propene), 7.14 (dd, 1H, proton at 4'-site of aromatic ring), 7.10 (d, 1H, protonat 6'-site of aromatic ring), 6.77 (dd, 1H, proton at 5'-site of aromatic ring), 6.72 (d, 1H, proton at 3'-site of aromatic ring), 4.27 (q, 2H, methylene group proton of ethyl group), 3.74 (bs, 2H, amino group proton), 2.00 (s, 3H, methyl group proton bound to 2-site of propene), 1.35 (t, 3H, methyl group proton of ethyl group).

$^{13}$C-NMR (heavy chloroform, δ ppm): 168.4 (quaternary carbon, carbonyl carbon at 1-site), 144.5 (quaternary carbon, carbon at 2'-site of aromatic ring), 134.9 (CH, carbon at 3-site of propene), 130.2 (quaternary carbon, carbon at 2-site of propene), 129.6 (CH, carbon at4'-site of aromatic ring), 129.4 (CH, carbon at 6'-site of aromatic ring), 121.3 (quaternary carbon, carbon at 1'-site of aromatic ring), 118.1 (CH, carbon at 5'-site of aromatic ring), 115.5 (CH, carbon at 3'-site of aromatic ring), 60.8 (CH$_2$, methylene group carbon of ethyl group), 14.3 (CH$_3$, methyl group carbon of ethyl group), 14.1 (CH$_3$, methyl group carbon bound to 2-site of propene).

Synthesis of ethyl 3-(4-chloro-2-nitrophenyl)-2-methyl-2-propenate

Into 200 ml of benzene, 10.0 g (53.8 mmol) of 4-chloro-2-nitrobenzaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were dissolved; and the mixture was stirred at ordinary temperature for one night. After the completion of the reaction was verified by TLC, the reaction liquid was concentrated, whereby a crude product was obtained. This crude product was refined by a column chromatography (aminopropyl-modified silica gel (Fuji Silysia Chem. Co., NH-DM); developing solvent: hexane/ethyl acetate=1/1), whereby 13.1 g of the aimed compound were obtained as a crystal (yield: 97%).

The structure of this compound was determined by $^1$H-NMR and $^{13}$C-NMR.

$^1$H-NMR (heavy chloroform, δ ppm): 8.14 (s, 1H, proton at 3'-site of aromatic ring), 7.82 (s, 1H, proton at 3-site of propene), 7.64 (d, 1H, proton at 5'-site of aromatic ring), 7.32 (d, 1H, proton at 6'-site of aromatic ring), 4.29 (q, 2H, methylene group proton of ethyl group), 1.90 (s, 3H, methyl group proton bound to 2-site of propene), 1.36 (t, 3H, methyl group proton of ethyl group)

$^{13}$C-NMR (heavy chloroform, δ ppm): 167.4 (quaternary carbon, carbonyl carbon at 1-site), 148.0 (quaternary carbon, carbon at 2'-site of aromatic ring), 134.8 (quaternary carbon, carbon at 4'-site of aromatic ring), 134.1 (CH, carbon at3-site of propene), 133.4 (CH, carbon at 5'-site of aromatic ring), 132.5 (CH, carbon at6'-site of aromatic ring), 131.3 (quaternary carbon, carbon at 1'-site of aromatic ring), 130.3 (quaternary carbon, carbon at 2-site of propene), 125.1 (CH, carbon at3'-site of aromatic ring), 61.3 (CH$_2$, methylene group carbon of ethyl group), 14.3 (CH$_3$, methyl group carbon of ethyl group), 14.1 (CH$_3$, methyl group carbon bound to 2-site of propene).

Synthesis of (E) ethyl 3-(2-amino-4-chlorophenyl)-2-methyl-2-propenate

Into 170 ml of acetic acid, 11.0 g of ethyl 3-(4-chloro-2-nitrophenyl)-2-methyl-2-propenate were dissolved; and, while the mixture was stirred, 10.9 g (195.2 mmol) of iron powder (Koso Chem. Co.) and 13 ml of distilled water were added thereto at room temperature. The temperature of the mixture was raised, so that the reaction was carried out at 97° C. for 2 hours. After the end point of the reaction was verified by TLC, the reaction liquid was cooled, and acetic acid was evaporated under a reduced pressure. To the residue, 300 ml of water and 400 ml of ethyl acetate were added. Then, insoluble matters were filtered out. The ethyl acetate layer of thus obtained filtrate was successively washed with water, an aqueous sodium hydrogencarbonate solution, and a saturated aqueous sodium chloride solution; and then was dried for one night with sodium sulfate being added thereto. After sodium sulfate was filtered out from the dried solution, the filtrate was concentrated under a reduced pressure, whereby 9.8 g of a crude crystal were obtained. This crystal was refined by a silica gel column chromatography (aminopropyl-modified silica gel (Fuji Silysia Chem. Co., NH-DM1020); developing solvent: hexane/ethyl acetate=2/1), whereby 7.2 g of the aimed compound were obtained (yield: 73.3%).

The structure of this compound was determined by $^1$H-NMR and $^{13}$C-NMR.

$^1$H-NMR (heavy chloroform, δ ppm): 7.50 (s, 1H, proton at 3-site of propene), 7.01 (d, 1H, proton at 6'-site of aromatic ring), 6.73 (d, 1H, protonat 5'-site of aromatic ring), 6.72 (s, 1H, proton at 3'-site of aromatic ring), 4.27 (q, 2H, methylene group proton of ethyl group), 3.68 (bs, 2H, amino group proton), 1.98 (s, 3H, methyl group proton bound to 2-site of propene), 1.35 (t, 3H, methyl group proton of ethyl group).

$^{13}$C-NMR (heavy chloroform, δ ppm): 168.2 (quaternary carbon, carbonyl carbon at 1-site), 145.6 (quaternary carbon, carbon at 2'-site of aromatic ring), 134.9 (quaternary carbon, carbon at 4'-site of aromatic ring), 133.8 (CH, carbon at 3-site of propene), 130.9 (quaternary carbon, carbon at 2-site of propene), 130.7 (CH, carbon at 6'-site of aromatic ring), 119.6 (quaternary carbon, carbon at 1'-site of aromatic ring), 118.2 (CH, carbon at 5'-site of aromatic ring), 115.2 (CH, carbon at 3'-site of aromatic ring), 61.0 (CH$_2$, methylene group carbon of ethyl group), 14.3 (CH$_3$, methyl group carbon of ethyl group), 14.2 (CH$_3$, methyl group carbon bound to 2-site of propene).

Synthesis of ethyl 3-(5-chloro-2-nitrophenyl)-2-methyl-2-propenate

To 200 ml of benzene, 10.0 g (53.8 mmol) of 5-chloro-2-nitrobenzaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were added, and the mixture was stirred at room temperature for one night. After the completion of the reaction was verified by TLC, the reaction liquid was concentrated, whereby a crude product was obtained. This crude product was refined by a column chromatography (aminopropyl-modified silica gel (Fuji Silysia Chem. Co., NH-DM); developing agent: hexane/ethyl acetate=1/1), whereby 13.3 g of the aimed compound were obtained as a crystal (yield: 98%).

The structure of this compound was determined by $^1$H-NMR and $^{13}$C-NMR.

$^1$H-NMR (heavy chloroform, δ ppm): 8.11 (d, 1H, proton at 3'-site of aromatic ring), 7.83 (s, 1H, proton at 3-site of propene), 7.47 (d, 1H, proton at 4'-site of aromatic ring), 7.34 (s, 1H, proton at 6'-site of aromatic ring), 4.30 (q, 2H, methylene group proton of ethyl group), 1.91 (s, 3H, methyl group proton bound to 2-site of propene), 1.35 (t, 3H, methyl group proton of ethyl group) $^{13}$C-NMR (heavy chloroform, δ ppm): 167.3 (quaternary carbon, carbonyl carbon at 1-site), 146.1 (quaternary carbon, carbon at 2'-site of aromatic ring), 139.8 (quaternary carbon, carbon at 5'-site of aromatic ring), 134.1 (CH, carbon at 3-site of propene), 133.8 (quaternary carbon, carbon at 1'-site of aromatic ring), 131.4 (quaternary carbon, carbon at 2-site of propene), 131.1 (CH, carbon at 6'-site of aromatic ring), 129.0 (CH, carbon at 4'-site of aromatic ring), 126.4 (CH, carbon at 3'-site of aromatic ring), 61.3 (CH$_2$, methylene group carbon of ethyl group), 14.2 (CH$_3$, methyl group carbon of ethyl group), 14.0 (CH$_3$ methyl group carbon bound to 2-site of propene).

Synthesis of (E) ethyl 3-(2-amino-5-chlorophenyl)-2-methyl-2-propenate

Into 170 ml of acetic acid, 11.0 g (41.0 mmol) of ethyl 3-(5-chloro-2-nitrophenyl)-2-methyl-2-propenate were dissolved. After 10.9 g (195.2 mmol) of iron powder (Koso Chem. Co.) and 13 ml of distilled water were added thereto while being stirred at room temperature, temperature was raised, so as to carry out a reaction for 2 hours at 97° C. After the end point of the reaction was verified by TLC, the reaction liquid was cooled, and acetic acid was evaporated under a reduced pressure. To this residue, 300 ml of water and 400 ml of ethyl acetate were added; and insoluble matters were filtered out. The ethyl acetate layer of the filtrate was successively washed with water, an aqueous sodium hydrogencarbonate solution, and a saturated aqueous sodium chloride solution. The washed solution was dried for one night with sodium sulfate being added thereto. After sodium sulfate was filtered out, the filtrate was concentrated under a reduced pressure, whereby 9.8 g of an oily crude product were obtained. This product was refined by a column chromatography (aminopropyl-modified silica gel (Fuji Silysia Chem. Co., NH-DM1020); developing solvent: hexane/ethyl acetate=2/1), whereby 7.2 g of the aimed compound were obtained as an oily product (yield: 73.3%).

The structure of this compound was determined by $^1$H-NMR and $^{13}$C-NMR.

$^1$H-NMR (heavy chloroform, δ ppm): 7.49 (s, 1H, proton at 3-site of propene), 7.07 (d, 1H, proton at 4'-site of aromatic ring), 7.05 (s, 1H, proton at 6'-site of aromatic ring), 6.64 (d, 1H, proton at 3'-site of aromatic ring), 4.27 (q, 2H, methylene group proton of ethyl group), 3.74 (bs, 2H, amino group proton), 1.99 (s, 3H, methyl group proton bound to 2-site of propene), 1.35 (t, 3H, methyl group proton of ethyl group).

$^{13}$C-NMR (heavy chloroform, δ ppm): 168.0 (quaternary carbon, carbonyl carbon at 1-site), 143.2 (quaternary carbon, carbon at 2'-site of aromatic ring), 133.6 (CH, carbon at 3-site of propene), 131.4 (quaternary carbon, carbon at 2-site of propene), 129.1 (CH, carbon at 4'- or 6'-site of aromatic ring), 128.9 (CH, carbon at 4'- or 6'-site of aromatic ring), 122.6 (quaternary carbon, carbon at 1'- or 5'-site of aromatic ring), 122.5 (quaternary carbon, carbon at 1'- or 5'-site of aromatic ring), 116.7 (CH, carbon at 3'-site of aromatic ring), 61.0 (CH$_2$, methylene group carbon of ethyl group), 14.3 (CH$_3$, methyl group carbon of ethyl group), 14.2 (CH$_3$, methyl group carbon bound to 2-site of propene).

Synthesis of (E) 3-(2-amino-benzo[d]phenyl)-2-methyl-2-propenoic acid ethyl ester Into 30 ml of benzene, 2.0 g (7 mmol) of 3-(2-nitro-benzo[d]phenyl)-2-methyl-2-propenoic acid ethyl ester were dissolved; and, with 1.73 g of iron powder (Koso Chem. Co.) and 2.5 ml of distilled water being added thereto under stirring at room temperature, temperature was raised, so that a reaction was carried out for 1.5 hours at 70° C. After the completion of the reaction, insoluble matters were filtered out, and the filtrate was added to 100 ml of water. The resulting solution was extracted twice with 100 ml of ethyl acetate; and thus obtained ethyl acetate solution was successively washed with water, an aqueous sodium hydrogencarbonate solution, and a saturated aqueous sodium chloride solution. The washed solution was dried on sodium sulfate anhydride; and, after sodium sulfate was filtered out, the filtrate was concentrated. Thus obtained oily product was refined by a silica gel column chromatography (silica gel; developing solvent: ethyl acetate/hexane=1/5), whereby 1.4 g of the aimed compound were obtained as an oily product (yield: 77%).

The structure of this compound was verified by $^1$H-NMR and $^{13}$C-NMR.

¹H-NMR (heavy chloroform, δ ppm): 7.73 (1H, s, proton at 3-site of propene), 7.70–7.58 (2H, m, protons at 4'- and 7'-sites of aromatic ring), 7.58 (1H, s, proton at 8,'-site of aromatic ring), 7.40–7.20 (2H, m, protons at 5'- and 6'-sites of aromatic ring), 7.04 (1H, s, proton at 3'-site of aromatic ring), 4.31 (2H, q, J=7 Hz, methylene group proton of ethyl group), 3.89 (2H, bs, amino group proton), 2.06 (3H, s, methyl group proton bound to 2-site of propene), 1.37 (3H, t, J=7 Hz, methyl group proton of ethyl group).

¹³C-NMR (heavy chloroform, δ0 ppm): 168.2 (quaternary carbon, carbonyl carbon at 1-site), 142.6 (quaternary carbon, carbon at 2'-site of aromatic ring), 134.8 (CH, carbon at 3-site of propene), 134.7 (quaternary carbon, carbon at 3a'-site of aromatic ring), 131.6 (quaternary carbon, carbon at 2-site of propene), 129.2 (CH, carbon at 5'- or 6'-site of aromatic ring), 127.9 (CH, carbon at 5'- or 6'-site of aromatic ring), 127.5 (quaternary carbon, carbon at 7a'-site of aromatic ring), 126.8 (CH, carbon at 4'- or 7'-site of aromatic ring), 125.5 (CH, carbon at 4'- or 7'-site of aromatic ring), 124.8 (quaternary carbon, carbon at 1'-site of aromatic ring), 122.9 (CH, carbon at 8'-site of aromatic ring), 109.2 (CH, carbon at 3'-site of aromatic ring), 61.0 (CH$_2$, methylene group carbon of ethyl group), 14.4 (CH$_3$, methyl group carbon of ethyl group), 14.3 (CH$_3$, methyl group carbon bound to 2-site of propene).

Synthesis of (E) 3-(2-amino-benzo[d]phenyl)-2-methyl-2-propenoic acid

Into 10 ml of tetrahydrofuran (THF), 0.65 g of (E) 3-(2-amino-benzo[d]phenyl)-2-methyl-2-propenoic acid ethyl ester was dissolved; and, with 10 ml of a 1-N aqueous sodium hydroxide solution being added thereto, the mixture was reacted for 4 hours at 40° C. After the completion of the reaction, the reaction liquid was cooled with 10 ml of a 1-N aqueous hydrochloric acid solution being added thereto, and the precipitated crystal was filtered out, whereby 0.57 g of the aimed compound was obtained (yield: 98%).

The structure of this compound was verified by ¹H-NMR and ¹³C-NMR.

¹H-NMR (heavy dimethyl sulfoxide, δ ppm): 7.85–7.75 (3H, m, protons at 5'-, 6'-, and 8'-sites of benzocinnamyl aromatic ring), 7.73 (1H, s, proton at 3-site of propene), 7.52–7.33 (3H, m, protons at 4'-, 7'-, and 3'-sites of benzocinnamyl aromatic ring), 2.02 (3H, s, methyl group proton bound to 2-site of propene).

¹³C-NMR (heavy dimethyl sulfoxide, δ ppm): 168.9 (quaternary carbon, carbonyl carbon at 1-site), 133.3 (CH, carbon at 3-site of propene), 131.5 (quaternary carbon, carbon at 2-site of propene), 131.4 (quaternary carbon, carbon at 3a'-site of benzocinnamyl aromatic ring), 129.3 (CH, carbons at 5'- and 6'-sites of benzocinnamyl aromatic ring), 128.7 (quaternary carbon, carbon at 7a'-site of benzocinnamyl aromatic ring), 127.8 (CH, carbon at 4'- or 7'-site of benzocinnamyl aromatic ring), 126.8 (CH, carbon at 4'- or 7'-site of benzocinnamyl aromatic ring), 126.2 (quaternary carbon, carbon at 1'-site of benzocinnamyl aromatic ring), 126.0 (CH, carbon at 8'-site of benzocinnamyl aromatic ring), 124.2 (CH, carbon at 3'-site of benzocinnamyl aromatic ring), 14.1 (CH$_3$, methyl group carbon bound to 2-site of propene).

Synthesis of (E) 3-(2-amino-benzo[d]phenyl)-2-methyl-2-propenoic acid p-nitrophenyl ester Into 20 ml of dichloromethane, 0.57 g (2.5 mmol) of (E)3-(2-amino-benzo[d]phenyl)-2-methyl-2-propenoic acid and 0.52 g (3.8 mmol) of p-nitrophenol (manufactured by Wako Pure Chemical Industries, Ltd.) were dissolved; and 20 mg of dimethylaminopyridine (manufactured by Wako Pure Chemical Industries, Ltd.) were added thereto. Thereafter, while the mixture was stirred under cooling with ice, 0.71 g (3.8 mmol) of 1-ethyl-3-(3-dimethylaminopropyl)-carbodiimide hydrochloride (EDC-HCl) (manufactured by Wako Pure Chemical Industries, Ltd.) was added thereto in portions. The liquid was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbonate solution and then with a saturated aqueous sodium chloride solution, and was dried with magnesium sulfate anhydride. Thereafter, the solvent was evaporated, whereby a crude product was obtained. This product was recrystallized from ethanol, whereby 0.69 g of the aimed product was obtained as a crystal (yield: 80%).

The structure of this compound was verified by ¹H-NMR and ³C-NMR.

¹H-NMR (heavy chloroform, δ ppm): 8.32 (2H, d, J=9 Hz, protons at 3"- and 5"-sites of nitrophenyloxy group), 8.01 (1H, s, proton at 3-site of propene), 7.73–7.67 (2H, m, protons at 5'- and 6'-sites of benzocinnamyl aromatic ring), 7.61 (1H, d, d=8 Hz, proton at 4'- or 7'-site of benzocinnamyl aromatic ring), 7.43–7.38 (1H, m, proton at 4'- or 6'-site of benzocinnamyl aromatic ring), 7.39 (2H, d, J=9 Hz, protons at 2"- and 6"-sites of nitrophenyloxy group), 7.29–7.24 (1H, m, proton at 8'-site of benzocinnamyl aromatic ring), 7.09 (1H, s, proton at 3'-site of benzocinnamyl aromatic ring), 3.91 (2H, bs, amino group proton), 2.23 (3H, s, methyl group proton bound to 2-site of propene).

¹³C-NMR (heavy chloroform, δ ppm): 165.7 (quaternary carbon, carbonyl carbon at 1-site), 155.8 (quaternary carbon, carbon at 1"-site of nitrophenyloxy group), 145.3 (quaternary carbon, carbon at 4"-site of nitrophenyloxy group), 142.4 (quaternary carbon, carbon at 2'-site of benzocinnamyl aromatic ring), 138.0 (CH, carbon at 3-site of propene), 135.0 (quaternary carbon, carbon at 2-site of propene), 129.6 (quaternary carbon, carbon at 3a'-site of benzocinnamyl aromatic ring), 129.4 (CH, carbon at 5'- or 6'-site of benzocinnamyl aromatic ring), 128.0 (CH, carbon at 5'- or 6'- site of benzocinnamyl aromatic ring), 127.5 (quaternary carbon, carbon at 7a'-site of benzocinnamyl aromatic ring), 127.1 (CH, carbon at 4'- or 7'-site of benzocinnamyl aromatic ring), 125.5 (CH, carbon at 4'-site or 7'-site of benzocinnamyl aromatic ring), 125.2 (CH, carbons at 3"- and 5"-sites of nitrophenyloxy group), 123.8 (quaternary carbon, carbon at 1'-site of benzocinnamyl aromatic ring), 123.1 (CH, carbon at 8'-site of benzocinnamyl aromatic ring), 122.5 (CH, carbons at 2"- and 6"-sites of nitrophenyloxy group), 109.7 (CH, carbon at 3'-site of benzocinnamyl aromatic ring), 14.4 (CH$_3$, methyl group carbon bound to 2-site of propene).

Synthesis of (E) 3-(2-aminophenyl)-2-methyl-2-propenoic acid

Into 10 ml of tetrahydrofuran (THF), 1.50 g (7.31 mmol) of (E) ethyl 3-(2-aminophenyl)-2-methyl-2-propenate were dissolved; and, with 10 ml of a 1-N aqueous sodium hydroxide solution being added thereto, the mixture was reacted at 40° C. for 4 hours. After the completion of the reaction was verified by TLC, the mixture was cooled with 10 ml of 1-N hydrochloric acid being added thereto. The precipitated crystal was filtered out, whereby 1.30 g of the aimed compound were obtained (yield: quantitative).

The structure of this compound was verified by $^1$H-NMR and $^{13}$C-NMR.

$^1$H-NMR (heavy dimethyl sulfoxide, δ ppm): 7.70 (1H, s, proton at 3-site of propene), 7.49 (1H, d, J=77 Hz, proton at 3'-site of aromatic ring), 7.42–7.29 (3H, m, protons at 4'-, 5'-, and 6'-sites of aromatic ring), 1.91 (3H, s, methyl group proton bound to 2-site of propene)

$^{13}$C-NMR (heavy dimethyl sulfoxide, δ ppm): 168.7 (quaternary carbon, carbonyl carbon at 1-site), 132.6 (CH, carbon at 3-site of propene), 132.1 (quaternary carbon, carbon at 2-site of propene), 130.2 (CH, carbon at 4'-site of aromatic ring), 129.3 (CH, carbon at 6'-site of aromatic ring), 128.8 (quaternary carbon, carbon at 1'-site of aromatic ring), 126.0 (CH, carbon at 5'-site of aromatic ring), 122.4 (CH, carbon at 3'-site of aromatic ring), 14.1 (CH$_3$, methyl group carbon bound to 2-site of propene).

Synthesis of (E) 3-(2-aminophenyl)-2-methyl-2-propenoic acid p-nitrophenyl ester Into 20 ml of dichloromethane, 0.19 g (1.1 mmol) of (E) 3-(2-aminophenyl)-2-methyl-2-propenoic acid and 0.18 g of p-nitrophenol (manufactured by Wako Pure Chemical Industries, Ltd.) were dissolved; and 10 mg of dimethylaminopyridine (manufactured by Wako Pure Chemical Industries, Ltd.) were added thereto. While the mixture was stirred under cooling with ice, 0.41 g of 1-ethyl-3-(3-dimethylaminopropyl)-carbodiimide hydrochloride (EDC-HCl) (manufactured by Wako Pure Chemical Industries, Ltd.) was added thereto in portions. The liquid was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbonate solution and then with a saturated aqueous sodium chloride solution, and was dried with magnesium sulfate anhydride. Further, the solvent was evaporated, whereby a crude product was obtained. This product was recrystallized from ethanol, whereby 0.29 g of the aimed product was obtained as a crystal (yield: 91%).

The structure of this compound was verified by $^1$H-NMR and $^{13}$C-NMR.

$^1$H-NMR (heavy dimethyl sulfoxide, δ ppm): 8.35 (2H, d, J=9 Hz, protons at 3"- and 5"-sites of nitrophenyloxy group), 7.86 (1H, s, proton at 3-site of propene), 7.54 (2H, d, J=9 Hz, protons at 2"- and 6"-sites of nitrophenyloxy group), 7.17 (1H, d, J=8 Hz, proton at 6'-site of cinnamyl aromatic ring), 7.09 (1H, dd, J=8 Hz, J=8 Hz, proton at 4'-site of cinncamyl aromatic ring), 6.75 (1H, d, J=8 Hz, proton at 3'-site of aromatic ring), 6.63 (1H, dd, J=8 Hz, J=8 Hz, proton at 5'-site of aromatic ring), 5.35 (2H, bs, amino group proton), 2.10 (3H, s, methyl group proton bound to 2-site of propene).

$^{13}$C-NMR (heavy dimethyl sulfoxide, δ ppm).: 165.8 (quaternary carbon, carbonyl carbon at 1-site), 156.0 (quaternary carbon, carbon at 1"-site of nitrophenyloxy group), 147.4 (quaternary carbon, carbon at 4"-site of nitrophenyloxy group), 144.8 (quaternary carbon, carbon at 2'-site of cinnamyl aromatic ring), 138.6 (CH, carbon at 3-site of propene), 130.0 (CH, carbon at 4'-site of cinnamyl aromatic ring), 129.4 (CH, carbon at 6'-site of cinnamyl aromatic ring), 125.2 (quaternary carbon, carbon at 1'-site of cinnamyl aromatic ring), 125.1 (CH, carbons at 3"- and 5"-sites of nitrophenyloxy group), 123.1 (CH, carbons at 2"- and 6"-sites of nitrophenyloxy group), 118.6 (quaternary carbon, carbon at 2-site of propene), 115.5 (CH, carbon at 5'-site of cinnamyl aromatic ring), 115.3 (CH, carbon at 3'-site of cinnamyl aromatic ring), 14.2 (CH$_3$, methyl group carbon bound to 2-site of propene).

Synthesis of (E) 3-(2-amino-4-chlorophenyl)-2-methyl-2-propenoic acid

Into 10 ml of tetrahydrofuran (THF), 1.24 g (5.18 mmol) of (E) ethyl 3-(2-aminophenyl-4-chlorophenyl)-2-methyl-2-propenate were dissolved; and, with 10 ml of a 1-N aqueous sodium hydroxide solution being added thereto, the mixture was reacted at 40° C. for 4 hours. After the completion of the reaction was verified by TLC, the mixture was cooled with 10 ml of 1-N hydrochloric acid being added thereto. The precipitated crystal was filtered out, whereby 1.03 g of the aimed compound were obtained (yield: 94%).

The structure of this compound was verified by $^1$H-NMR and $^{13}$C-NMR.

$^1$H-NMR (heavy dimethyl sulfoxide, δ ppm): 7.42 (1H, s, proton at 3-site of propene), 7.02 (1H, d, J=8Hz, proton at 6'-site of aromatic ring), 6.74 (1H, s, proton at 3'-site of aromatic ring), 6.55 (1H, d, J=8 Hz, proton at 5'-site of aromatic ring), 5.37 (2H, bs, amino group proton), 1.90 (3H, s, methyl group proton bound to 2-site of propene).

$^{13}$C-NMR (heavy dimethyl sulfoxide, δ ppm): 169.2 (quaternary carbon, carbonyl carbon at 1-site), 148.2 (quaternary carbon, carbon at 2'-site of aromatic ring), 133.7 (CH, carbon at 3-site of propene), 133.4 (quaternary carbon, carbon at 4'-site of aromatic ring), 130.7 (CH, carbon at 6'-site of aromatic ring), 128.7 (quaternary carbon, carbon at 2-site of propene), 118.3 (quaternary carbon, carbon at 1'-site of aromatic ring), 115.0 (CH, carbon at 5'-site of aromatic ring), 114.0 (CH, carbon at 3'-site of aromatic ring), 14.1 (CH$_3$, methyl group carbon bound to 2-site of propene).

Synthesis of (E) 3-(2-amino-4-chlorophenyl)-2-methyl-2-propenoic acid p-nitrophenyl ester Into 20 ml of dichloromethane, 0.81 g (3.8 mmol) of (E) 3-(2-amino-4-chlorophenyl)-2-methyl-2-propenoic acid and 1.0 g of p-nitrophenol (manufactured by Wako Pure Chemical Industries, Ltd.) were dissolved; and 40 mg of dimethylaminopyridine (manufactured by Wako Pure Chemical Industries, Ltd.) were added thereto. Further, while the mixture was stirred under cooling with ice, 1.0 g of 1-ethyl-3-(3-dimethylaminopropyl)-carbodiimide hydrochloride (EDC-HCl) (manufactured by Wako Pure Chemical Industries, Ltd.) was added thereto in portions. This liquid was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbonate solution and then with a saturated aqueous sodium chloride solution, and was dried with magnesium sulfate anhydride. Thereafter, the solvent was evaporated, whereby a crude product was obtained. This product was recrystallized from ethanol, whereby 1.2 g of the aimed product were obtained as a crystal (yield: 91%).

The structure of this compound was verified by $^1$H-NMR and 13C-NMR.

$^1$H-NMR (heavy dimethyl sulfoxide, δ ppm): 8.30 (2H, d, J=9 Hz, protons at 3"- and 5"-sites of nitrophenyloxy group), 7.80 (1H, s, proton at 3-site of propene), 7.45 (2H, d, J=9 Hz, protons at 2"- and 6"-sites of nitrophenyloxy group), 7.09 (1H, d, J=8 Hz, proton at 6'-site of aromatic ring), 6.81 (1H, s, proton at3'-site of aromatic ring), 6.63 (1H, d, J=8 Hz, proton at 5'-site of aromatic ring), 5.08 (2H, bs, amino group proton), 2.11 (3H, s, methyl group proton bound to 2-site of propene).

$^{13}$C-NMR (heavy dimethyl sulfoxide, δ ppm): 170.5 (quaternary carbon, carbonyl carbon at 1-site), 160.9 (quaternary carbon, carbon at 1"-site of nitrophenyloxy group), 152.9 (quaternary carbon, carbon at 4"-site of nitrophenyloxy group), 149.8 (quaternary carbon, carbon at 2'-site of cinnamyl aromatic ring), 142.4 (CH, carbon at 3-site of propene), 139.9 (quaternary carbon, carbon at 4'-site of cinnamyl aromatic ring), 135.6 (CH, carbon at 6'-site of cinnamyl aromatic ring), 131.8 (quaternary carbon, carbon at 2-site of propene), 129.9 (CH, carbons at 3"- and 5"-sites of nitrophenyloxy group), 127.9 (CH, carbons at 2"- and 6"-sites of nitrophenyloxy group), 122.7 (quaternary carbon, carbon at 1'-site of cinnamyl aromatic ring), 121.1 (CH, carbon at 5'-site of cinnamyl aromatic ring), 119.7 (CH, carbon at 3'-site of cinnamyl aromatic ring), 19.2 ($CH_3$, methyl group carbon bound to 2-site of propene).

Synthesis of (E) N-2-(4-methoxyphenyl)ethyl 3-(2-amino-4-chlorophenyl)-2-methyl-2-propenoic amide Into 2 ml of dimethylformamide, 0.20 g (0.60 mmol) of (E)3-(2-amino-4-chlorophenyl)-2-methyl-2-propenoic acid p-nitrophenyl ester and 0.11 g (0.72 mmol) of 2-(4-methoxyphenyl)ethylamine (manufactured by Wako Pure Chemical Industries, Ltd.) were dissolved, and the mixture was reacted for 20 hours at room temperature. After the completion of the reaction was verified by TLC, ethyl acetate and water were added thereto. The resulting ethyl acetate layer was fractionated, and was washed several times with a 5% aqueous sodium hydrogencarbonate solution and then with a saturated aqueous sodium chloride solution. The washed solution was dried with magnesium sulfate anhydride, and the solvent was evaporated under a reduced pressure. The crude product obtained here was refined by a silica gel column chromatography (developing solvent: methylene chloride/methanol=95/5), whereby 0.19 g of the aimed compound was obtained (yield: quantitative).

The structure of this compound was verified by $^1$H-NMR and $^{13}$C-NMR.

$^1$H-NMR (heavy chloroform, δ ppm ): 7.15 (1H, s, proton at 3-site of propene), 7.13 (2H, d, J=7 Hz, protons at 2"- and 6"-sites of aromatic ring in 4-methoxyphenylethylamine portion), 6.92 (1H, d, J=8 Hz, proton at 6'-site of cinnamyl aromatic ring), 6.85 (2H, d, J=7 Hz, protons at 3"- and 5"-sites of aromatic ring in 4-methoxyphenylethylamine portion), 6.70 (1H, d, J=8 Hz, proton at 5'-site of cinnamyl aromatic ring), 6.66 (1H, s, proton at 3'-site of cinnamyl aromatic ring), 5.96 (1H, d, J=7 Hz, amide group proton), 3.79 (3H, s, methyl group proton of methoxy group), 3.59 (2H, t-d, J=7 Hz, J=7 Hz, methylene group proton at α-site of 4-methoxyphenylethylamine portion), 2.83 (2H, t, J=7 Hz, methylene group proton at β-site of 4-methoxyphenylethylamine portion), 1.90 (3H, s, methyl group proton bound to 2-site of propene).

$^{13}$C-NMR (heavy chloroform, δ ppm): 168.6 (quaternary carbon, carbonyl group carbon at 1-site of propene), 158.3 (quaternary carbon, carbon at 4"-site of aromatic ring in 4-methoxyphenylethylamine portion), 145.6 (quaternary carbon, carbon at 2'-site of cinnamyl aromatic ring), 134.5 (quaternary carbon, carbon at 4'-site of cinnamyl aromatic ring), 133.7 (quaternary carbon, carbon at 2-site of propene), 130.8 (quaternary carbon, carbon at 1"-site of aromatic ring in 4-methoxyphenylethylamine portion), 130.6 (CH, carbon at 6'- site of cinnamyl aromatic ring), 129.7 (CH, carbons at 2"- and 6"-sites of aromatic ring in 4-methoxyphenylethylamine portion), 129.5 (CH, carbon at 3-site of propene), 119.7 (quaternary carbon, carbon at 1'-site of cinnamyl aromatic ring), 118.0 (CH, carbon at 5'-site of cinnamyl aromatic ring), 115.0 (CH, carbon at 3'-site of cinnamyl aromatic ring), 114.1 (CH, carbons at 3"- and 5"-sites of aromatic ring in 4-methoxyphenylethylamine portion), 55.2 ($CH_3$, methyl group carbon of methoxy group), 41.2 ($CH_2$, methylene group carbon at a-site of α-methoxyphenylethylamine portion), 64.7 ($CH_2$, methylene group carbon at β-site of 4-methoxyphenylethylamine portion), 14.1 ($CH_3$, methyl group carbon bound to 2-site of propene).

Synthesis of (E) N-(2-naphtyl)methyl 3-(2-aminophenyl)-2-methyl-2-propenamide Into 4 ml of dimethylformamide, 0.65 g (2.2 mmol) of (E) 3-(2-aminophenyl)-2-methyl-2-propenoic acid p-nitrophenyl ester and 0.69 g (4.4 mmol) of 2-naphtylamine (manufactured by Aldrich Chemical Co., Inc.) were dissolved; and, with 0.36 ml of triethylamine (manufactured by Wako Pure Chemical Industries, Ltd.) being added thereto, the mixture was reacted at room temperature for 20 hours. After the completion of the reaction was verified by TLC, ethyl acetate and water were added to the mixture. The resulting ethyl acetate layer was fractionated, and was washed several times with a 5% aqueous sodium hydrogencarbonate solution and then with a saturated aqueous sodium chloride solution. After the washed solution was dried with magnesium sulfate anhydride, the solvent was evaporated under a reduced pressure, whereby a crude product was obtained. This product was refined by a silica gel column chromatography (developing solvent: methylene chloride/methanol=95/5), whereby 1.39 g of the aimed compound were obtained (yield: quantitative).

The structure of this compound was verified by $^1$H-NMR and $^{13}$C-NMR.

$^1$H-NMR (heavy chloroform, δ ppm): 8.07 (1H, d, proton at 4"-site of naphtyl aromatic ring), 7.90 (1H, d, J=8 Hz, proton at 5"- or 8"-site of naphtyl aromatic ring), 7.84 (1H, d, J=8 Hz, proton at 5"- or 8"-site of naphtyl aromatic ring), 7.58 (1H, dd, J=8 Hz, J=8 Hz, proton at 3"-site of naphtyl aromatic ring), 7.57–7.49 (3H, m, protons at 2"-, 6"-, and 7"-sites of naphtyl aromatic ring), 7.32 (1H, s, proton at 3-site of propene), 7.10 (1H, dd, J=8 Hz, J=8 Hz, proton at 4'-site of cinnamyl aromatic ring), 7.02 (1H, d, J=8 Hz, proton at 6'-site of cinnamyl aromatic ring), 6.73 (1H, dd, J=8 Hz, J=8 Hz, proton at 5'-site of cinnamyl aromatic ring), 6.69 (1H, d, J=8 Hz, proton at3'-site of aromatic ring), 6.14 (1H, bs, amide group proton), 5.02 (2H, d, methylene group proton of naphtylmethyl group), 1.97 (3H, s, methyl group proton bound to 2-site of propene).

$^{13}$C-NMR (heavy chloroform, δ ppm): 168.6 (quaternary carbon, carbonyl group carbon at 1-site of propene), 144.4 (quaternary carbon, carbon at 2'-site of aromatic ring), 133.9 (quaternary carbon, carbon at 1"-site of naphtyl aromatic ring), 133.4 (quaternary carbon, carbon at 9"- or 10"-site of naphtyl aromatic ring), 132.9 (quaternary carbon, carbon at 9"- or 10"-site of naphtyl aromatic ring), 131.5 (quaternary carbon, carbon at 2-site of propene), 131.0 (CH, carbon at 3-site of propene), 129.6 (CH, carbon at 4'- site of cinnamyl aromatic ring), 129.1 (CH, carbon at 6'- site of cinnamyl aromatic ring), 128.9 (CH, carbon at 5"- or 8"-site of naphtyl aromatic ring), 128.8 (CH, carbon at 5"- or 8"-site of naphtyl aromatic ring), 127.0 (CH, carbon at 2"-site of naphtyl aromatic ring), 126.7 (CH, carbon at 3"-site of naphtyl aromatic ring), 126.1 (CH, carbon at 6"- or 7"-site of naphtyl aromatic ring), 125.4 (CH, carbon at 6"- or 7"-site of naphtyl aromatic ring), 123.5 (CH, carbon at 4"-site of naphtyl aromatic ring), 121.3 (quaternary carbon, carbon at 1'- site of cinnamyl aromatic ring), 118.1 (CH, carbon at 5'- site of cinnamyl aromatic ring), 115.5 (CH, carbon at 3'- site of cinnamyl aromatic ring), 42.3 ($CH_2$, methylene group carbon of naphtylmethyl group), 14.3 ($CH_3$, methyl group carbon bound to 2-site of propene).

Synthesis of (E) 3-(2-amino-4-dimethylaminophenyl)-2-methyl-2-propenoic acid (E) ethyl 3-(2-amino-4-dimethylaminophenyl)-2-methyl-2-propenate was dissolved in tetrahydrofuran (THF); and, with 10 ml of a 1-N aqueous sodium hydroxide solution being added thereto, the mixture was reacted for 4 hours at 40° C. After the completion of the reaction was verified by TLC, the mixture was cooled with 1-N hydrochloric acid being added thereto, and the precipitated crystal was filtered out, whereby the aimed compound was obtained.

Synthesis of (E) 3-(2-amino-4-dimethylaminophenyl)-2-methyl-2-propenoic acid

In a process similar to other synthesizing examples, a p-nitrophenyl ester derivative was synthesized from 3-(2-amino-4-dimethylaminophenyl)-2-methyl-2-propenoic acid obtained above. Specifically, 3-(2-amino-4-dimethylaminophenyl)-2-methyl-2-propenoic acid and p-nitrophenol (manufactured by Wako Pure Chemical Industries, Ltd.) were dissolved in dichloromethane, and after dimethylaminopyridine (manufactured by Wako Pure Chemical Industries, Ltd.) were added thereto, 1-ethyl-3-(3dimethylaminopropyl)-carbodiimide hydrochloride (EDC-HCl) (manufactured by Wako Pure Chemical Industries, Ltd.) were added thereto in portions while the mixture was stirred under cooling with ice. The liquid was returned to room temperature, and was stirred for 20 hours. After the end point of the reaction was verified by TLC, the reaction liquid was concentrated under a reduced pressure and was dissolved in ethyl acetate. The resulting solution was washed several times with a 5% aqueous sodium hydrogencarbonate solution and then with a saturated aqueous sodium chloride solution, and was dried with magnesium sulfate anhydride. Thereafter, the solvent was evaporated, whereby a crude product was obtained. This product was recrystallized from ethanol, whereby the aimed compound was obtained.

As explained in the foregoing, the reagents for preparation of caged compounds in accordance with the present invention have characteristic structures, and can prepare caged compounds with new structures by a simple reaction.

What is claimed is:

1. A reagent for preparation of a caged compound, having an N-succinimidyl aminocinnamate structure expressed by the following formula 1:

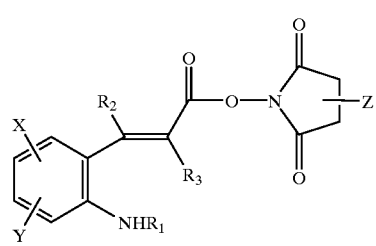

formula 1 where X and Y may be identical or different, and each is selected from the group consisting of a hydrogen atom, a halogen atom, an alkyl group having a carbon number from 1 to 4, an alkyloxy group having a carbon number from 1 to 4, a benzo group, and an alkylamino group having a carbon number from 1 to 4; $R_1$ is selected from the group consisting of a hydrogen atom, an alkyl group having a carbon number from 1 to 4, and a group expressed by the following formula 2:

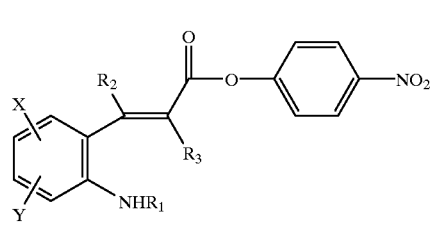

formula 2 where $R_6$ is selected from the group consisting of an alkyl group having a carbon number from 1 to 4, a phenyl group, and an alkylsilyl group having a carbon number from 1 to 4, and n represents an integer from 0 to 2;

$R_2$ and $R_3$ may be identical or different, and each is selected from the group consisting of a hydrogen and an alkyl group having a carbon number from 1 to 4; and Z is selected from the group consisting of a hydrogen atom and $SO_3M$, where M is selected from the group consisting of a hydrogen atom, an alkali metal, and an alkaline-earth metal.

2. A reagent for preparation of a caged compound, having a p-nitrophenyl aminocinnamate structure expressed by the following formula 3:

formula 3 where X and Y may be identical or different, and each is selected from the group consisting of a hydrogen atom, a halogen atom, an alkyl group having a carbon number from 1 to 4, an alkyloxy group having a carbon number from 1 to 4, a benzo group, and an alkylamino group having a carbon number from 1 to 4; $R_1$ is selected from the group consisting of a hydrogen atom, an alkyl group having a carbon number from 1 to 4, and a group expressed by the following formula 2:

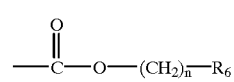

formula 2 where $R_6$ is selected from the group consisting of an alkyl group having a carbon number from 1 to 4, a phenyl group, and an alkylsilyl group having a carbon number from 1 to 4, and n represents an integer from 0 to 2; and $R_2$ and $R_3$ may be identical or different, and each is selected from the group consisting of a hydrogen and an alkyl group having a carbon number from 1 to 4.

3. A caging method comprising a step of preparing a caged compound by reacting the reagent for preparing of a caged compound according to claim 1 with a physiologically active substance.

4. A caging method comprising a step of preparing a caged compound by reacting the reagent for preparation of a caged compound according to claim 2 with a physiologically active substance.

* * * * *